(12) United States Patent
Lerchen et al.

(10) Patent No.: US 11,643,469 B2
(45) Date of Patent: May 9, 2023

(54) SPECIFIC ANTIBODY-DRUG-CONJUGATES (ADCS) WITH KSP INHIBITORS AND ANTI-CD123-ANTIBODIES

(71) Applicant: Bayer Pharma Aktiengesellschaft, Berlin (DE)

(72) Inventors: Hans-Georg Lerchen, Leverkusen (DE); Anne-Sophie Rebstock, Champagne au Mont d'Or (FR); Yolanda Cancho Grande, Leverkusen (DE); Sven Wittrock, Berlin (DE); Beatrix Stelte-Ludwig, Wülfrath (DE); Dennis Kirchhoff, Berlin (DE); Christoph Mahlert, Wuppertal (DE); Simone Greven, Dormagen (DE); Stephan Märsch, Cologne (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 17/733,760

(22) Filed: Apr. 29, 2022

(65) Prior Publication Data

US 2022/0267457 A1 Aug. 25, 2022

Related U.S. Application Data

(63) Continuation of application No. 17/225,947, filed on Apr. 8, 2021, which is a continuation of application No. 16/310,285, filed as application No. PCT/EP2017/063951 on Jun. 8, 2017, now Pat. No. 11,001,636.

(30) Foreign Application Priority Data

Jun. 15, 2016 (EP) .................................... 16174654

(51) Int. Cl.
| | | |
|---|---|---|
| *A61K 39/00* | (2006.01) | |
| *C07K 16/28* | (2006.01) | |
| *A61K 47/68* | (2017.01) | |
| *A61P 35/00* | (2006.01) | |
| *A61K 31/40* | (2006.01) | |

(52) U.S. Cl.
CPC .......... *C07K 16/2866* (2013.01); *A61K 31/40* (2013.01); *A61K 47/6803* (2017.08); *A61K 47/6849* (2017.08); *A61K 47/6851* (2017.08); *A61P 35/00* (2018.01)

(58) Field of Classification Search
CPC ............ C07K 16/2866; A61K 47/6849; A61K 47/6851; A61P 35/00
See application file for complete search history.

(56) References Cited

U.S. PATENT DOCUMENTS

| | | |
|---|---|---|
| 4,399,216 A | 8/1983 | Axel et al. |
| 4,474,893 A | 10/1984 | Reading |
| 4,510,245 A | 4/1985 | Cousens et al. |
| 4,634,665 A | 1/1987 | Axel et al. |
| 4,714,681 A | 12/1987 | Reading |
| 4,816,397 A | 3/1989 | Boss et al. |
| 4,816,567 A | 3/1989 | Cabilly et al. |
| 4,925,648 A | 5/1990 | Hansen et al. |
| 4,968,615 A | 11/1990 | Koszinowski et al. |
| 5,168,062 A | 12/1992 | Stinski |
| 5,179,017 A | 1/1993 | Axel et al. |
| 5,270,163 A | 12/1993 | Gold et al. |
| 5,573,920 A | 11/1996 | Randle |
| 5,601,819 A | 2/1997 | Wong et al. |
| 6,177,078 B1 | 1/2001 | Lopez |
| 7,318,924 B2 | 1/2008 | McKenzie et al. |
| 7,465,449 B2 | 12/2008 | Violette et al. |
| 7,598,350 B2 | 10/2009 | Liu et al. |
| 7,628,986 B2 | 12/2009 | Weber et al. |
| 7,662,581 B1 | 2/2010 | Bussiere et al. |
| 10,022,453 B2 | 7/2018 | Lerchen et al. |
| 10,485,880 B2 | 11/2019 | Lerchen et al. |
| 10,744,205 B2 | 8/2020 | Lerchen et al. |
| 10,787,521 B2 * | 9/2020 | Bonvini ............. C07K 16/2866 |
| 10,973,923 B2 | 4/2021 | Lerchen et al. |
| 11,001,636 B2 | 5/2021 | Lerchen et al. |

(Continued)

FOREIGN PATENT DOCUMENTS

| | | |
|---|---|---|
| CA | 2990411 A1 | 12/2016 |
| CA | 3018630 A1 | 9/2017 |

(Continued)

OTHER PUBLICATIONS

Bajjuri et al. The legumain protease-activated auristatin prodrugs suppress tumor growth and metastasis without toxicity. ChemMedChem 6(1):54-59 (2011).
Bebbington et al. High-level expression of a recombinant antibody from myeloma cells using a glutamine synthetase gene as an amplifiable selectable marker. Biotechnology 10(2):169-75 (1992).
Berger. Isolation of Cytoplamic RNA: Ribonucleoside-Vanadyl Complexes. Methods in Enzymology 152:227-234 (1987).
Bird et al. Single-chain antigen-binding proteins. Science 242(4877):423-426 (1988).

(Continued)

*Primary Examiner* — Sheela J. Huff
(74) *Attorney, Agent, or Firm* — Wilson Sonsini Goodrich & Rosati

(57) ABSTRACT

The invention relates to specific Antibody-Drug-Conjugates (ADCs) with KSP inhibitors and anti-CD123-antibodies, to the use of these conjugates for the treatment and/or prophylaxis of diseases and to the use of these conjugates for preparing medicaments for treatment and/or prevention of diseases, in particular hyperproliferative and/or angiogenic disorders such as, for example, cancer diseases. Such treatments can be carried out as monotherapy or else in combination with other medicaments or further therapeutic measures.

15 Claims, 21 Drawing Sheets

Specification includes a Sequence Listing.

(56) References Cited

U.S. PATENT DOCUMENTS

| | | |
|---|---|---|
| 11,071,788 B2 | 7/2021 | Lerchen et al. |
| 11,123,439 B2 | 9/2021 | Lerchen et al. |
| 2007/0264253 A1 | 11/2007 | Liu et al. |
| 2008/0193445 A1 | 8/2008 | Goetsch et al. |
| 2009/0175796 A1 | 7/2009 | Raitano et al. |
| 2009/0252742 A1 | 10/2009 | Bergstein |
| 2010/0028947 A1 | 2/2010 | Goletz et al. |
| 2014/0322247 A1 | 10/2014 | Barsanti et al. |
| 2016/0031996 A1 | 2/2016 | Lopez et al. |
| 2016/0346402 A1 | 12/2016 | Lerchen et al. |
| 2018/0015176 A1 | 1/2018 | Lerchen et al. |
| 2018/0169256 A1 | 6/2018 | Lerchen et al. |
| 2018/0318437 A1 | 11/2018 | Lerchen et al. |
| 2019/0077752 A1 | 3/2019 | Lerchen et al. |
| 2019/0262463 A1 | 8/2019 | Lerchen et al. |
| 2019/0328897 A1 | 10/2019 | Lerchen et al. |
| 2019/0330357 A1 | 10/2019 | Lerchen et al. |
| 2019/0351066 A1 | 11/2019 | Lerchen et al. |
| 2019/0365916 A1 | 12/2019 | Lerchen et al. |
| 2020/0138970 A1 | 5/2020 | Lerchen et al. |
| 2021/0230284 A1 | 7/2021 | Lerchen et al. |
| 2021/0252161 A1 | 8/2021 | Lerchen et al. |
| 2021/0275686 A1 | 9/2021 | Johannes et al. |
| 2021/0386864 A1 | 12/2021 | Lerchen et al. |
| 2022/0016258 A1 | 1/2022 | Lerchen et al. |
| 2022/0362392 A1 | 11/2022 | Lerchen et al. |

FOREIGN PATENT DOCUMENTS

| | | | |
|---|---|---|---|
| CN | 103025761 | A | 4/2013 |
| EP | 0586002 | A2 | 3/1994 |
| EP | 0712863 | A1 | 5/1996 |
| EP | 0719859 | A1 | 7/1996 |
| EP | 1773884 | A2 | 4/2007 |
| EP | 1900750 | A1 | 3/2008 |
| EP | 1911766 | A1 | 4/2008 |
| EP | 2073842 | A2 | 7/2009 |
| EP | 2121008 | A2 | 11/2009 |
| EP | 2195023 | A1 | 6/2010 |
| EP | 2311879 | A2 | 4/2011 |
| EP | 2426148 | A1 | 3/2012 |
| EP | 2606069 | B1 | 7/2014 |
| EP | 2426148 | B1 | 8/2015 |
| WO | WO-9100360 | A1 | 1/1991 |
| WO | WO-9105871 | A1 | 5/1991 |
| WO | WO-9205793 | A1 | 4/1992 |
| WO | WO-9208802 | A1 | 5/1992 |
| WO | WO-9215683 | A1 | 9/1992 |
| WO | WO-9317715 | A1 | 9/1993 |
| WO | WO-9708320 | A1 | 3/1997 |
| WO | WO-9735616 | A1 | 10/1997 |
| WO | WO-9947554 | A1 | 9/1999 |
| WO | WO-0109192 | A1 | 2/2001 |
| WO | WO-0162931 | A2 | 8/2001 |
| WO | WO-0188138 | A1 | 11/2001 |
| WO | WO-0212501 | A2 | 2/2002 |
| WO | WO-02077033 | A1 | 10/2002 |
| WO | WO-02088170 | A2 | 11/2002 |
| WO | WO-02092771 | A2 | 11/2002 |
| WO | WO-02100348 | A2 | 12/2002 |
| WO | WO-03034903 | A2 | 5/2003 |
| WO | WO-03040979 | A1 | 5/2003 |
| WO | WO-03049527 | A2 | 6/2003 |
| WO | WO-03060064 | A2 | 7/2003 |
| WO | WO-03083041 | A2 | 10/2003 |
| WO | WO-03106495 | A2 | 12/2003 |
| WO | WO-2004056847 | A2 | 7/2004 |
| WO | WO-2004091375 | A2 | 10/2004 |
| WO | WO-2004100873 | A2 | 11/2004 |
| WO | WO-2005009369 | A2 | 2/2005 |
| WO | WO-2005010151 | A2 | 2/2005 |
| WO | WO-2005051922 | A1 | 6/2005 |
| WO | WO-2005056606 | A2 | 6/2005 |
| WO | WO-2005081711 | A2 | 9/2005 |
| WO | WO-2005081854 | A2 | 9/2005 |
| WO | WO-2005090407 | A1 | 9/2005 |
| WO | WO-2006002236 | A1 | 1/2006 |
| WO | WO-2006044825 | A2 | 4/2006 |
| WO | WO-2006060737 | A2 | 6/2006 |
| WO | WO-2006062779 | A2 | 6/2006 |
| WO | WO-2006066896 | A2 | 6/2006 |
| WO | WO-2006074418 | A2 | 7/2006 |
| WO | WO-2006089232 | A2 | 8/2006 |
| WO | WO-2006100036 | A1 | 9/2006 |
| WO | WO-2007002222 | A2 | 1/2007 |
| WO | WO-2007021794 | A1 | 2/2007 |
| WO | WO-2007024536 | A2 | 3/2007 |
| WO | WO-2007038637 | A2 | 4/2007 |
| WO | WO-2007064759 | A2 | 6/2007 |
| WO | WO-2007070538 | A2 | 6/2007 |
| WO | WO-2008004834 | A1 | 1/2008 |
| WO | WO-2008028686 | A2 | 3/2008 |
| WO | WO-2008031056 | A2 | 3/2008 |
| WO | WO-2008036688 | A2 | 3/2008 |
| WO | WO-2008047242 | A2 | 4/2008 |
| WO | WO-2008070593 | A2 | 6/2008 |
| WO | WO-2008086122 | A2 | 7/2008 |
| WO | WO-2008092117 | A2 | 7/2008 |
| WO | WO-2008127735 | A1 | 10/2008 |
| WO | WO-2008140603 | A2 | 11/2008 |
| WO | WO-2009000786 | A2 | 12/2008 |
| WO | WO-2009020933 | A2 | 2/2009 |
| WO | WO-2009023265 | A1 | 2/2009 |
| WO | WO-2009026274 | A1 | 2/2009 |
| WO | WO-2009032661 | A1 | 3/2009 |
| WO | WO-2009033094 | A2 | 3/2009 |
| WO | WO-2009068204 | A1 | 6/2009 |
| WO | WO-2009070844 | A1 | 6/2009 |
| WO | WO-2009080829 | A1 | 7/2009 |
| WO | WO-2009080830 | A1 | 7/2009 |
| WO | WO-2009123894 | A2 | 10/2009 |
| WO | WO-2009140177 | A2 | 11/2009 |
| WO | WO-2010022736 | A2 | 3/2010 |
| WO | WO-2010112413 | A1 | 10/2010 |
| WO | WO-2010115554 | A1 | 10/2010 |
| WO | WO-2011044368 | A1 | 4/2011 |
| WO | WO-2012021934 | A1 | 2/2012 |
| WO | WO-2012143499 | A2 | 10/2012 |
| WO | WO-2012171020 | A1 | 12/2012 |
| WO | WO-2013076186 | A1 | 5/2013 |
| WO | WO-2013087579 | A1 | 6/2013 |
| WO | WO-2013173820 | A2 | 11/2013 |
| WO | WO-2014061277 | A1 | 4/2014 |
| WO | WO-2014093640 | A1 | 6/2014 |
| WO | WO-2014131739 | A2 | 9/2014 |
| WO | WO-2014151030 | A1 | 9/2014 |
| WO | WO-2014160160 | A2 | 10/2014 |
| WO | WO-2014198817 | A1 | 12/2014 |
| WO | WO-2015054659 | A1 | 4/2015 |
| WO | WO-2015089449 | A2 | 6/2015 |
| WO | WO-2015096982 | A1 | 7/2015 |
| WO | WO-2015138615 | A3 | 12/2015 |
| WO | WO-2015189143 | A1 | 12/2015 |
| WO | WO-2016020791 | A1 | 2/2016 |
| WO | WO-2016028573 | A1 | 2/2016 |
| WO | WO-2016096610 | A1 | 6/2016 |
| WO | WO-2016201065 | A1 | 12/2016 |
| WO | WO-2016207089 | A1 | 12/2016 |
| WO | WO-2016207090 | A2 | 12/2016 |
| WO | WO-2016207094 | A1 | 12/2016 |
| WO | WO-2016207098 | A1 | 12/2016 |
| WO | WO-2016207103 | A1 | 12/2016 |
| WO | WO-2016207104 | A1 | 12/2016 |
| WO | WO-2017162663 | A1 | 9/2017 |
| WO | WO-2017216028 | A1 | 12/2017 |
| WO | WO-2018114578 | A1 | 6/2018 |
| WO | WO-2018114798 | A1 | 6/2018 |
| WO | WO-2018114804 | A1 | 6/2018 |
| WO | WO-2019243159 | A1 | 12/2019 |

OTHER PUBLICATIONS

Borrebaeck. Antibody Engineering. 2nd edition, Ed., Oxford University Press, New York, 1995.

(56) References Cited

OTHER PUBLICATIONS

Brand et al. Prospect for Anti-HER2 Receptor Therapy in Breast Cancer. Anticancer Research 26(1B):463-470 (2006).
Brown et al. TWEAK binding to the Fn14 cysteine-rich domain depends on charged residues located in both the AI and D2 modules. Biochem J. 397(2):297-304 (2006).
Chen et al. Cloning, isolation, and characterization of mammalian legumain, an asparaginyl endopeptidase. J. Biol. Chem. 272:8090-8098 (1997).
Chothia et al. Canonical structures for the hypervariable regions of immunoglobulins. J Mol Biol 196:901-917 (1987).
Clackson et al. Making antibody fragments using phage display libraries. Nature 352(6336):624-628 (1991).
Co-pending U.S. Appl. No. 17/374,756, inventors Lerchen; Hans-Georg et al., filed Jul. 13, 2021.
Culp et al. Antibodies to TWEAK receptor inhibit human tumor growth through dual mechanisms. Clin Cancer Res. 16(2):497-508 (2010).
Delfourne et al. Synthesis and in vitro antitumor activity of phenanthrolin-7-one derivatives, analogues of the marine pyridoacridine alkaloids ascididemin and meridine: structure-activity relationship. J. Med. Chem. 46(16):3536-3545 (2003).
Donohue et al. TWEAK is an Endothelial Cell Growth and Chemotactic Factor that also Potentiates F-2 and VEGF-A Mitogenic Activity. Arterioscler Thromb Vasc Biol, 23(4):594-600 (2003).
Doronina et al. Development of potent monoclonal antibody auristatin conjugates for cancer therapy. Nat Biotechnol 21:778-784 (2003).
Dubowchik et al. Cathepsin B-labile dipeptide linkers for lysosomal release of doxorubicin from internalizing immunoconjugates: model studies of enzymatic drug release and antigen-specific in vitro anticancer activity. Bioconjugate Chem. 13:855-869 (2002).
Dubowchik et al. Cathepsin B-sensitive dipeptide prodrugs. 1. A model study of structural requirements for efficient release of doxorubicin. Bioorg Med Chem Lett 8:3341-3346 (1998).
Ducry et al. Antibody-drug conjugates: linking cytotoxic payloads to monoclonal antibodies. Bioconjug Chem. 21(1):5-13 (2010).
Durocher et al., High-level and high-throughput recombinant protein production by transient transfection of suspension-growing human HEK293-EBNA1 cells. Nucleic acids research, 30(2):e9 (2002).
Fan et al. Improving the efficiency of CHO cell line generation using glutamine synthetase gene knockout cells. Biotechnol Bioeng. 109(4):1007-15 (2012).
Gebauer et al. Engineered protein scaffolds as next-generation antibody therapeutics. Curr. Opinion in Chem. Biol. 13:245-255 (2009).
Harlow, et al. Using Antibodies: A Laboratory Manual. Cold Spring Harbor Laboratory, Cold Spring Harbor, N.Y. 1999.
Hoet et al. Generation of high-affinity human antibodies by combining donor-derived and synthetic complementarity-determining-region diversity. Nature Biotechnology 23(3):344-348 (Mar. 2005).
Hoogenboom. Selecting and screening recombinant antibody libraries. Nat Biotechnol. 23(9):1105-16 (2005).
Huston et al. Protein engineering of antibody binding sites: recovery of specific activity in an anti-digoxin single-chain Fv analogue produced in *Escherichia coli*. PNAS USA 85(16):5879-5883 (1988).
Ishii. Legumain: asparaginyl endopeptidase . Methods Enzymol. 244:604-615 (1994).
Johnson et al. The clinical impact of screening and other experimental tumor studies. Cancer Treat Rev 2(1):1-31 (1975).
Junutula et al. Site-specific conjugation of a cytotoxic drug to an antibody improves the therapeutic index. Nat Biotechnol. 26(8):925-32 (2008).
Kabat et al. Sequences of proteins of immunological interest. NIH Publ. No. 91-3242 1:647-669 (1991).
Kaufman, et al. Amplification and expression of sequences cotransfected with a modular dihydrofolate reductase complementary dna gene. J Mol Biol. ;159(4):601-21.
Keefe et al. Aptamers as therapeutics. Nat. Rev. Drug Discov. 9:537-550 (2010).
Kohler et al. Continuous cultures of fused cells secreting antibody of predefined specificity. Nature256(5517):495-497 (1975).
Kontermann, et al. Antibody Engineering. Springer Lab Manual, Springer Verlag, 2001.
Kostelny et al. Formation of a bispecific antibody by the use of leucine zippers. J. Immunol. 148(5):1547-1553 (1992).
Kuo et al. Antibody internalization after cell surface antigen binding is critical for immunotoxin development. Bioconjug Chem. 20(10):1975-82 (2009).
Lambert. Drug-conjugated monoclonal antibodies for the treatment of cancer. Curr. Opin. Pharmacol. 5:543-549 (2005).
Lang et al. Cellular Incorporation of Unnatural Amino Acids and Bioorthogonal Labeling of Proteins, Chem.Rev. 114:4764-4806 (2014).
Lefranc et al. IMGTO, the international ImMunoGeneTics information system®. Nucl. Acids Res 37(Database issue):D1006-D1012 (2009).
Lerchen et al. Abstract 3234: Development of potent and selective antibody-drug conjugates with 3-yrrole-based KSP inhibitors as novel payload class. Cancer Research, AACR 77(13):1-3 (2017).
Li et al. Design, synthesis and evaluation of anti-CD123 antibody drug conjugates Bioorg Med Chem 24(22):5855-5860 (2016).
Lonberg et al. Human antibodies from transgenic mice. Int Rev Immunol. 13(1):65-93 (1995).
Mayer et al. Small molecule inhibitor of mitotic spindle bipolarity identified in a phenotype-based screen. Science 286(5441):971-974 (1999).
McCafferty et al. Phage Antibodies: Filamentous Phage Displaying Antibody Variable Domains. Nature 348:552-554 (1990).
Michaelson et al. Development of an Fn14 agonistic antibody as an anti-tumor agent. MAbs 3(4):362-375 (2011).
Nakayama et al. Characterization of murine TWEAK and its receptor (Fn14) by monoclonal antibodies . Biochem Biophy Res Comm 306:819-825 (2003).
Nuttall et al. Display scaffolds: protein engineering for novel therapeutics. Curr. Opinion in Pharmacology 8:609-615 (2008).
Olsson et al. Human-human monoclonal antibody-producing hybridomas: Technical aspects. Meth Enzymol. 92:3-16 (1983).
Paul, W. E., ed., Fundamental Immunology, 4th Ed., Lippincott-Raven, Philadelphia (1999).
PCT/EP2014/077144 International Search Report and Written Opinion dated Apr. 29, 2015.
PCT/EP2015/079273 International Search Report and Written Opinion dated Mar. 24, 2016.
PCT/EP2016/064133 International Search Report and Written Opinion dated Sep. 19, 2016.
PCT/EP2017/063951 International Search Report and Written Opinion dated Sep. 12, 2017.
PCT/EP2017/082789 International Search Report and Written Opinion dated Apr. 19, 2018.
PCT/EP2017/083313 International Search Report and Written Opinion dated Apr. 23, 2018.
Pellegrini et al. Structure of the extracellular domains of human and Xenopus Fn14: implications in the evolution of TWEAK and Fn14 interactions. FEBS 280:1818-1829 (2013).
Peterson et al. Cathepsin substrates as cleavable peptide linkers in bioconjugates, selected from a fluorescence quench combinatorial library. Bioconjugate Chem. 9:618-626 (1998).
Polson et al. Antibody-drug conjugates for the treatment of non-Hodgkin's lymphoma: target and linker-drug selection. Cancer Res. 69(6):2358-64 (2009).
Polson et al. Antibody-drug conjugates targeted to CD79 for the treatment of non-Hodgkin lymphoma. Blood 110(2):616-623 (2007).
Queen et al. A humanized antibody that binds to the interleukin 2 receptor. PNAS USA 86:10029-10032 (1989).
Rashidian et al. Enzymatic labeling of proteins: techniques and approaches. Bioconjugate Chem. 24:1277-1294 (2013).
Schinkel et al. Absence of the mdr1a P-Glycoprotein in mice affects tissue distribution and pharmacokinetics of dexamethasone, digoxin, and cyclosporin A. J. Clin. Invest. 96:1698-1705 (1995).
Schwab et al. Comparison of in vitro P-glycoprotein screening assays: recommendations for their use in drug discovery. J. Med. Chem. 46:1716-1725 (2003).

(56) References Cited

OTHER PUBLICATIONS

Söderlind et al. Recombining germline-derived CDR sequences for creating diverse single-framework antibody libraries. Nature Biotechnology 18:852-856 (Aug. 1, 2000).

Seki et al. Practical synthesis of (R)-4-mercaptopyrrolidine-2-thione from L-aspartic acid. Preparation of a novel orally active 1-beta-methylcarbapenem, TA-949. J. Org. Chem. 65:517-522 (2000).

Senter. Potent antibody drug conjugates for cancer therapy. Curr. Opin. Chem. Biol 13:235-244 (2009).

Sommer et al. Abstract 46: Preclinical activity of novel antibody-drug conjugates with pyrrole-based kinesin spindle protein inhibitors targeting different tumor antigens. Cancer Research, AACR 77(13):1-3 (2017).

Stern, L. et al., A novel antitumor prodrug platform designed to be cleaved by the endoprotease legumain. Bioconj. Chem., 20:500-510 (2009).

Strome et al. A mechanistic perspective of monoclonal antibodies in cancer therapy beyond target-related effects. The Oncologist 12:1084-95 (2007).

Sun et al. Monoclonal antibody 7G3 recognizes the N-terminal domain of the human interleukin-3 (IL-3) receptor alpha-chain and functions as a specific IL-3 receptor antagonist. Blood 87(1):83-92 (1996).

Sun et al. Reduction-Alkylation Strategies for the Modification of Specific Monoclonal Antibody Disulfides. Bioconjugate Chem. 16:1282-1290 (2005).

Tao et al. Induction of apoptosis by an inhibitor of the mitotic kinesin KSP requires both activation of the spindle assembly checkpoint and mitotic slippage. Cancer Cell 8(1):49-59 (2005).

Tom et al. Transient expression in HEK293-EBNA1 cells, in Expression Systems: Methods Express, Dyson, M.R. et al. eds., Scion Publishing Ltd.: Oxfordshire, pp. 204-223 (2007).

Troutman et al. Novel experimental parameters to quantify the modulation of absorptive and secretory transport of compounds by P-glycoprotein in cell culture models of intestinal epithelium. Pharm. Res. 20(8):1210-1224 (2003).

Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).

Urlaub et al. Deletion of the diploid dihydrofolate reductase locus from cultured mammalian cells. Cell 33(2):405-12 (1983).

Urlaub et al. Isolation of Chinese hamster cell mutants deficient in dihydrofolate reductase activity. PNAS USA 77:4216-4220 (1980).

U.S. Appl. No. 16/310,285 Office Action dated Aug. 24, 2020.

Wang et al. Protease-Activatable Hybrid Nanoprobe for Tumor Imaging. Adv. Funct. Mater. 24(34):5443-5453 (2014).

Wiley et al. A Novel TNF Receptor Family Member Binds TWEAK and Is Implicated in Angiogenesis. Immunity 15:837-846 (2001).

Wu et al. Arming antibodies: prospects and challenges for immunoconjugates. Nat. Biotechnol. 23:1137-1146 (2005).

Wu et al. Targeting cell-impermeable prodrug activation to tumor microenvironment eradicates multiple drug-resistant neoplasms. Cancer Res. 66:970-980 (2006).

Zhou et al. Development and Characterization of a Potent Immunoconjugate Targeting the Fn14 Receptor on Solid Tumor Cell. Mol Cancer Therapeutics 10(7):1276-1288 (2011).

Zhou et al. The TWEAK Receptor Fn14 is a Novel Therapeutic Target in Melanoma: Immunotoxins Targeting Fn14 Receptor for Malignant Melanoma Treatment. J. Invest Dermatol. 133(4):1052-1062 (2013).

Co-pending U.S. Appl. No. 17/812,095, inventors Lerchen; Hans-Georg et al., filed Jul. 12, 2022.

U.S. Appl. No. 17/225,947 Office Action dated Jan. 17, 2023.

* cited by examiner

FIG. 1A

<SEQ ID NO:1>
EVQLVQSGAEVKKPGESLKISCKGSGYSFTDYYMKWARQMPGKGLEWMGDIIPSNGATFYNQKFKGQVT
ISADKSISTTYLQWSSLKASDTAMYYCARSHLLRASWFAYWGQGTMVTVSS

<SEQ ID NO:2>
DYYMK

<SEQ ID NO:3>
DIIPSNGATFYNQKFKG

<SEQ ID NO:4>
ARSHLLRASWFAY

<SEQ ID NO:5>
DIVMTQSPDSLAVSLGERATINCESSQSLLNSGNQKNYLTWYQQKPGQPPKPLIYWASTRESGVPDRFS
GSGSGTDFTLTISSLQAEDVAVYYCQNDYSYPYTFGQGTKLEIK

<SEQ ID NO:6>
ESSQSLLNSGNQKNYLT

<SEQ ID NO:7>
WASTRES

<SEQ ID NO:8>
QNDYSYPYT

<SEQ ID NO:9>
EVQLVQSGAEVKKPGESLKISCKGSGYSFTDYYMKWARQMPGKGLEWMGDIIPSNGATFYNQKFKGQVT
ISADKSISTTYLQWSSLKASDTAMYYCARSHLLRASWFAYWGQGTMVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:10>
DIVMTQSPDSLAVSLGERATINCESSQSLLNSGNQKNYLTWYQQKPGQPPKPLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:11>
QVQLVQSGAEVKKPGASVKVSCKASGYTFTDYYMKWVRQAPGQGLEWMGDIIPSNGATFYAQKFQGRVT
MTRDTSTSTVYMELSSLRSEDTAVYYCARSHLLRASWFAYWGQGTLVTVSS

<SEQ ID NO:12>
DYYMK

<SEQ ID NO:13>
DIIPSNGATFYAQKFQG

<SEQ ID NO:14>
SHLLRASWFAY

FIG. 1B

<SEQ ID NO:15>
DIVMTQSPDSLAVSLGERATINCKSSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:16>
KSSQSLLNSGNQKNYLT

<SEQ ID NO:17>
WASTRES

<SEQ ID NO:18>
QNDYSYPYT

<SEQ ID NO:19>
QVQLVQSGAEVKKPGASVKVSCKASGYTFTDYYMKWVRQAPGQGLEWMGDIIPSNGATFYAQKFQGRVT
MTRDTSTSTVYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:20>
DIVMTQSPDSLAVSLGERATINCKSSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:21>
QVQLVQSGAEVKKPGSSVKVSCKASGGTFSDYYMKWVRQAPGQGLEWMGDIIPSNGATFYAQKFQGRVT
ITADESTSTAYMELSSLRSEDTAVYYCARSHLLRASWFAYWGQGTLVTVSS

<SEQ ID NO:22>
DYYMK

<SEQ ID NO:23>
DIIPSNGATFYAQKFQG

<SEQ ID NO:24>
SHLLRASWFAY

<SEQ ID NO:25>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:26>
ESSQSLLNSGNQKNYLT

<SEQ ID NO:27>
WASTRES

<SEQ ID NO:28>
QNDYSYPYT

FIG. 1C

<SEQ ID NO:29>
QVQLVQSGAEVKKPGSSVKVSCKASGGTFSDYYMKWVRQAPGQGLEWMGDIIPSNGATFYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:30>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:31>
QVQLVQSGAEVKKPGSSVKVSCKASGGTFSDYYMKWVRQAPGQGLEWMGDIIPSNGATFYAQKFQGRVT
ITADESTSTAYMELSSLRSEDTAVYYCARSHLLRASWFAYWGQGTLVTVSS

<SEQ ID NO:32>
DYYMK

<SEQ ID NO:33>
DIIPSNGATFYAQKFQG

<SEQ ID NO:34>
SHLLRASWFAY

<SEQ ID NO:35>
DIVMTQSPDSLAVSLGERATINCKSSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:36>
KSSQSLLNSGNQKNYLT

<SEQ ID NO:37>
WASTRES

<SEQ ID NO:38>
QNDYSYPYT

<SEQ ID NO:39>
QVQLVQSGAEVKKPGSSVKVSCKASGGTFSDYYMKWVRQAPGQGLEWMGDIIPSNGATFYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:40>
DIVMTQSPDSLAVSLGERATINCKSSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

FIG. 1D

<SEQ ID NO:41>
QVQLQESGPGLVKPSQSLSLTCSVTDYSITSGYYWNWIRQFPGNKLEWMGYISYDGSNNYNPSLKNRIS
ITRDTSKNQFFLKLSSVTTEDTATYYCSRGEGFYFDSWGQGTTLTVSS

<SEQ ID NO:42>
SGYYWN

<SEQ ID NO:43>
YISYDGSNNYNPSLKN

<SEQ ID NO:44>
GEGFYFDS

<SEQ ID NO:45>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIK

<SEQ ID NO:46>
KSSQSLFFGSTQKNYLA

<SEQ ID NO:47>
WASTRES

<SEQ ID NO:48>
QQYYNYPWT

<SEQ ID NO:49>
QVQLQESGPGLVKPSQSLSLTCSVTDYSITSGYYWNWIRQFPGNKLEWMGYISYDGSNNYNPSLKNRIS
ITRDTSKNQFFLKLSSVTTEDTATYYCSRGEGFYFDSWGQGTTLTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPG

<SEQ ID NO:50>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:51>
QVQLVQSGAEVKKPGSSVKVSCKASGGTFSDYYMKWVRQAPGQGLEWMGGIIPSNGATFYAQKFQGRVT
ITADESTSTAYMELSSLRSEDTAVYYCARSHLLRASWFAYWGQGTLVTVSS

<SEQ ID NO:52>
DYYMK

<SEQ ID NO:53>
GIIPSNGATFYAQKFQG

<SEQ ID NO:54>
SHLLRASWFAY

FIG. 1E

```
<SEQ ID NO:55>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:56>
ESSQSLLNSGNQKNYLT

<SEQ ID NO:57>
WASTRES

<SEQ ID NO:58>
QNDYSYPYT

<SEQ ID NO:59>
QVQLVQSGAEVKKPGSSVKVSCKASGGTFSDYYMKWVRQAPGQGLEWMGGIIPSNGATFYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:60>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:61>
QVQLVQSGAEVKKPGSSVKVSCKASGGTFSDYYMKWVRQAPGQGLEWMGDIIPSFGATFYAQKFQGRVT
ITADESTSTAYMELSSLRSEDTAVYYCARSHLLRASWFAYWGQGTLVTVSS

<SEQ ID NO:62>
DYYMK

<SEQ ID NO:63>
DIIPSFGATFYAQKFQG

<SEQ ID NO:64>
SHLLRASWFAY

<SEQ ID NO:65>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:66>
ESSQSLLNSGNQKNYLT

<SEQ ID NO:67>
WASTRES

<SEQ ID NO:68>
QNDYSYPYT
```

FIG. 1F

<SEQ ID NO:69>
QVQLVQSGAEVKKPGSSVKVSCKASGGTFSDYYMKWVRQAPGQGLEWMGDIIPSFGATFYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:70>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:71>
QVQLVQSGAEVKKPGSSVKVSCKASGGTFSDYYMKWVRQAPGQGLEWMGDIIPSNGTTFYAQKFQGRVT
ITADESTSTAYMELSSLRSEDTAVYYCARSHLLRASWFAYWGQGTLVTVSS

<SEQ ID NO:72>
DYYMK

<SEQ ID NO:73>
DIIPSNGTTFYAQKFQG

<SEQ ID NO:74>
SHLLRASWFAY

<SEQ ID NO:75>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:76>
ESSQSLLNSGNQKNYLT

<SEQ ID NO:77>
WASTRES

<SEQ ID NO:78>
QNDYSYPYT

<SEQ ID NO:79>
QVQLVQSGAEVKKPGSSVKVSCKASGGTFSDYYMKWVRQAPGQGLEWMGDIIPSNGTTFYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:80>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

FIG. 1G

<SEQ ID NO:81>
QVQLVQSGAEVKKPGSSVKVSCKASGGTFSDYYMKWVRQAPGQGLEWMGGIIPIFGTANYAQKFQGRVT
ITADESTSTAYMELSSLRSEDTAVYYCARSHLLRASWFAYWGQGTLVTVSS

<SEQ ID NO:82>
DYYMK

<SEQ ID NO:83>
GIIPIFGTANYAQKFQG

<SEQ ID NO:84>
SHLLRASWFAY

<SEQ ID NO:85>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:86>
ESSQSLLNSGNQKNYLT

<SEQ ID NO:87>
WASTRES

<SEQ ID NO:88>
QNDYSYPYT

<SEQ ID NO:89>
QVQLVQSGAEVKKPGSSVKVSCKASGGTFSDYYMKWVRQAPGQGLEWMGGIIPIFGTANYAQKFQGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:90>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:91>
QVQLQESGPGLVKPSETLSLTCTVSDGSISSGYYWNWIRQPPGKGLEWIGYISYDGSNNYNPSLKNRVT
ISVDTSKNQFSLKLSSVTAADTAVYYCARGEGFYFDYWGQGTLVTVSS

<SEQ ID NO:92>
SGYYWN

<SEQ ID NO:93>
YISYDGSNNYNPSLKN

<SEQ ID NO:94>
GEGFYFDY

FIG. 1H

<SEQ ID NO:95>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIK

<SEQ ID NO:96>
KSSQSLFFGSTQKNYLA

<SEQ ID NO:97>
WASTRES

<SEQ ID NO:98>
QQYYNYPWT

<SEQ ID NO:99>
QVQLQESGPGLVKPSETLSLTCTVSDGSISSGYYWNWIRQPPGKGLEWIGYISYDGSNNYNPSLKNRVT
ISVDTSKNQFSLKLSSVTAADTAVYYCARGEGFYFDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPG

<SEQ ID NO:100>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:101>
EVQLVQSGAEVKKPGESLKISCKGSDYSITSGYYWNWVRQMPGKGLEWMGYISYDGSNNYNPSLKNGQV
TISADKSISTAYLQWSSLKASDTAMYYCSRGEGFYFDSWGQGTLVTVSS

<SEQ ID NO:102>
SGYYWN

<SEQ ID NO:103>
YISYDGSNNYNPSLKNG

<SEQ ID NO:104>
GEGFYFDS

<SEQ ID NO:105>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIK

<SEQ ID NO:106>
KSSQSLFFGSTQKNYLA

<SEQ ID NO:107>
WASTRES

<SEQ ID NO:108>
QQYYNYPWT

FIG. 1I

<SEQ ID NO:109>
EVQLVQSGAEVKKPGESLKISCKGSDYSITSGYYWNWVRQMPGKGLEWMGYISYDGSNNYNPSLKNGQV
TISADKSISTAYLQWSSLKASDTAMYYCSRGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:110>
DIMMSQSPSSLAVSVGEKFTMTCKSSQSLFFGSTQKNYLAWYQQKPGQSPKLLIYWASTRESGVPDRFT
GSGSGTDFTLAISSVMPEDLAVYYCQQYYNYPWTFGGGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:111>
QVQLVQSGAEVKKPGSSVKVSCKASGGTFSDYYMKWVRQAPGQGLEWMGDIIPSNGATFYNQKFKGQVT
ITADESTSTAYMELSSLRSEDTAVYYCARSHLLRASWFAYWGQGTLVTVSS

<SEQ ID NO:112>
DYYMK

<SEQ ID NO:113>
DIIPSNGATFYNQKFKG

<SEQ ID NO:114>
SHLLRASWFAY

<SEQ ID NO:115>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:116>
ESSQSLLNSGNQKNYLT

<SEQ ID NO:117>
WASTRES

<SEQ ID NO:118>
QNDYSYPYT

<SEQ ID NO:119>
QVQLVQSGAEVKKPGSSVKVSCKASGGTFSDYYMKWVRQAPGQGLEWMGDIIPSNGATFYNQKFKGQVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:120>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

FIG. 1J

<SEQ ID NO:121>
QVQLVQSGAEVKKPGSSVKVSCKASGGTFSDYYMKWVRQAPGQGLEWMGDIIPSNGATFYNQKFKGQVT
ITADESTSTAYMELSSLRSEDTAVYYCARSHLLRASWFAYWGQGTLVTVSS

<SEQ ID NO:122>
DYYMK

<SEQ ID NO:123>
DIIPSNGATFYNQKFKG

<SEQ ID NO:124>
SHLLRASWFAY

<SEQ ID NO:125>
DIVMTQSPDSLAVSLGERATINCESSQSVLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:126>
ESSQSVLNSGNQKNYLT

<SEQ ID NO:127>
WASTRES

<SEQ ID NO:128>
QNDYSYPYT

<SEQ ID NO:129>
QVQLVQSGAEVKKPGSSVKVSCKASGGTFSDYYMKWVRQAPGQGLEWMGDIIPSNGATFYNQKFKGQVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:130>
DIVMTQSPDSLAVSLGERATINCESSQSVLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:131>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:132>
SGYYWN

<SEQ ID NO:133>
YISYDGSNNYNPSLKNG

<SEQ ID NO:134>
GEGFYFDS

FIG. 1K

<SEQ ID NO:135>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIK

<SEQ ID NO:136>
KSSQSLFFGSTQKNYLA

<SEQ ID NO:137>
WASTRES

<SEQ ID NO:138>
QQYYNYPWT

<SEQ ID NO:139>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:140>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:141>
EVQLLESGGGLVQPGGSLRLSCAVSDYSITSGYYSNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:142>
SGYYSN

<SEQ ID NO:143>
YISYDGSNNYNPSLKNG

<SEQ ID NO:144>
GEGFYFDS

<SEQ ID NO:145>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIK

<SEQ ID NO:146>
KSSQSLFFGSTQKNYLA

<SEQ ID NO:147>
WASTRES

<SEQ ID NO:148>
QQYYNYPWT

FIG. 1L

<SEQ ID NO:149>
EVQLLESGGGLVQPGGSLRLSCAVSDYSITSGYYSNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:150>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:151>
EVQLLESGGGLVQPGGSLRLSCAVSDYSITSGYYWNWIRQAPGKKLEWVGYISYDGSNNYNPSLKNGRI
TISRDTSKNTFYLQMNSLRAEDTAVYYCARGEGFYFDSWGQGTLVTVSS

<SEQ ID NO:152>
SGYYWN

<SEQ ID NO:153>
YISYDGSNNYNPSLKNG

<SEQ ID NO:154>
GEGFYFDS

<SEQ ID NO:155>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIK

<SEQ ID NO:156>
KSSQSLFFGSTQKNYLA

<SEQ ID NO:157>
WASTRES

<SEQ ID NO:158>
QQYYNYPWT

<SEQ ID NO:159>
EVQLLESGGGLVQPGGSLRLSCAVSDYSITSGYYWNWIRQAPGKKLEWVGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:160>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

FIG. 1M

<SEQ ID NO:161>
EVQLLESGGGLVQPGGSLRLSCAVSDYSITSNYYWNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:162>
SNYYWN

<SEQ ID NO:163>
YISYDGSNNYNPSLKNG

<SEQ ID NO:164>
GEGFYFDS

<SEQ ID NO:165>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIK

<SEQ ID NO:166>
KSSQSLFFGSTQKNYLA

<SEQ ID NO:167>
WASTRES

<SEQ ID NO:168>
QQYYNYPWT

<SEQ ID NO:169>
EVQLLESGGGLVQPGGSLRLSCAVSDYSITSNYYWNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:170>
EIVLTQSPGTLSLSPGERATLSCKSSQSLFFGSTQKNYLAWYQQKPGQAPRLLIYWASTRESGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:171>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:172>
SGYYWN

<SEQ ID NO:173>
YISYDGSNNYNPSLKNG

<SEQ ID NO:174>
GEGFYFDS

FIG. 1N

<SEQ ID NO:175>
EIVLTQSPGTLSLSPGERATLSCRASQSVSSSYLAWYQQKPGQAPRLLIYWASTRESGIPDRFSGSGSG
TDFTLTISRLEPEDFAVYYCQQYYNYPWTFGQGTKLEIK

<SEQ ID NO:176>
RASQSVSSSYLA

<SEQ ID NO:177>
WASTRES

<SEQ ID NO:178>
QQYYNYPWT

<SEQ ID NO:179>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:180>
EIVLTQSPGTLSLSPGERATLSCRASQSVSSSYLAWYQQKPGQAPRLLIYWASTRESGIPDRFSGSGSG
TDFTLTISRLEPEDFAVYYCQQYYNYPWTFGQGTKLEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSPVT
KSFNRGEC

<SEQ ID NO:181>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:182>
SGYYWN

<SEQ ID NO:183>
YISYDGSNNYNPSLKNG

<SEQ ID NO:184>
GEGFYFDS

<SEQ ID NO:185>
EIVLTQSPGTLSLSPGERATLSCKSSQSLFFGSTQKNYLAWYQQKPGQAPRLLIYGASSRATGIPDRFS
GSGSGTDFTLTISRLEPEDFAVYYCQQYYNYPWTFGQGTKLEIK

<SEQ ID NO:186>
KSSQSLFFGSTQKNYLA

<SEQ ID NO:187>
GASSRAT

<SEQ ID NO:188>
QQYYNYPWT

FIG. 1O

<SEQ ID NO:189>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:190>
EIVLTQSPGTLSLSPGERATLSCKSSQSLFFGSTQKNYLAWYQQKPGQAPRLLIYGASSRATGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:191>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSS

<SEQ ID NO:192>
SGYYWN

<SEQ ID NO:193>
YISYDGSNNYNPSLKNG

<SEQ ID NO:194>
GEGFYFDS

<SEQ ID NO:195>
EIVLTQSPGTLSLSPGERATLSCRASQSVFFGSTQKNYLAWYQQKPGQAPRLLIYWASTRESGIPDRFS
GSGSGTDFTLTISRLEPEDFAVYYCQQYYNYPWTFGQGTKLEIK

<SEQ ID NO:196>
RASQSVFFGSTQKNYLA

<SEQ ID NO:197>
WASTRES

<SEQ ID NO:198>
QQYYNYPWT

<SEQ ID NO:199>
EVQLLESGGGLVQPGGSLRLSCAVSDYSITSGYYWNWIRQAPGKKLEWMGYISYDGSNNYNPSLKNGRI
TISRDTSKNTFYLQMNSLRAEDTAVYYCARGEGFYFDSWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG

<SEQ ID NO:200>
EIVLTQSPGTLSLSPGERATLSCRASQSVFFGSTQKNYLAWYQQKPGQAPRLLIYWASTRESGIPDRFS
GSGSGTDFTLTISRLEPEDFAVYYCQQYYNYPWTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

FIG. 1P

<SEQ ID NO:201>
QVQLVQSGAEVKKPGSSVKVSCKASGGTFSDYYMKWVRQAPGQGLEWMGDIIPSNGATFYNQKFKGRVT
ITADESTSTAYMELSSLRSEDTAVYYCARSHLLRASWFAYWGQGTLVTVSS

<SEQ ID NO:202>
DYYMK

<SEQ ID NO:203>
DIIPSNGATFYNQKFKG

<SEQ ID NO:204>
SHLLRASWFAY

<SEQ ID NO:205>
DIVMTQSPDSLAVSLGERATINCESSQSVLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:206>
ESSQSVLNSGNQKNYLT

<SEQ ID NO:207>
WASTRES

<SEQ ID NO:208>
QNDYSYPYT

<SEQ ID NO:209>
QVQLVQSGAEVKKPGSSVKVSCKASGGTFSDYYMKWVRQAPGQGLEWMGDIIPSNGATFYNQKFKGRVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:210>
DIVMTQSPDSLAVSLGERATINCESSQSVLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:211>
QVQLVQSGAEVKKPGSSVKVSCKASGGTFSDYYMKWVRQAPGQGLEWMGDIIPSNGATFYNQKFQGQVT
ITADESTSTAYMELSSLRSEDTAVYYCARSHLLRASWFAYWGQGTLVTVSS

<SEQ ID NO:212>
DYYMK

<SEQ ID NO:213>
DIIPSNGATFYNQKFQG

<SEQ ID NO:214>
SHLLRASWFAY

FIG. 1Q

<SEQ ID NO:215>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIK

<SEQ ID NO:216>
ESSQSLLNSGNQKNYLT

<SEQ ID NO:217>
WASTRES

<SEQ ID NO:218>
QNDYSYPYT

<SEQ ID NO:219>
QVQLVQSGAEVKKPGSSVKVSCKASGGTFSDYYMKWVRQAPGQGLEWMGDIIPSNGATFYNQKFQGQVT
ITADESTSTAYMELSSLRSEDTAVYYCARSHLLRASWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPG

<SEQ ID NO:220>
DIVMTQSPDSLAVSLGERATINCESSQSLLNSGNQKNYLTWYQQKPGQPPKLLIYWASTRESGVPDRFS
GSGSGTDFTLTISSLQAEDVAVYYCQNDYSYPYTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGL
SSPVTKSFNRGEC

<SEQ ID NO:221>
KEDPNPPITNLRMKAKAQQLTWDLNRNVTDIECVKDADYSMPAVNNSYCQFGAISLCEVTNYTVRVANP
PFSTWILFPENSGKPWAGAENLTCWIHDVDFLSCSWAVGPGAPADVQYDLYLNVANRRQQYECLHYKTD
AQGTRIGCRFDDISRLSSGSQSSHILVRGRSAAFGIPCTDKFVVFSQIEILTPPNMTAKCNKTHSFMHW
KMRSHFNRKFRYELQIQKRMQPVITEQVRDRTSFQLLNPGTYTVQIRARERVYEFLSAWSTPQRFECDQ
EEGANTRAWRTSLLIALGTLLALVCVFVICRRYLVMQRLFPRIPHMKDPIGDSFQNDKLVVWEAGKAGL
EECLVTEVQVVQKT

FIG. 2A

>TPP-8987

>TPP-8987 VH
QVQLVQSGAEVKKPGSSVKVSCKASGGTFSDYYMKWVRQAPGQGLEWMGDIIPSNGATFYNQKFKGQVTITADESTSTAY
            |---|         |-----HCDR2-----|
            HCDR1

MELSSLRSEDTAVYYCARSHLLRASWFAYWGQGTLVTVSS
        |--HCDR3--|

>TPP-8987 VL
DIVMTQSPDSLAVSLGERATINCESSQSVLNSGNQKNYLTWYQQKPGQPPKLLIYWASTRESGVPDRFSGSGSGTDFTLT
             |-----LCDR1-----|         |-----|
                                        LCDR2

ISSLQAEDVAVYYCQNDYSYPYTFGQGTKLEIK
        |-LCDR3-|

>TPP-8987 Heavy Chain
QVQLVQSGAEVKKPGSSVKVSCKASGGTFSDYYMKWVRQAPGQGLEWMGDIIPSNGATFYNQKFKGQVTITADESTSTAY
|-------------------------------------------------------VH-------------------
            |---|         |-----HCDR2-----|
            HCDR1

MELSSLRSEDTAVYYCARSHLLRASWFAYWGQGTLVTVSSASTKGPSVFPLAPSSKSTSGGTAALGCLVKDYFPEPVTVS
-------------------------------------|
        |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-8987 Light Chain
DIVMTQSPDSLAVSLGERATINCESSQSVLNSGNQKNYLTWYQQKPGQPPKLLIYWASTRESGVPDRFSGSGSGTDFTLT
|-----------------------------------------------------VL----------------------
             |-----LCDR1-----|         |-----|
                                        LCDR2

ISSLQAEDVAVYYCQNDYSYPYTFGQGTKLEIKRTVAAPSVFIFPPSDEQLKSGTASVVCLLNNFYPREAKVQWKVDNAL
------------------------------|
        |-LCDR3-|

QSGNSQESVTEQDSKDSTYSLSSTLTLSKADYEKHKVYACEVTHQGLSSPVTKSFNRGEC

FIG. 2B

>TPP-8988

>TPP-8988 VH
EVQLLESGGGLVQPGGSLRLSCAVSDYSITSGYYWNWIRQAPGKKLEWMGYISYDGSNNYNPSLKNGRITISRDTSKNTF
            |----|         |-----HCDR2-----|
             HCDR1

YLQMNSLRAEDTAVYYCARGEGFYFDSWGQGTLVTVSS
            |------|
             HCDR3

>TPP-8988 VL
EIVLTQSPGTLSLSPGERATLSCKSSQSLFFGSTQKNYLAWYQQKPGQAPRLLIYWASTRESGIPDRFSGSGSGTDFTLT
            |-----LCDR1-----|         |-----|
                                         LCDR2

ISRLEPEDFAVYYCQQYYNYPWTFGQGTKLEIK
      |-LCDR3-|

>TPP-8988 Heavy Chain
EVQLLESGGGLVQPGGSLRLSCAVSDYSITSGYYWNWIRQAPGKKLEWMGYISYDGSNNYNPSLKNGRITISRDTSKNTF
|------------------------------------------------------VH--------------------
            |----|         |-----HCDR2-----|
             HCDR1

YLQMNSLRAEDTAVYYCARGEGFYFDSWGQGTLVTVSSASTKGPSVFPLAPSSKSTSGGTAALGCLVKDYFPEPVTVSWN
----------------------------------|
            |------|
             HCDR3

SGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

>TPP-8988 Light Chain
EIVLTQSPGTLSLSPGERATLSCKSSQSLFFGSTQKNYLAWYQQKPGQAPRLLIYWASTRESGIPDRFSGSGSGTDFTLT
|-----------------------------------------------------VL----------------------
            |-----LCDR1-----|         |-----|
                                         LCDR2

ISRLEPEDFAVYYCQQYYNYPWTFGQGTKLEIKRTVAAPSVFIFPPSDEQLKSGTASVVCLLNNFYPREAKVQWKVDNAL
------------------------------|
      |-LCDR3-|

QSGNSQESVTEQDSKDSTYSLSSTLTLSKADYEKHKVYACEVTHQGLSSPVTKSFNRGEC

FIG. 2C

>TPP-9476

>TPP-9476 VH
```
QVQLVQSGAEVKKPGSSVKVSCKASGGTFSDYYMKWVRQAPGQGLEWMGDIIPSNGATFYNQKFKGRVTITADESTSTAY
               |---|          |-----HCDR2-----|
                HCDR1

MELSSLRSEDTAVYYCARSHLLRASWFAYWGQGTLVTVSS
         |--HCDR3--|
```

>TPP-9476 VL
```
DIVMTQSPDSLAVSLGERATINCESSQSVLNSGNQKNYLTWYQQKPGQPPKLLIYWASTRESGVPDRFSGSGSGTDFTLT
             |-----LCDR1-----|         |-----|
                                         LCDR2

ISSLQAEDVAVYYCQNDYSYPYTFGQGTKLEIK
         |-LCDR3-|
```

>TPP-9476 Heavy Chain
```
QVQLVQSGAEVKKPGSSVKVSCKASGGTFSDYYMKWVRQAPGQGLEWMGDIIPSNGATFYNQKFKGRVTITADESTSTAY
|----------------------------------------------------------VH--------------------
               |---|          |-----HCDR2-----|
                HCDR1

MELSSLRSEDTAVYYCARSHLLRASWFAYWGQGTLVTVSSASTKGPSVFPLAPSSKSTSGGTAALGCLVKDYFPEPVTVS
-------------------------------------|
         |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

>TPP-9476 Light Chain
```
DIVMTQSPDSLAVSLGERATINCESSQSVLNSGNQKNYLTWYQQKPGQPPKLLIYWASTRESGVPDRFSGSGSGTDFTLT
|-----------------------------------------------------VL-----------------------
             |-----LCDR1-----|         |-----|
                                         LCDR2

ISSLQAEDVAVYYCQNDYSYPYTFGQGTKLEIKRTVAAPSVFIFPPSDEQLKSGTASVVCLLNNFYPREAKVQWKVDNAL
------------------------------|
         |-LCDR3-|

QSGNSQESVTEQDSKDSTYSLSSTLTLSKADYEKHKVYACEVTHQGLSSPVTKSFNRGEC
```

FIG. 2D

>TPP-9342

>TPP-9342 VH
EVQLLESGGGLVQPGGSLRLSCAVSDYSITSGYYWNWIRQAPGKKLEWMGYISYDGSNNYNPSLKNGRITISRDTSKNTF
                |----|          |-----HCDR2-----|
                 HCDR1

YLQMNSLRAEDTAVYYCARGEGFYFDSWGQGTLVTVSS
            |------|
             HCDR3

>TPP-9342 VL
EIVLTQSPGTLSLSPGERATLSCRASQSVFFGSTQKNYLAWYQQKPGQAPRLLIYWASTRESGIPDRFSGSGSGTDFTLT
             |-----LCDR1-----|         |-----|
                                          LCDR2

ISRLEPEDFAVYYCQQYYNYPWTFGQGTKLEIK
        |-LCDR3-|

>TPP-9342 Heavy Chain
EVQLLESGGGLVQPGGSLRLSCAVSDYSITSGYYWNWIRQAPGKKLEWMGYISYDGSNNYNPSLKNGRITISRDTSKNTF
|-------------------------------------------------------------VH--------------------
                |----|          |-----HCDR2-----|
                 HCDR1

YLQMNSLRAEDTAVYYCARGEGFYFDSWGQGTLVTVSSASTKGPSVFPLAPSSKSTSGGTAALGCLVKDYFPEPVTVSWN
----------------------------------|
            |------|
             HCDR3

SGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

>TPP-9342 Light Chain
EIVLTQSPGTLSLSPGERATLSCRASQSVFFGSTQKNYLAWYQQKPGQAPRLLIYWASTRESGIPDRFSGSGSGTDFTLT
|-------------------------------------------------------------VL----------------------
             |-----LCDR1-----|         |-----|
                                          LCDR2

ISRLEPEDFAVYYCQQYYNYPWTFGQGTKLEIKRTVAAPSVFIFPPSDEQLKSGTASVVCLLNNFYPREAKVQWKVDNAL
-----------------------------|
        |-LCDR3-|

QSGNSQESVTEQDSKDSTYSLSSTLTLSKADYEKHKVYACEVTHQGLSSPVTKSFNRGEC

```
                              SEQUENCE LISTING

<160> NUMBER OF SEQ ID NOS: 221

<210> SEQ ID NO 1
<211> LENGTH: 120
<212> TYPE: PRT
<213> ORGANISM: Artificial Sequence
<220> FEATURE:
<223> OTHER INFORMATION: Antibody Sequence

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: Antibody Sequence

<400> SEQUENCE: 2

Asp Tyr Tyr Met Lys
1               5
```

```
<210> SEQ ID NO 3
<211> LENGTH: 17
<212> TYPE: PRT
<213> ORGANISM: Artificial Sequence
<220> FEATURE:
<223> OTHER INFORMATION: Antibody Sequence

<400> SEQUENCE: 3

Asp Ile Ile Pro Ser Asn Gly Ala Thr Phe Tyr Asn Gln Lys Phe Lys
1               5                   10                  15
Gly

<210> SEQ ID NO 4
<211> LENGTH: 13
<212> TYPE: PRT
<213> ORGANISM: Artificial Sequence
<220> FEATURE:
<223> OTHER INFORMATION: Antibody Sequence

<400> SEQUENCE: 4

Ala Arg Ser His Leu Leu Arg Ala Ser Trp Phe Ala Tyr
1               5                   10

<210> SEQ ID NO 5
<211> LENGTH: 113
<212> TYPE: PRT
<213> ORGANISM: Artificial Sequence
<220> FEATURE:
<223> OTHER INFORMATION: Antibody Sequence

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 6
<211> LENGTH: 17
<212> TYPE: PRT
<213> ORGANISM: Artificial Sequence
<220> FEATURE:
<223> OTHER INFORMATION: Antibody Sequence

<400> SEQUENCE: 6

Glu Ser Ser Gln Ser Leu Leu Asn Ser Gly Asn Gln Lys Asn Tyr Leu
1               5                   10                  15

Thr

<210> SEQ ID NO 7
<211> LENGTH: 7
```

```
<212> TYPE: PRT
<213> ORGANISM: Artificial Sequence
<220> FEATURE:
<223> OTHER INFORMATION: Antibody Sequence

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody Sequence

<400> SEQUENCE: 8

Gln Asn Asp Tyr Ser Tyr Pro Tyr Thr
1               5

<210> SEQ ID NO 9
<211> LENGTH: 449
<212> TYPE: PRT
<213> ORGANISM: Artificial Sequence
<220> FEATURE:
<223> OTHER INFORMATION: Antibody Sequence

<400> SEQUENCE: 9

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 10
<211> LENGTH: 220
<212> TYPE: PRT
<213> ORGANISM: Artificial Sequence
<220> FEATURE:
<223> OTHER INFORMATION: Antibody Sequence

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 11
<211> LENGTH: 120
<212> TYPE: PRT
<213> ORGANISM: Artificial Sequence
<220> FEATURE:
<223> OTHER INFORMATION: Antibody Sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 12
<211> LENGTH: 5
<212> TYPE: PRT
<213> ORGANISM: Artificial Sequence
<220> FEATURE:
<223> OTHER INFORMATION: Antibody Sequence

<400> SEQUENCE: 12

Asp Tyr Tyr Met Lys
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody Sequence

<400> SEQUENCE: 13

Asp Ile Ile Pro Ser Asn Gly Ala Thr Phe Tyr Ala Gln Lys Phe Gln
1               5                   10                  15

Gly

<210> SEQ ID NO 14
<211> LENGTH: 11
<212> TYPE: PRT

```
<213> ORGANISM: Artificial Sequence
<220> FEATURE:
<223> OTHER INFORMATION: Antibody Sequence

<400> SEQUENCE: 14

Ser His Leu Leu Arg Ala Ser Trp Phe Ala Tyr
1               5                   10

<210> SEQ ID NO 15
<211> LENGTH: 113
<212> TYPE: PRT
<213> ORGANISM: Artificial Sequence
<220> FEATURE:
<223> OTHER INFORMATION: Antibody Sequence

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 16
<211> LENGTH: 17
<212> TYPE: PRT
<213> ORGANISM: Artificial Sequence
<220> FEATURE:
<223> OTHER INFORMATION: Antibody Sequence

<400> SEQUENCE: 16

Lys Ser Ser Gln Ser Leu Leu Asn Ser Gly Asn Gln Lys Asn Tyr Leu
1               5                   10                  15

Thr

<210> SEQ ID NO 17
<211> LENGTH: 7
<212> TYPE: PRT
<213> ORGANISM: Artificial Sequence
<220> FEATURE:
<223> OTHER INFORMATION: Antibody Sequence

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Antibody Sequence

<400> SEQUENCE: 18
```

Gln Asn Asp Tyr Ser Tyr Pro Tyr Thr
1               5

<210> SEQ ID NO 19
<211> LENGTH: 449
<212> TYPE: PRT
<213> ORGANISM: Artificial Sequence
<220> FEATURE:
<223> OTHER INFORMATION: Antibody Sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 20
<211> LENGTH: 220
<212> TYPE: PRT
<213> ORGANISM: Artificial Sequence
<220> FEATURE:
<223> OTHER INFORMATION: Antibody Sequence

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 120
<212> TYPE: PRT
<213> ORGANISM: Artificial Sequence
<220> FEATURE:
```

<223> OTHER INFORMATION: Antibody Sequence

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Asp Tyr
            20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
            115                 120

<210> SEQ ID NO 22
<211> LENGTH: 5
<212> TYPE: PRT
<213> ORGANISM: Artificial Sequence
<220> FEATURE:
<223> OTHER INFORMATION: Antibody Sequence

<400> SEQUENCE: 22

Asp Tyr Tyr Met Lys
1               5

<210> SEQ ID NO 23
<211> LENGTH: 17
<212> TYPE: PRT
<213> ORGANISM: Artificial Sequence
<220> FEATURE:
<223> OTHER INFORMATION: Antibody Sequence

<400> SEQUENCE: 23

Asp Ile Ile Pro Ser Asn Gly Ala Thr Phe Tyr Ala Gln Lys Phe Gln
1               5                   10                  15

Gly

<210> SEQ ID NO 24
<211> LENGTH: 11
<212> TYPE: PRT
<213> ORGANISM: Artificial Sequence
<220> FEATURE:
<223> OTHER INFORMATION: Antibody Sequence

<400> SEQUENCE: 24

Ser His Leu Leu Arg Ala Ser Trp Phe Ala Tyr
1               5                   10

<210> SEQ ID NO 25
<211> LENGTH: 113
<212> TYPE: PRT
<213> ORGANISM: Artificial Sequence
<220> FEATURE:
<223> OTHER INFORMATION: Antibody Sequence

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 26
<211> LENGTH: 17
<212> TYPE: PRT
<213> ORGANISM: Artificial Sequence
<220> FEATURE:
<223> OTHER INFORMATION: Antibody Sequence

<400> SEQUENCE: 26

Glu Ser Ser Gln Ser Leu Leu Asn Ser Gly Asn Gln Lys Asn Tyr Leu
1               5                   10                  15

Thr

<210> SEQ ID NO 27
<211> LENGTH: 7
<212> TYPE: PRT
<213> ORGANISM: Artificial Sequence
<220> FEATURE:
<223> OTHER INFORMATION: Antibody Sequence

<400> SEQUENCE: 27

Trp Ala Ser Thr Arg Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Antibody Sequence

<400> SEQUENCE: 28

Gln Asn Asp Tyr Ser Tyr Pro Tyr Thr
1               5

<210> SEQ ID NO 29
<211> LENGTH: 449
<212> TYPE: PRT
<213> ORGANISM: Artificial Sequence
<220> FEATURE:
<223> OTHER INFORMATION: Antibody Sequence

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

```
Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 30
<211> LENGTH: 220
<212> TYPE: PRT
<213> ORGANISM: Artificial Sequence
<220> FEATURE:
<223> OTHER INFORMATION: Antibody Sequence

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 31
<211> LENGTH: 120
<212> TYPE: PRT
<213> ORGANISM: Artificial Sequence
<220> FEATURE:
<223> OTHER INFORMATION: Antibody Sequence

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
             85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 32
<211> LENGTH: 5
<212> TYPE: PRT
<213> ORGANISM: Artificial Sequence
<220> FEATURE:
<223> OTHER INFORMATION: Antibody Sequence

<400> SEQUENCE: 32

Asp Tyr Tyr Met Lys
1               5

<210> SEQ ID NO 33
<211> LENGTH: 17
<212> TYPE: PRT
<213> ORGANISM: Artificial Sequence
<220> FEATURE:
<223> OTHER INFORMATION: Antibody Sequence

<400> SEQUENCE: 33

Asp Ile Ile Pro Ser Asn Gly Ala Thr Phe Tyr Ala Gln Lys Phe Gln
1               5                   10                  15

Gly

<210> SEQ ID NO 34
<211> LENGTH: 11
<212> TYPE: PRT
<213> ORGANISM: Artificial Sequence
<220> FEATURE:
<223> OTHER INFORMATION: Antibody Sequence

<400> SEQUENCE: 34

Ser His Leu Leu Arg Ala Ser Trp Phe Ala Tyr
1               5                   10

<210> SEQ ID NO 35
<211> LENGTH: 113
<212> TYPE: PRT
<213> ORGANISM: Artificial Sequence
<220> FEATURE:
<223> OTHER INFORMATION: Antibody Sequence

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
```

```
                100             105             110
Lys

<210> SEQ ID NO 36
<211> LENGTH: 17
<212> TYPE: PRT
<213> ORGANISM: Artificial Sequence
<220> FEATURE:
<223> OTHER INFORMATION: Antibody Sequence

<400> SEQUENCE: 36

Lys Ser Ser Gln Ser Leu Leu Asn Ser Gly Asn Gln Lys Asn Tyr Leu
1               5                   10                  15
Thr

<210> SEQ ID NO 37
<211> LENGTH: 7
<212> TYPE: PRT
<213> ORGANISM: Artificial Sequence
<220> FEATURE:
<223> OTHER INFORMATION: Antibody Sequence

<400> SEQUENCE: 37

Trp Ala Ser Thr Arg Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Antibody Sequence

<400> SEQUENCE: 38

Gln Asn Asp Tyr Ser Tyr Pro Tyr Thr
1               5

<210> SEQ ID NO 39
<211> LENGTH: 449
<212> TYPE: PRT
<213> ORGANISM: Artificial Sequence
<220> FEATURE:
<223> OTHER INFORMATION: Antibody Sequence

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125
```

```
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 40
<211> LENGTH: 220
<212> TYPE: PRT
<213> ORGANISM: Artificial Sequence
<220> FEATURE:
<223> OTHER INFORMATION: Antibody Sequence

<400> SEQUENCE: 40

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
```

```
              35                  40                  45
Pro Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Asn
                 85                  90                  95
Asp Tyr Ser Tyr Pro Tyr Thr Phe Gly Gln Gly Thr Lys Leu Glu Ile
                100                 105                 110
Lys Arg Thr Val Ala Ala Pro Ser Val Phe Ile Phe Pro Pro Ser Asp
                115                 120                 125
Glu Gln Leu Lys Ser Gly Thr Ala Ser Val Val Cys Leu Leu Asn Asn
                130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
                180                 185                 190
Glu Lys His Lys Val Tyr Ala Cys Glu Val Thr His Gln Gly Leu Ser
                195                 200                 205
Ser Pro Val Thr Lys Ser Phe Asn Arg Gly Glu Cys
                210                 215                 220

<210> SEQ ID NO 41
<211> LENGTH: 117
<212> TYPE: PRT
<213> ORGANISM: Artificial Sequence
<220> FEATURE:
<223> OTHER INFORMATION: Antibody Sequence

<400> SEQUENCE: 41

Gln Val Gln Leu Gln Glu Ser Gly Pro Gly Leu Val Lys Pro Ser Gln
  1               5                  10                  15
Ser Leu Ser Leu Thr Cys Ser Val Thr Asp Tyr Ser Ile Thr Ser Gly
                 20                  25                  30
Tyr Tyr Trp Asn Trp Ile Arg Gln Phe Pro Gly Asn Lys Leu Glu Trp
                 35                  40                  45
Met Gly Tyr Ile Ser Tyr Asp Gly Ser Asn Asn Tyr Asn Pro Ser Leu
 50                  55                  60
Lys Asn Arg Ile Ser Ile Thr Arg Asp Thr Ser Lys Asn Gln Phe Phe
 65                  70                  75                  80
Leu Lys Leu Ser Ser Val Thr Thr Glu Asp Thr Ala Thr Tyr Tyr Cys
                 85                  90                  95
Ser Arg Gly Glu Gly Phe Tyr Phe Asp Ser Trp Gly Gln Gly Thr Thr
                100                 105                 110
Leu Thr Val Ser Ser
                115

<210> SEQ ID NO 42
<211> LENGTH: 6
<212> TYPE: PRT
<213> ORGANISM: Artificial Sequence
<220> FEATURE:
<223> OTHER INFORMATION: Antibody Sequence

<400> SEQUENCE: 42
```

Ser Gly Tyr Tyr Trp Asn
1               5

<210> SEQ ID NO 43
<211> LENGTH: 16
<212> TYPE: PRT
<213> ORGANISM: Artificial Sequence
<220> FEATURE:
<223> OTHER INFORMATION: Antibody Sequence

<400> SEQUENCE: 43

Tyr Ile Ser Tyr Asp Gly Ser Asn Asn Tyr Asn Pro Ser Leu Lys Asn
1               5                   10                  15

<210> SEQ ID NO 44
<211> LENGTH: 8
<212> TYPE: PRT
<213> ORGANISM: Artificial Sequence
<220> FEATURE:
<223> OTHER INFORMATION: Antibody Sequence

<400> SEQUENCE: 44

Gly Glu Gly Phe Tyr Phe Asp Ser
1               5

<210> SEQ ID NO 45
<211> LENGTH: 113
<212> TYPE: PRT
<213> ORGANISM: Artificial Sequence
<220> FEATURE:
<223> OTHER INFORMATION: Antibody Sequence

<400> SEQUENCE: 45

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
                20                  25                  30

Ser Thr Gln Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
                100                 105                 110

Lys

<210> SEQ ID NO 46
<211> LENGTH: 17
<212> TYPE: PRT
<213> ORGANISM: Artificial Sequence
<220> FEATURE:
<223> OTHER INFORMATION: Antibody Sequence

<400> SEQUENCE: 46

Lys Ser Ser Gln Ser Leu Phe Phe Gly Ser Thr Gln Lys Asn Tyr Leu
1               5                   10                  15

Ala

<210> SEQ ID NO 47

```
<211> LENGTH: 7
<212> TYPE: PRT
<213> ORGANISM: Artificial Sequence
<220> FEATURE:
<223> OTHER INFORMATION: Antibody Sequence

<400> SEQUENCE: 47

Trp Ala Ser Thr Arg Glu Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Antibody Sequence

<400> SEQUENCE: 48

Gln Gln Tyr Tyr Asn Tyr Pro Trp Thr
1               5

<210> SEQ ID NO 49
<211> LENGTH: 446
<212> TYPE: PRT
<213> ORGANISM: Artificial Sequence
<220> FEATURE:
<223> OTHER INFORMATION: Antibody Sequence

<400> SEQUENCE: 49

Gln Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Ser Ser Val Thr Thr Glu Asp Thr Ala Thr Tyr Tyr Cys
                85                  90                  95

Ser Arg Gly Glu Gly Phe Tyr Phe Asp Ser Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 50
<211> LENGTH: 220
<212> TYPE: PRT
<213> ORGANISM: Artificial Sequence
<220> FEATURE:
<223> OTHER INFORMATION: Antibody Sequence

<400> SEQUENCE: 50

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 51
<211> LENGTH: 120
<212> TYPE: PRT
<213> ORGANISM: Artificial Sequence
<220> FEATURE:
<223> OTHER INFORMATION: Antibody Sequence

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Gly Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 52
<211> LENGTH: 5
<212> TYPE: PRT
<213> ORGANISM: Artificial Sequence
<220> FEATURE:
<223> OTHER INFORMATION: Antibody Sequence

<400> SEQUENCE: 52

Asp Tyr Tyr Met Lys
1               5

<210> SEQ ID NO 53
<211> LENGTH: 17
<212> TYPE: PRT
<213> ORGANISM: Artificial Sequence
<220> FEATURE:
<223> OTHER INFORMATION: Antibody Sequence

<400> SEQUENCE: 53

Gly Ile Ile Pro Ser Asn Gly Ala Thr Phe Tyr Ala Gln Lys Phe Gln
1               5                   10                  15

Gly

<210> SEQ ID NO 54
<211> LENGTH: 11
<212> TYPE: PRT
<213> ORGANISM: Artificial Sequence

```
<220> FEATURE:
<223> OTHER INFORMATION: Antibody Sequence

<400> SEQUENCE: 54

Ser His Leu Leu Arg Ala Ser Trp Phe Ala Tyr
1               5                   10

<210> SEQ ID NO 55
<211> LENGTH: 113
<212> TYPE: PRT
<213> ORGANISM: Artificial Sequence
<220> FEATURE:
<223> OTHER INFORMATION: Antibody Sequence

<400> SEQUENCE: 55

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 56
<211> LENGTH: 17
<212> TYPE: PRT
<213> ORGANISM: Artificial Sequence
<220> FEATURE:
<223> OTHER INFORMATION: Antibody Sequence

<400> SEQUENCE: 56

Glu Ser Ser Gln Ser Leu Leu Asn Ser Gly Asn Gln Lys Asn Tyr Leu
1               5                   10                  15

Thr

<210> SEQ ID NO 57
<211> LENGTH: 7
<212> TYPE: PRT
<213> ORGANISM: Artificial Sequence
<220> FEATURE:
<223> OTHER INFORMATION: Antibody Sequence

<400> SEQUENCE: 57

Trp Ala Ser Thr Arg Glu Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Antibody Sequence

<400> SEQUENCE: 58
```

Gln Asn Asp Tyr Ser Tyr Pro Tyr Thr
1               5

<210> SEQ ID NO 59
<211> LENGTH: 449
<212> TYPE: PRT
<213> ORGANISM: Artificial Sequence
<220> FEATURE:
<223> OTHER INFORMATION: Antibody Sequence

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Gly Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 60
<211> LENGTH: 220
<212> TYPE: PRT
<213> ORGANISM: Artificial Sequence
<220> FEATURE:
<223> OTHER INFORMATION: Antibody Sequence

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 61
<211> LENGTH: 120
<212> TYPE: PRT
<213> ORGANISM: Artificial Sequence
<220> FEATURE:
<223> OTHER INFORMATION: Antibody Sequence

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Phe Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 62
<211> LENGTH: 5
<212> TYPE: PRT
<213> ORGANISM: Artificial Sequence
<220> FEATURE:
<223> OTHER INFORMATION: Antibody Sequence

<400> SEQUENCE: 62

Asp Tyr Tyr Met Lys
1               5

<210> SEQ ID NO 63
<211> LENGTH: 17
<212> TYPE: PRT
<213> ORGANISM: Artificial Sequence
<220> FEATURE:
<223> OTHER INFORMATION: Antibody Sequence

<400> SEQUENCE: 63

Asp Ile Ile Pro Ser Phe Gly Ala Thr Phe Tyr Ala Gln Lys Phe Gln
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: Antibody Sequence

<400> SEQUENCE: 64

Ser His Leu Leu Arg Ala Ser Trp Phe Ala Tyr
1               5                   10

<210> SEQ ID NO 65
<211> LENGTH: 113
<212> TYPE: PRT
<213> ORGANISM: Artificial Sequence
<220> FEATURE:
<223> OTHER INFORMATION: Antibody Sequence

<400> SEQUENCE: 65

Asp Ile Val Met Thr Gln Ser Pro Asp Ser Leu Ala Val Ser Leu Gly

```
                1               5                  10                  15
            Glu Arg Ala Thr Ile Asn Cys Glu Ser Ser Gln Ser Leu Leu Asn Ser
                            20                  25                  30

Gly Asn Gln Lys Asn Tyr Leu Thr Trp Tyr Gln Gln Lys Pro Gly Gln
                        35                  40                  45

Pro Pro Lys Leu Leu Ile Tyr Trp Ala Ser Thr Arg Glu Ser Gly Val
                    50                  55                  60

Pro Asp Arg Phe Ser Gly Ser Gly Ser Gly Thr Asp Phe Thr Leu Thr
            65                  70                  75                  80

Ile Ser Ser Leu Gln Ala Glu Asp Val Ala Val Tyr Tyr Cys Gln Asn
                            85                  90                  95

Asp Tyr Ser Tyr Pro Tyr Thr Phe Gly Gln Gly Thr Lys Leu Glu Ile
                        100                 105                 110

Lys

<210> SEQ ID NO 66
            <211> LENGTH: 17
            <212> TYPE: PRT
            <213> ORGANISM: Artificial Sequence
            <220> FEATURE:
            <223> OTHER INFORMATION: Antibody Sequence

<400> SEQUENCE: 66

Glu Ser Ser Gln Ser Leu Leu Asn Ser Gly Asn Gln Lys Asn Tyr Leu
            1               5                   10                  15

Thr

<210> SEQ ID NO 67
            <211> LENGTH: 7
            <212> TYPE: PRT
            <213> ORGANISM: Artificial Sequence
            <220> FEATURE:
            <223> OTHER INFORMATION: Antibody Sequence

<400> SEQUENCE: 67

Trp Ala Ser Thr Arg Glu Ser
            1               5

<210> SEQ ID NO 68
            <211> LENGTH: 9
            <212> TYPE: PRT
            <213> ORGANISM: Artificial Sequence
            <220> FEATURE:
            <223> OTHER INFORMATION: Antibody Sequence

<400> SEQUENCE: 68

Gln Asn Asp Tyr Ser Tyr Pro Tyr Thr
            1               5

<210> SEQ ID NO 69
            <211> LENGTH: 449
            <212> TYPE: PRT
            <213> ORGANISM: Artificial Sequence
            <220> FEATURE:
            <223> OTHER INFORMATION: Antibody Sequence

<400> SEQUENCE: 69

Gln Val Gln Leu Val Gln Ser Gly Ala Glu Val Lys Lys Pro Gly Ser
            1               5                   10                  15

Ser Val Lys Val Ser Cys Lys Ala Ser Gly Gly Thr Phe Ser Asp Tyr
                            20                  25                  30
```

-continued

```
Tyr Met Lys Trp Val Arg Gln Ala Pro Gly Gln Gly Leu Glu Trp Met
         35                  40                  45
Gly Asp Ile Ile Pro Ser Phe Gly Ala Thr Phe Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser His Leu Leu Arg Ala Ser Trp Phe Ala Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly
```

<210> SEQ ID NO 70
<211> LENGTH: 220
<212> TYPE: PRT
<213> ORGANISM: Artificial Sequence
<220> FEATURE:
<223> OTHER INFORMATION: Antibody Sequence

<400> SEQUENCE: 70

```
Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 71
<211> LENGTH: 120
<212> TYPE: PRT
<213> ORGANISM: Artificial Sequence
<220> FEATURE:
<223> OTHER INFORMATION: Antibody Sequence

<400> SEQUENCE: 71

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Thr Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Ser His Leu Leu Arg Ala Ser Trp Phe Ala Tyr Trp Gly Gln
                100                 105                 110

Gly Thr Leu Val Thr Val Ser Ser
            115                 120

<210> SEQ ID NO 72
<211> LENGTH: 5
<212> TYPE: PRT
<213> ORGANISM: Artificial Sequence
<220> FEATURE:
<223> OTHER INFORMATION: Antibody Sequence

<400> SEQUENCE: 72

Asp Tyr Tyr Met Lys
1               5

<210> SEQ ID NO 73
<211> LENGTH: 17
<212> TYPE: PRT
<213> ORGANISM: Artificial Sequence
<220> FEATURE:
<223> OTHER INFORMATION: Antibody Sequence

<400> SEQUENCE: 73

Asp Ile Ile Pro Ser Asn Gly Thr Thr Phe Tyr Ala Gln Lys Phe Gln
1               5                   10                  15

Gly

<210> SEQ ID NO 74
<211> LENGTH: 11
<212> TYPE: PRT
<213> ORGANISM: Artificial Sequence
<220> FEATURE:
<223> OTHER INFORMATION: Antibody Sequence

<400> SEQUENCE: 74

Ser His Leu Leu Arg Ala Ser Trp Phe Ala Tyr
1               5                   10

<210> SEQ ID NO 75
<211> LENGTH: 113
<212> TYPE: PRT
<213> ORGANISM: Artificial Sequence
<220> FEATURE:
<223> OTHER INFORMATION: Antibody Sequence

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
```

Lys

<210> SEQ ID NO 76
<211> LENGTH: 17
<212> TYPE: PRT
<213> ORGANISM: Artificial Sequence
<220> FEATURE:
<223> OTHER INFORMATION: Antibody Sequence

<400> SEQUENCE: 76

Glu Ser Ser Gln Ser Leu Leu Asn Ser Gly Asn Gln Lys Asn Tyr Leu
1               5                   10                  15
Thr

<210> SEQ ID NO 77
<211> LENGTH: 7
<212> TYPE: PRT
<213> ORGANISM: Artificial Sequence
<220> FEATURE:
<223> OTHER INFORMATION: Antibody Sequence

<400> SEQUENCE: 77

Trp Ala Ser Thr Arg Glu Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Antibody Sequence

<400> SEQUENCE: 78

Gln Asn Asp Tyr Ser Tyr Pro Tyr Thr
1               5

<210> SEQ ID NO 79
<211> LENGTH: 449
<212> TYPE: PRT
<213> ORGANISM: Artificial Sequence
<220> FEATURE:
<223> OTHER INFORMATION: Antibody Sequence

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Thr Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 80
<211> LENGTH: 220
<212> TYPE: PRT
<213> ORGANISM: Artificial Sequence
<220> FEATURE:
<223> OTHER INFORMATION: Antibody Sequence

<400> SEQUENCE: 80

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45
```

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 81
<211> LENGTH: 120
<212> TYPE: PRT
<213> ORGANISM: Artificial Sequence
<220> FEATURE:
<223> OTHER INFORMATION: Antibody Sequence

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 82
<211> LENGTH: 5
<212> TYPE: PRT
<213> ORGANISM: Artificial Sequence
<220> FEATURE:
<223> OTHER INFORMATION: Antibody Sequence

<400> SEQUENCE: 82

Asp Tyr Tyr Met Lys

<210> SEQ ID NO 83
<211> LENGTH: 17
<212> TYPE: PRT
<213> ORGANISM: Artificial Sequence
<220> FEATURE:
<223> OTHER INFORMATION: Antibody Sequence

<400> SEQUENCE: 83

Gly Ile Ile Pro Ile Phe Gly Thr Ala Asn Tyr Ala Gln Lys Phe Gln
1               5                   10                  15
Gly

<210> SEQ ID NO 84
<211> LENGTH: 11
<212> TYPE: PRT
<213> ORGANISM: Artificial Sequence
<220> FEATURE:
<223> OTHER INFORMATION: Antibody Sequence

<400> SEQUENCE: 84

Ser His Leu Leu Arg Ala Ser Trp Phe Ala Tyr
1               5                   10

<210> SEQ ID NO 85
<211> LENGTH: 113
<212> TYPE: PRT
<213> ORGANISM: Artificial Sequence
<220> FEATURE:
<223> OTHER INFORMATION: Antibody Sequence

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
Lys

<210> SEQ ID NO 86
<211> LENGTH: 17
<212> TYPE: PRT
<213> ORGANISM: Artificial Sequence
<220> FEATURE:
<223> OTHER INFORMATION: Antibody Sequence

<400> SEQUENCE: 86

Glu Ser Ser Gln Ser Leu Leu Asn Ser Gly Asn Gln Lys Asn Tyr Leu
1               5                   10                  15
Thr

```
<210> SEQ ID NO 87
<211> LENGTH: 7
<212> TYPE: PRT
<213> ORGANISM: Artificial Sequence
<220> FEATURE:
<223> OTHER INFORMATION: Antibody Sequence

<400> SEQUENCE: 87

Trp Ala Ser Thr Arg Glu Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Antibody Sequence

<400> SEQUENCE: 88

Gln Asn Asp Tyr Ser Tyr Pro Tyr Thr
1               5

<210> SEQ ID NO 89
<211> LENGTH: 449
<212> TYPE: PRT
<213> ORGANISM: Artificial Sequence
<220> FEATURE:
<223> OTHER INFORMATION: Antibody Sequence

<400> SEQUENCE: 89
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 90
<211> LENGTH: 220
<212> TYPE: PRT
<213> ORGANISM: Artificial Sequence
<220> FEATURE:
<223> OTHER INFORMATION: Antibody Sequence

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 91
<211> LENGTH: 117
<212> TYPE: PRT
<213> ORGANISM: Artificial Sequence
<220> FEATURE:
<223> OTHER INFORMATION: Antibody Sequence

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Ile Ser Ser Gly
            20                  25                  30

Tyr Tyr Trp Asn Trp Ile Arg Gln Pro Pro Gly Lys Gly Leu Glu Trp
        35                  40                  45

Ile Gly Tyr Ile Ser Tyr Asp Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Glu Gly Phe Tyr Phe Asp Tyr Trp Gly Gln Gly Thr Leu
            100                 105                 110

Val Thr Val Ser Ser
        115

<210> SEQ ID NO 92
<211> LENGTH: 6
<212> TYPE: PRT
<213> ORGANISM: Artificial Sequence
<220> FEATURE:
<223> OTHER INFORMATION: Antibody Sequence

<400> SEQUENCE: 92

Ser Gly Tyr Tyr Trp Asn
1               5

<210> SEQ ID NO 93
<211> LENGTH: 16
<212> TYPE: PRT
<213> ORGANISM: Artificial Sequence
<220> FEATURE:
<223> OTHER INFORMATION: Antibody Sequence

<400> SEQUENCE: 93

Tyr Ile Ser Tyr Asp Gly Ser Asn Asn Tyr Asn Pro Ser Leu Lys Asn
1               5                   10                  15

<210> SEQ ID NO 94
<211> LENGTH: 8
<212> TYPE: PRT
```

<213> ORGANISM: Artificial Sequence
<220> FEATURE:
<223> OTHER INFORMATION: Antibody Sequence

<400> SEQUENCE: 94

Gly Glu Gly Phe Tyr Phe Asp Tyr
1               5

<210> SEQ ID NO 95
<211> LENGTH: 113
<212> TYPE: PRT
<213> ORGANISM: Artificial Sequence
<220> FEATURE:
<223> OTHER INFORMATION: Antibody Sequence

<400> SEQUENCE: 95

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys

<210> SEQ ID NO 96
<211> LENGTH: 17
<212> TYPE: PRT
<213> ORGANISM: Artificial Sequence
<220> FEATURE:
<223> OTHER INFORMATION: Antibody Sequence

<400> SEQUENCE: 96

Lys Ser Ser Gln Ser Leu Phe Phe Gly Ser Thr Gln Lys Asn Tyr Leu
1               5                   10                  15

Ala

<210> SEQ ID NO 97
<211> LENGTH: 7
<212> TYPE: PRT
<213> ORGANISM: Artificial Sequence
<220> FEATURE:
<223> OTHER INFORMATION: Antibody Sequence

<400> SEQUENCE: 97

Trp Ala Ser Thr Arg Glu Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Antibody Sequence

<400> SEQUENCE: 98

Gln Gln Tyr Tyr Asn Tyr Pro Trp Thr
1               5

<210> SEQ ID NO 99
<211> LENGTH: 446
<212> TYPE: PRT
<213> ORGANISM: Artificial Sequence
<220> FEATURE:
<223> OTHER INFORMATION: Antibody Sequence

<400> SEQUENCE: 99

Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Ile Ser Ser Gly
            20                  25                  30

Tyr Tyr Trp Asn Trp Ile Arg Gln Pro Pro Gly Lys Gly Leu Glu Trp
        35                  40                  45

Ile Gly Tyr Ile Ser Tyr Asp Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Glu Gly Phe Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 100
<211> LENGTH: 220
<212> TYPE: PRT
<213> ORGANISM: Artificial Sequence
<220> FEATURE:
<223> OTHER INFORMATION: Antibody Sequence

<400> SEQUENCE: 100

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 101
<211> LENGTH: 118
<212> TYPE: PRT
<213> ORGANISM: Artificial Sequence
<220> FEATURE:
<223> OTHER INFORMATION: Antibody Sequence
```

<400> SEQUENCE: 101

Glu Val Gln Leu Val Gln Ser Gly Ala Glu Val Lys Lys Pro Gly Glu
1               5                   10                  15

Ser Leu Lys Ile Ser Cys Lys Gly Ser Asp Tyr Ser Ile Thr Ser Gly
            20                  25                  30

Tyr Tyr Trp Asn Trp Val Arg Gln Met Pro Gly Lys Gly Leu Glu Trp
        35                  40                  45

Met Gly Tyr Ile Ser Tyr Asp Gly Ser Asn Asn Tyr Asn Pro Ser Leu
    50                  55                  60

Lys Asn Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ser Arg Gly Glu Gly Phe Tyr Phe Asp Ser Trp Gly Gln Gly Thr
            100                 105                 110

Leu Val Thr Val Ser Ser
        115

<210> SEQ ID NO 102
<211> LENGTH: 6
<212> TYPE: PRT
<213> ORGANISM: Artificial Sequence
<220> FEATURE:
<223> OTHER INFORMATION: Antibody Sequence

<400> SEQUENCE: 102

Ser Gly Tyr Tyr Trp Asn
1               5

<210> SEQ ID NO 103
<211> LENGTH: 17
<212> TYPE: PRT
<213> ORGANISM: Artificial Sequence
<220> FEATURE:
<223> OTHER INFORMATION: Antibody Sequence

<400> SEQUENCE: 103

Tyr Ile Ser Tyr Asp Gly Ser Asn Asn Tyr Asn Pro Ser Leu Lys Asn
1               5                   10                  15

Gly

<210> SEQ ID NO 104
<211> LENGTH: 8
<212> TYPE: PRT
<213> ORGANISM: Artificial Sequence
<220> FEATURE:
<223> OTHER INFORMATION: Antibody Sequence

<400> SEQUENCE: 104

Gly Glu Gly Phe Tyr Phe Asp Ser
1               5

<210> SEQ ID NO 105
<211> LENGTH: 113
<212> TYPE: PRT
<213> ORGANISM: Artificial Sequence
<220> FEATURE:
<223> OTHER INFORMATION: Antibody Sequence

<400> SEQUENCE: 105

Asp Ile Met Met Ser Gln Ser Pro Ser Ser Leu Ala Val Ser Val Gly
1               5                   10                  15

```
Glu Lys Phe Thr Met Thr Cys Lys Ser Ser Gln Ser Leu Phe Phe Gly
                20                  25                  30

Ser Thr Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
                100                 105                 110

Lys

<210> SEQ ID NO 106
<211> LENGTH: 17
<212> TYPE: PRT
<213> ORGANISM: Artificial Sequence
<220> FEATURE:
<223> OTHER INFORMATION: Antibody Sequence

<400> SEQUENCE: 106

Lys Ser Ser Gln Ser Leu Phe Phe Gly Ser Thr Gln Lys Asn Tyr Leu
1               5                   10                  15

Ala

<210> SEQ ID NO 107
<211> LENGTH: 7
<212> TYPE: PRT
<213> ORGANISM: Artificial Sequence
<220> FEATURE:
<223> OTHER INFORMATION: Antibody Sequence

<400> SEQUENCE: 107

Trp Ala Ser Thr Arg Glu Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Antibody Sequence

<400> SEQUENCE: 108

Gln Gln Tyr Tyr Asn Tyr Pro Trp Thr
1               5

<210> SEQ ID NO 109
<211> LENGTH: 447
<212> TYPE: PRT
<213> ORGANISM: Artificial Sequence
<220> FEATURE:
<223> OTHER INFORMATION: Antibody Sequence

<400> SEQUENCE: 109

Glu Val Gln Leu Val Gln Ser Gly Ala Glu Val Lys Lys Pro Gly Glu
1               5                   10                  15

Ser Leu Lys Ile Ser Cys Lys Gly Ser Asp Tyr Ser Ile Thr Ser Gly
                20                  25                  30

Tyr Tyr Trp Asn Trp Val Arg Gln Met Pro Gly Lys Gly Leu Glu Trp
```

```
                35                  40                  45
Met Gly Tyr Ile Ser Tyr Asp Gly Ser Asn Tyr Asn Pro Ser Leu
 50                  55                  60

Lys Asn Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ser Arg Gly Glu Gly Phe Tyr Phe Asp Ser Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 110
```

<211> LENGTH: 220
<212> TYPE: PRT
<213> ORGANISM: Artificial Sequence
<220> FEATURE:
<223> OTHER INFORMATION: Antibody Sequence

<400> SEQUENCE: 110

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 111
<211> LENGTH: 120
<212> TYPE: PRT
<213> ORGANISM: Artificial Sequence
<220> FEATURE:
<223> OTHER INFORMATION: Antibody Sequence

<400> SEQUENCE: 111

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln

```
                      100                 105                 110

Gly Thr Leu Val Thr Val Ser Ser
        115                 120

<210> SEQ ID NO 112
<211> LENGTH: 5
<212> TYPE: PRT
<213> ORGANISM: Artificial Sequence
<220> FEATURE:
<223> OTHER INFORMATION: Antibody Sequence

<400> SEQUENCE: 112

Asp Tyr Tyr Met Lys
1               5

<210> SEQ ID NO 113
<211> LENGTH: 17
<212> TYPE: PRT
<213> ORGANISM: Artificial Sequence
<220> FEATURE:
<223> OTHER INFORMATION: Antibody Sequence

<400> SEQUENCE: 113

Asp Ile Ile Pro Ser Asn Gly Ala Thr Phe Tyr Asn Gln Lys Phe Lys
1               5                   10                  15

Gly

<210> SEQ ID NO 114
<211> LENGTH: 11
<212> TYPE: PRT
<213> ORGANISM: Artificial Sequence
<220> FEATURE:
<223> OTHER INFORMATION: Antibody Sequence

<400> SEQUENCE: 114

Ser His Leu Leu Arg Ala Ser Trp Phe Ala Tyr
1               5                   10

<210> SEQ ID NO 115
<211> LENGTH: 113
<212> TYPE: PRT
<213> ORGANISM: Artificial Sequence
<220> FEATURE:
<223> OTHER INFORMATION: Antibody Sequence

<400> SEQUENCE: 115

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys
```

<210> SEQ ID NO 116
<211> LENGTH: 17
<212> TYPE: PRT
<213> ORGANISM: Artificial Sequence
<220> FEATURE:
<223> OTHER INFORMATION: Antibody Sequence

<400> SEQUENCE: 116

Glu Ser Ser Gln Ser Leu Leu Asn Ser Gly Asn Gln Lys Asn Tyr Leu
1               5                   10                  15

Thr

<210> SEQ ID NO 117
<211> LENGTH: 7
<212> TYPE: PRT
<213> ORGANISM: Artificial Sequence
<220> FEATURE:
<223> OTHER INFORMATION: Antibody Sequence

<400> SEQUENCE: 117

Trp Ala Ser Thr Arg Glu Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Antibody Sequence

<400> SEQUENCE: 118

Gln Asn Asp Tyr Ser Tyr Pro Tyr Thr
1               5

<210> SEQ ID NO 119
<211> LENGTH: 449
<212> TYPE: PRT
<213> ORGANISM: Artificial Sequence
<220> FEATURE:
<223> OTHER INFORMATION: Antibody Sequence

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser

```
145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 120
<211> LENGTH: 220
<212> TYPE: PRT
<213> ORGANISM: Artificial Sequence
<220> FEATURE:
<223> OTHER INFORMATION: Antibody Sequence

<400> SEQUENCE: 120

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
                20                  25                  30

Gly Asn Gln Lys Asn Tyr Leu Thr Trp Tyr Gln Gln Lys Pro Gly Gln
                35                  40                  45

Pro Pro Lys Leu Leu Ile Tyr Trp Ala Ser Thr Arg Glu Ser Gly Val
50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 121
<211> LENGTH: 120
<212> TYPE: PRT
<213> ORGANISM: Artificial Sequence
<220> FEATURE:
<223> OTHER INFORMATION: Antibody Sequence

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 122
<211> LENGTH: 5
<212> TYPE: PRT
<213> ORGANISM: Artificial Sequence
<220> FEATURE:
<223> OTHER INFORMATION: Antibody Sequence

<400> SEQUENCE: 122

Asp Tyr Tyr Met Lys
1               5
```

```
<210> SEQ ID NO 123
<211> LENGTH: 17
<212> TYPE: PRT
<213> ORGANISM: Artificial Sequence
<220> FEATURE:
<223> OTHER INFORMATION: Antibody Sequence

<400> SEQUENCE: 123

Asp Ile Ile Pro Ser Asn Gly Ala Thr Phe Tyr Asn Gln Lys Phe Lys
1               5                   10                  15
Gly

<210> SEQ ID NO 124
<211> LENGTH: 11
<212> TYPE: PRT
<213> ORGANISM: Artificial Sequence
<220> FEATURE:
<223> OTHER INFORMATION: Antibody Sequence

<400> SEQUENCE: 124

Ser His Leu Leu Arg Ala Ser Trp Phe Ala Tyr
1               5                   10

<210> SEQ ID NO 125
<211> LENGTH: 113
<212> TYPE: PRT
<213> ORGANISM: Artificial Sequence
<220> FEATURE:
<223> OTHER INFORMATION: Antibody Sequence

<400> SEQUENCE: 125

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
Lys

<210> SEQ ID NO 126
<211> LENGTH: 17
<212> TYPE: PRT
<213> ORGANISM: Artificial Sequence
<220> FEATURE:
<223> OTHER INFORMATION: Antibody Sequence

<400> SEQUENCE: 126

Glu Ser Ser Gln Ser Val Leu Asn Ser Gly Asn Gln Lys Asn Tyr Leu
1               5                   10                  15
Thr

<210> SEQ ID NO 127
<211> LENGTH: 7
<212> TYPE: PRT
```

```
<213> ORGANISM: Artificial Sequence
<220> FEATURE:
<223> OTHER INFORMATION: Antibody Sequence

<400> SEQUENCE: 127

Trp Ala Ser Thr Arg Glu Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Antibody Sequence

<400> SEQUENCE: 128

Gln Asn Asp Tyr Ser Tyr Pro Tyr Thr
1               5

<210> SEQ ID NO 129
<211> LENGTH: 449
<212> TYPE: PRT
<213> ORGANISM: Artificial Sequence
<220> FEATURE:
<223> OTHER INFORMATION: Antibody Sequence

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 130
<211> LENGTH: 220
<212> TYPE: PRT
<213> ORGANISM: Artificial Sequence
<220> FEATURE:
<223> OTHER INFORMATION: Antibody Sequence

<400> SEQUENCE: 130

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 131
<211> LENGTH: 118
<212> TYPE: PRT
<213> ORGANISM: Artificial Sequence
<220> FEATURE:
<223> OTHER INFORMATION: Antibody Sequence

<400> SEQUENCE: 131

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115
```

<210> SEQ ID NO 132
<211> LENGTH: 6
<212> TYPE: PRT
<213> ORGANISM: Artificial Sequence
<220> FEATURE:
<223> OTHER INFORMATION: Antibody Sequence

<400> SEQUENCE: 132

```
Ser Gly Tyr Tyr Trp Asn
1               5
```

<210> SEQ ID NO 133
<211> LENGTH: 17
<212> TYPE: PRT
<213> ORGANISM: Artificial Sequence
<220> FEATURE:
<223> OTHER INFORMATION: Antibody Sequence

<400> SEQUENCE: 133

```
Tyr Ile Ser Tyr Asp Gly Ser Asn Asn Tyr Asn Pro Ser Leu Lys Asn
1               5                   10                  15

Gly
```

<210> SEQ ID NO 134
<211> LENGTH: 8
<212> TYPE: PRT
<213> ORGANISM: Artificial Sequence

```
<220> FEATURE:
<223> OTHER INFORMATION: Antibody Sequence

<400> SEQUENCE: 134

Gly Glu Gly Phe Tyr Phe Asp Ser
1               5

<210> SEQ ID NO 135
<211> LENGTH: 113
<212> TYPE: PRT
<213> ORGANISM: Artificial Sequence
<220> FEATURE:
<223> OTHER INFORMATION: Antibody Sequence

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Leu Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys

<210> SEQ ID NO 136
<211> LENGTH: 17
<212> TYPE: PRT
<213> ORGANISM: Artificial Sequence
<220> FEATURE:
<223> OTHER INFORMATION: Antibody Sequence

<400> SEQUENCE: 136

Lys Ser Ser Gln Ser Leu Phe Phe Gly Ser Thr Gln Lys Asn Tyr Leu
1               5                   10                  15

Ala

<210> SEQ ID NO 137
<211> LENGTH: 7
<212> TYPE: PRT
<213> ORGANISM: Artificial Sequence
<220> FEATURE:
<223> OTHER INFORMATION: Antibody Sequence

<400> SEQUENCE: 137

Trp Ala Ser Thr Arg Glu Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Antibody Sequence

<400> SEQUENCE: 138
```

Gln Gln Tyr Tyr Asn Tyr Pro Trp Thr
1               5

<210> SEQ ID NO 139
<211> LENGTH: 447
<212> TYPE: PRT
<213> ORGANISM: Artificial Sequence
<220> FEATURE:
<223> OTHER INFORMATION: Antibody Sequence

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 140
<211> LENGTH: 220
<212> TYPE: PRT
<213> ORGANISM: Artificial Sequence
<220> FEATURE:
<223> OTHER INFORMATION: Antibody Sequence

<400> SEQUENCE: 140

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 141
<211> LENGTH: 118
<212> TYPE: PRT
<213> ORGANISM: Artificial Sequence
<220> FEATURE:
<223> OTHER INFORMATION: Antibody Sequence

<400> SEQUENCE: 141

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Ser Asn Trp Ile Arg Gln Ala Pro Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 142
<211> LENGTH: 6
<212> TYPE: PRT
<213> ORGANISM: Artificial Sequence
<220> FEATURE:
<223> OTHER INFORMATION: Antibody Sequence

<400> SEQUENCE: 142

Ser Gly Tyr Tyr Ser Asn
1               5

<210> SEQ ID NO 143
<211> LENGTH: 17
<212> TYPE: PRT
<213> ORGANISM: Artificial Sequence
<220> FEATURE:
<223> OTHER INFORMATION: Antibody Sequence

<400> SEQUENCE: 143

Tyr Ile Ser Tyr Asp Gly Ser Asn Asn Tyr Asn Pro Ser Leu Lys Asn
1               5                   10                  15

Gly

<210> SEQ ID NO 144
<211> LENGTH: 8
<212> TYPE: PRT
<213> ORGANISM: Artificial Sequence
<220> FEATURE:
<223> OTHER INFORMATION: Antibody Sequence

<400> SEQUENCE: 144

Gly Glu Gly Phe Tyr Phe Asp Ser
1               5

<210> SEQ ID NO 145
<211> LENGTH: 113
<212> TYPE: PRT
<213> ORGANISM: Artificial Sequence
<220> FEATURE:
<223> OTHER INFORMATION: Antibody Sequence

<400> SEQUENCE: 145

Glu Ile Val Leu Thr Gln Ser Pro Gly Thr Leu Ser Leu Ser Pro Gly
1               5                   10                  15
```

-continued

```
Glu Arg Ala Thr Leu Ser Cys Lys Ser Ser Gln Ser Leu Phe Phe Gly
             20                  25                  30

Ser Thr Gln Lys Asn Tyr Leu Ala Trp Tyr Gln Leu Lys Pro Gly Gln
         35                  40                  45

Ala Pro Arg Leu Leu Ile Tyr Trp Ala Ser Thr Arg Glu Ser Gly Ile
     50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                 85                  90                  95

Tyr Tyr Asn Tyr Pro Trp Thr Phe Gly Gln Gly Thr Lys Leu Glu Ile
            100                 105                 110

Lys
```

<210> SEQ ID NO 146
<211> LENGTH: 17
<212> TYPE: PRT
<213> ORGANISM: Artificial Sequence
<220> FEATURE:
<223> OTHER INFORMATION: Antibody Sequence

<400> SEQUENCE: 146

```
Lys Ser Ser Gln Ser Leu Phe Phe Gly Ser Thr Gln Lys Asn Tyr Leu
1               5                   10                  15

Ala
```

<210> SEQ ID NO 147
<211> LENGTH: 7
<212> TYPE: PRT
<213> ORGANISM: Artificial Sequence
<220> FEATURE:
<223> OTHER INFORMATION: Antibody Sequence

<400> SEQUENCE: 147

```
Trp Ala Ser Thr Arg Glu Ser
1               5
```

<210> SEQ ID NO 148
<211> LENGTH: 9
<212> TYPE: PRT
<213> ORGANISM: Artificial Sequence
<220> FEATURE:
<223> OTHER INFORMATION: Antibody Sequence

<400> SEQUENCE: 148

```
Gln Gln Tyr Tyr Asn Tyr Pro Trp Thr
1               5
```

<210> SEQ ID NO 149
<211> LENGTH: 447
<212> TYPE: PRT
<213> ORGANISM: Artificial Sequence
<220> FEATURE:
<223> OTHER INFORMATION: Antibody Sequence

<400> SEQUENCE: 149

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
             20                  25                  30

Tyr Tyr Ser Asn Trp Ile Arg Gln Ala Pro Gly Lys Lys Leu Glu Trp
         35                  40                  45
```

```
Met Gly Tyr Ile Ser Tyr Asp Gly Ser Asn Asn Tyr Asn Pro Ser Leu
 50                  55                  60

Lys Asn Gly Arg Ile Thr Ile Ser Arg Asp Thr Ser Lys Asn Thr Phe
 65                  70                  75                  80

Tyr Leu Gln Met Asn Ser Leu Arg Ala Glu Asp Thr Ala Val Tyr Tyr
                 85                  90                  95

Cys Ala Arg Gly Glu Gly Phe Tyr Phe Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 150
<211> LENGTH: 220
```

```
<212> TYPE: PRT
<213> ORGANISM: Artificial Sequence
<220> FEATURE:
<223> OTHER INFORMATION: Antibody Sequence

<400> SEQUENCE: 150

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 151
<211> LENGTH: 118
<212> TYPE: PRT
<213> ORGANISM: Artificial Sequence
<220> FEATURE:
<223> OTHER INFORMATION: Antibody Sequence

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Val Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110
```

Leu Val Thr Val Ser Ser
        115

<210> SEQ ID NO 152
<211> LENGTH: 6
<212> TYPE: PRT
<213> ORGANISM: Artificial Sequence
<220> FEATURE:
<223> OTHER INFORMATION: Antibody Sequence

<400> SEQUENCE: 152

Ser Gly Tyr Tyr Trp Asn
1               5

<210> SEQ ID NO 153
<211> LENGTH: 17
<212> TYPE: PRT
<213> ORGANISM: Artificial Sequence
<220> FEATURE:
<223> OTHER INFORMATION: Antibody Sequence

<400> SEQUENCE: 153

Tyr Ile Ser Tyr Asp Gly Ser Asn Asn Tyr Asn Pro Ser Leu Lys Asn
1               5                   10                  15

Gly

<210> SEQ ID NO 154
<211> LENGTH: 8
<212> TYPE: PRT
<213> ORGANISM: Artificial Sequence
<220> FEATURE:
<223> OTHER INFORMATION: Antibody Sequence

<400> SEQUENCE: 154

Gly Glu Gly Phe Tyr Phe Asp Ser
1               5

<210> SEQ ID NO 155
<211> LENGTH: 113
<212> TYPE: PRT
<213> ORGANISM: Artificial Sequence
<220> FEATURE:
<223> OTHER INFORMATION: Antibody Sequence

<400> SEQUENCE: 155

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys

```
<210> SEQ ID NO 156
<211> LENGTH: 17
<212> TYPE: PRT
<213> ORGANISM: Artificial Sequence
<220> FEATURE:
<223> OTHER INFORMATION: Antibody Sequence

<400> SEQUENCE: 156

Lys Ser Ser Gln Ser Leu Phe Phe Gly Ser Thr Gln Lys Asn Tyr Leu
1               5                   10                  15

Ala

<210> SEQ ID NO 157
<211> LENGTH: 7
<212> TYPE: PRT
<213> ORGANISM: Artificial Sequence
<220> FEATURE:
<223> OTHER INFORMATION: Antibody Sequence

<400> SEQUENCE: 157

Trp Ala Ser Thr Arg Glu Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Antibody Sequence

<400> SEQUENCE: 158

Gln Gln Tyr Tyr Asn Tyr Pro Trp Thr
1               5

<210> SEQ ID NO 159
<211> LENGTH: 447
<212> TYPE: PRT
<213> ORGANISM: Artificial Sequence
<220> FEATURE:
<223> OTHER INFORMATION: Antibody Sequence

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Val Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 160
<211> LENGTH: 220
<212> TYPE: PRT
<213> ORGANISM: Artificial Sequence
<220> FEATURE:
<223> OTHER INFORMATION: Antibody Sequence

<400> SEQUENCE: 160

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Ser Gly Ile
            50                  55                  60

Pro Asp Arg Phe Ser Gly Ser Gly Ser Gly Thr Asp Phe Thr Leu Thr
65                  70                  75                  80
```

Ile Ser Arg Leu Glu Pro Glu Asp Phe Ala Val Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
            210                 215                 220

<210> SEQ ID NO 161
<211> LENGTH: 118
<212> TYPE: PRT
<213> ORGANISM: Artificial Sequence
<220> FEATURE:
<223> OTHER INFORMATION: Antibody Sequence

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Asn
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 162
<211> LENGTH: 6
<212> TYPE: PRT
<213> ORGANISM: Artificial Sequence
<220> FEATURE:
<223> OTHER INFORMATION: Antibody Sequence

<400> SEQUENCE: 162

Ser Asn Tyr Tyr Trp Asn
1               5

<210> SEQ ID NO 163
<211> LENGTH: 17
<212> TYPE: PRT

```
<213> ORGANISM: Artificial Sequence
<220> FEATURE:
<223> OTHER INFORMATION: Antibody Sequence

<400> SEQUENCE: 163

Tyr Ile Ser Tyr Asp Gly Ser Asn Asn Tyr Asn Pro Ser Leu Lys Asn
1               5                   10                  15

Gly

<210> SEQ ID NO 164
<211> LENGTH: 8
<212> TYPE: PRT
<213> ORGANISM: Artificial Sequence
<220> FEATURE:
<223> OTHER INFORMATION: Antibody Sequence

<400> SEQUENCE: 164

Gly Glu Gly Phe Tyr Phe Asp Ser
1               5

<210> SEQ ID NO 165
<211> LENGTH: 113
<212> TYPE: PRT
<213> ORGANISM: Artificial Sequence
<220> FEATURE:
<223> OTHER INFORMATION: Antibody Sequence

<400> SEQUENCE: 165

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys

<210> SEQ ID NO 166
<211> LENGTH: 17
<212> TYPE: PRT
<213> ORGANISM: Artificial Sequence
<220> FEATURE:
<223> OTHER INFORMATION: Antibody Sequence

<400> SEQUENCE: 166

Lys Ser Ser Gln Ser Leu Phe Phe Gly Ser Thr Gln Lys Asn Tyr Leu
1               5                   10                  15

Ala

<210> SEQ ID NO 167
<211> LENGTH: 7
<212> TYPE: PRT
<213> ORGANISM: Artificial Sequence
<220> FEATURE:
<223> OTHER INFORMATION: Antibody Sequence
```

<400> SEQUENCE: 167

Trp Ala Ser Thr Arg Glu Ser
1               5

<210> SEQ ID NO 168
<211> LENGTH: 9
<212> TYPE: PRT
<213> ORGANISM: Artificial Sequence
<220> FEATURE:
<223> OTHER INFORMATION: Antibody Sequence

<400> SEQUENCE: 168

Gln Gln Tyr Tyr Asn Tyr Pro Trp Thr
1               5

<210> SEQ ID NO 169
<211> LENGTH: 447
<212> TYPE: PRT
<213> ORGANISM: Artificial Sequence
<220> FEATURE:
<223> OTHER INFORMATION: Antibody Sequence

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Asn
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 170
<211> LENGTH: 220
<212> TYPE: PRT
<213> ORGANISM: Artificial Sequence
<220> FEATURE:
<223> OTHER INFORMATION: Antibody Sequence

<400> SEQUENCE: 170

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

-continued

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 171
<211> LENGTH: 118
<212> TYPE: PRT
<213> ORGANISM: Artificial Sequence
<220> FEATURE:
<223> OTHER INFORMATION: Antibody Sequence

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 172
<211> LENGTH: 6
<212> TYPE: PRT
<213> ORGANISM: Artificial Sequence
<220> FEATURE:
<223> OTHER INFORMATION: Antibody Sequence

<400> SEQUENCE: 172

Ser Gly Tyr Tyr Trp Asn
1               5

<210> SEQ ID NO 173
<211> LENGTH: 17
<212> TYPE: PRT
<213> ORGANISM: Artificial Sequence
<220> FEATURE:
<223> OTHER INFORMATION: Antibody Sequence

<400> SEQUENCE: 173

Tyr Ile Ser Tyr Asp Gly Ser Asn Asn Tyr Asn Pro Ser Leu Lys Asn
1               5                   10                  15

Gly

<210> SEQ ID NO 174
<211> LENGTH: 8
<212> TYPE: PRT
<213> ORGANISM: Artificial Sequence
<220> FEATURE:
<223> OTHER INFORMATION: Antibody Sequence

<400> SEQUENCE: 174

Gly Glu Gly Phe Tyr Phe Asp Ser
1               5

<210> SEQ ID NO 175
<211> LENGTH: 108
<212> TYPE: PRT
<213> ORGANISM: Artificial Sequence
<220> FEATURE:
<223> OTHER INFORMATION: Antibody Sequence

<400> SEQUENCE: 175

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Trp Ala Ser Thr Arg Glu Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Asn Tyr Pro
                85                  90                  95

Trp Thr Phe Gly Gln Gly Thr Lys Leu Glu Ile Lys
            100                 105

<210> SEQ ID NO 176
<211> LENGTH: 12
<212> TYPE: PRT
<213> ORGANISM: Artificial Sequence
<220> FEATURE:
<223> OTHER INFORMATION: Antibody Sequence

<400> SEQUENCE: 176

Arg Ala Ser Gln Ser Val Ser Ser Ser Tyr Leu Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Antibody Sequence

<400> SEQUENCE: 177

Trp Ala Ser Thr Arg Glu Ser
1               5

<210> SEQ ID NO 178
<211> LENGTH: 9
<212> TYPE: PRT
<213> ORGANISM: Artificial Sequence
<220> FEATURE:
<223> OTHER INFORMATION: Antibody Sequence

<400> SEQUENCE: 178

Gln Gln Tyr Tyr Asn Tyr Pro Trp Thr
1               5

<210> SEQ ID NO 179
<211> LENGTH: 447
<212> TYPE: PRT
<213> ORGANISM: Artificial Sequence
<220> FEATURE:

<223> OTHER INFORMATION: Antibody Sequence

<400> SEQUENCE: 179

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
        435                 440                 445

<210> SEQ ID NO 180
<211> LENGTH: 215
<212> TYPE: PRT
<213> ORGANISM: Artificial Sequence
<220> FEATURE:
<223> OTHER INFORMATION: Antibody Sequence

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Trp Ala Ser Thr Arg Glu Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Asn Tyr Pro
                85                  90                  95

Trp Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 181
<211> LENGTH: 118
<212> TYPE: PRT
<213> ORGANISM: Artificial Sequence
<220> FEATURE:
<223> OTHER INFORMATION: Antibody Sequence

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
 65                  70                  75                  80

Tyr Leu Gln Met Asn Ser Leu Arg Ala Glu Asp Thr Ala Val Tyr Tyr
                 85                  90                  95

Cys Ala Arg Gly Glu Gly Phe Tyr Phe Asp Ser Trp Gly Gln Gly Thr
                100                 105                 110

Leu Val Thr Val Ser Ser
            115

<210> SEQ ID NO 182
<211> LENGTH: 6
<212> TYPE: PRT
<213> ORGANISM: Artificial Sequence
<220> FEATURE:
<223> OTHER INFORMATION: Antibody Sequence

<400> SEQUENCE: 182

Ser Gly Tyr Tyr Trp Asn
1               5

<210> SEQ ID NO 183
<211> LENGTH: 17
<212> TYPE: PRT
<213> ORGANISM: Artificial Sequence
<220> FEATURE:
<223> OTHER INFORMATION: Antibody Sequence

<400> SEQUENCE: 183

Tyr Ile Ser Tyr Asp Gly Ser Asn Asn Tyr Asn Pro Ser Leu Lys Asn
1               5                   10                  15

Gly

<210> SEQ ID NO 184
<211> LENGTH: 8
<212> TYPE: PRT
<213> ORGANISM: Artificial Sequence
<220> FEATURE:
<223> OTHER INFORMATION: Antibody Sequence

<400> SEQUENCE: 184

Gly Glu Gly Phe Tyr Phe Asp Ser
1               5

<210> SEQ ID NO 185
<211> LENGTH: 113
<212> TYPE: PRT
<213> ORGANISM: Artificial Sequence
<220> FEATURE:
<223> OTHER INFORMATION: Antibody Sequence

<400> SEQUENCE: 185

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
                20                  25                  30

Ser Thr Gln Lys Asn Tyr Leu Ala Trp Tyr Gln Gln Lys Pro Gly Gln
            35                  40                  45

Ala Pro Arg Leu Leu Ile Tyr Gly Ala Ser Ser Arg Ala Thr Gly Ile
        50                  55                  60

```
Pro Asp Arg Phe Ser Gly Ser Gly Ser Gly Thr Asp Phe Thr Leu Thr
 65                  70                  75                  80

Ile Ser Arg Leu Glu Pro Glu Asp Phe Ala Val Tyr Tyr Cys Gln Gln
                 85                  90                  95

Tyr Tyr Asn Tyr Pro Trp Thr Phe Gly Gln Gly Thr Lys Leu Glu Ile
            100                 105                 110

Lys
```

```
<210> SEQ ID NO 186
<211> LENGTH: 17
<212> TYPE: PRT
<213> ORGANISM: Artificial Sequence
<220> FEATURE:
<223> OTHER INFORMATION: Antibody Sequence

<400> SEQUENCE: 186

Lys Ser Ser Gln Ser Leu Phe Phe Gly Ser Thr Gln Lys Asn Tyr Leu
1               5                   10                  15

Ala
```

```
<210> SEQ ID NO 187
<211> LENGTH: 7
<212> TYPE: PRT
<213> ORGANISM: Artificial Sequence
<220> FEATURE:
<223> OTHER INFORMATION: Antibody Sequence

<400> SEQUENCE: 187

Gly Ala Ser Ser Arg Ala Thr
1               5
```

```
<210> SEQ ID NO 188
<211> LENGTH: 9
<212> TYPE: PRT
<213> ORGANISM: Artificial Sequence
<220> FEATURE:
<223> OTHER INFORMATION: Antibody Sequence

<400> SEQUENCE: 188

Gln Gln Tyr Tyr Asn Tyr Pro Trp Thr
1               5
```

```
<210> SEQ ID NO 189
<211> LENGTH: 447
<212> TYPE: PRT
<213> ORGANISM: Artificial Sequence
<220> FEATURE:
<223> OTHER INFORMATION: Antibody Sequence

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
                20                  25                  30

Tyr Tyr Trp Asn Trp Ile Arg Gln Ala Pro Gly Lys Lys Leu Glu Trp
            35                  40                  45

Met Gly Tyr Ile Ser Tyr Asp Gly Ser Asn Asn Tyr Asn Pro Ser Leu
        50                  55                  60

Lys Asn Gly Arg Ile Thr Ile Ser Arg Asp Thr Ser Lys Asn Thr Phe
 65                  70                  75                  80

Tyr Leu Gln Met Asn Ser Leu Arg Ala Glu Asp Thr Ala Val Tyr Tyr
                 85                  90                  95
```

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 190
<211> LENGTH: 220
<212> TYPE: PRT
<213> ORGANISM: Artificial Sequence
<220> FEATURE:
<223> OTHER INFORMATION: Antibody Sequence

<400> SEQUENCE: 190

Glu Ile Val Leu Thr Gln Ser Pro Gly Thr Leu Ser Leu Ser Pro Gly
1               5                   10                  15

-continued

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Gly Ala Ser Ser Arg Ala Thr Gly Ile
 50                  55                  60

Pro Asp Arg Phe Ser Gly Ser Gly Ser Gly Thr Asp Phe Thr Leu Thr
 65                  70                  75                  80

Ile Ser Arg Leu Glu Pro Glu Asp Phe Ala Val Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 191
<211> LENGTH: 118
<212> TYPE: PRT
<213> ORGANISM: Artificial Sequence
<220> FEATURE:
<223> OTHER INFORMATION: Antibody Sequence

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
 50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 192
<211> LENGTH: 6
<212> TYPE: PRT
<213> ORGANISM: Artificial Sequence

```
<220> FEATURE:
<223> OTHER INFORMATION: Antibody Sequence

<400> SEQUENCE: 192

Ser Gly Tyr Tyr Trp Asn
1               5

<210> SEQ ID NO 193
<211> LENGTH: 17
<212> TYPE: PRT
<213> ORGANISM: Artificial Sequence
<220> FEATURE:
<223> OTHER INFORMATION: Antibody Sequence

<400> SEQUENCE: 193

Tyr Ile Ser Tyr Asp Gly Ser Asn Asn Tyr Asn Pro Ser Leu Lys Asn
1               5                   10                  15
Gly

<210> SEQ ID NO 194
<211> LENGTH: 8
<212> TYPE: PRT
<213> ORGANISM: Artificial Sequence
<220> FEATURE:
<223> OTHER INFORMATION: Antibody Sequence

<400> SEQUENCE: 194

Gly Glu Gly Phe Tyr Phe Asp Ser
1               5

<210> SEQ ID NO 195
<211> LENGTH: 113
<212> TYPE: PRT
<213> ORGANISM: Artificial Sequence
<220> FEATURE:
<223> OTHER INFORMATION: Antibody Sequence

<400> SEQUENCE: 195

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Phe Phe Gly
                20                  25                  30

Ser Thr Gln Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110
Lys

<210> SEQ ID NO 196
<211> LENGTH: 17
<212> TYPE: PRT
<213> ORGANISM: Artificial Sequence
<220> FEATURE:
<223> OTHER INFORMATION: Antibody Sequence

<400> SEQUENCE: 196
```

```
Arg Ala Ser Gln Ser Val Phe Phe Gly Ser Thr Gln Lys Asn Tyr Leu
1               5                   10                  15
Ala

<210> SEQ ID NO 197
<211> LENGTH: 7
<212> TYPE: PRT
<213> ORGANISM: Artificial Sequence
<220> FEATURE:
<223> OTHER INFORMATION: Antibody Sequence

<400> SEQUENCE: 197

Trp Ala Ser Thr Arg Glu Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Antibody Sequence

<400> SEQUENCE: 198

Gln Gln Tyr Tyr Asn Tyr Pro Trp Thr
1               5

<210> SEQ ID NO 199
<211> LENGTH: 447
<212> TYPE: PRT
<213> ORGANISM: Artificial Sequence
<220> FEATURE:
<223> OTHER INFORMATION: Antibody Sequence

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 200
<211> LENGTH: 220
<212> TYPE: PRT
<213> ORGANISM: Artificial Sequence
<220> FEATURE:
<223> OTHER INFORMATION: Antibody Sequence

<400> SEQUENCE: 200

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125
```

Glu Gln Leu Lys Ser Gly Thr Ala Ser Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 201
<211> LENGTH: 120
<212> TYPE: PRT
<213> ORGANISM: Artificial Sequence
<220> FEATURE:
<223> OTHER INFORMATION: Antibody Sequence

<400> SEQUENCE: 201

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 202
<211> LENGTH: 5
<212> TYPE: PRT
<213> ORGANISM: Artificial Sequence
<220> FEATURE:
<223> OTHER INFORMATION: Antibody Sequence

<400> SEQUENCE: 202

Asp Tyr Tyr Met Lys
1               5

<210> SEQ ID NO 203
<211> LENGTH: 17
<212> TYPE: PRT
<213> ORGANISM: Artificial Sequence
<220> FEATURE:
<223> OTHER INFORMATION: Antibody Sequence

<400> SEQUENCE: 203

Asp Ile Ile Pro Ser Asn Gly Ala Thr Phe Tyr Asn Gln Lys Phe Lys
1               5                   10                  15

Gly

<210> SEQ ID NO 204
<211> LENGTH: 11
<212> TYPE: PRT
<213> ORGANISM: Artificial Sequence
<220> FEATURE:
<223> OTHER INFORMATION: Antibody Sequence

<400> SEQUENCE: 204

Ser His Leu Leu Arg Ala Ser Trp Phe Ala Tyr
1               5                   10

<210> SEQ ID NO 205
<211> LENGTH: 113
<212> TYPE: PRT
<213> ORGANISM: Artificial Sequence
<220> FEATURE:
<223> OTHER INFORMATION: Antibody Sequence

<400> SEQUENCE: 205

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 206
<211> LENGTH: 17
<212> TYPE: PRT
<213> ORGANISM: Artificial Sequence
<220> FEATURE:
<223> OTHER INFORMATION: Antibody Sequence

<400> SEQUENCE: 206

Glu Ser Ser Gln Ser Val Leu Asn Ser Gly Asn Gln Lys Asn Tyr Leu
1               5                   10                  15

Thr

<210> SEQ ID NO 207
<211> LENGTH: 7
<212> TYPE: PRT
<213> ORGANISM: Artificial Sequence
<220> FEATURE:
<223> OTHER INFORMATION: Antibody Sequence

<400> SEQUENCE: 207

Trp Ala Ser Thr Arg Glu Ser
1               5

<210> SEQ ID NO 208
<211> LENGTH: 9

```
<212> TYPE: PRT
<213> ORGANISM: Artificial Sequence
<220> FEATURE:
<223> OTHER INFORMATION: Antibody Sequence

<400> SEQUENCE: 208

Gln Asn Asp Tyr Ser Tyr Pro Tyr Thr
1               5

<210> SEQ ID NO 209
<211> LENGTH: 449
<212> TYPE: PRT
<213> ORGANISM: Artificial Sequence
<220> FEATURE:
<223> OTHER INFORMATION: Antibody Sequence

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 210
<211> LENGTH: 220
<212> TYPE: PRT
<213> ORGANISM: Artificial Sequence
<220> FEATURE:
<223> OTHER INFORMATION: Antibody Sequence

<400> SEQUENCE: 210

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 211
<211> LENGTH: 120
<212> TYPE: PRT
<213> ORGANISM: Artificial Sequence
<220> FEATURE:
<223> OTHER INFORMATION: Antibody Sequence

<400> SEQUENCE: 211

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Gln Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 212
<211> LENGTH: 5
<212> TYPE: PRT
<213> ORGANISM: Artificial Sequence
<220> FEATURE:
<223> OTHER INFORMATION: Antibody Sequence

<400> SEQUENCE: 212

```
Asp Tyr Tyr Met Lys
1               5
```

<210> SEQ ID NO 213
<211> LENGTH: 17
<212> TYPE: PRT
<213> ORGANISM: Artificial Sequence
<220> FEATURE:
<223> OTHER INFORMATION: Antibody Sequence

<400> SEQUENCE: 213

```
Asp Ile Ile Pro Ser Asn Gly Ala Thr Phe Tyr Asn Gln Lys Phe Gln
1               5                   10                  15

Gly
```

<210> SEQ ID NO 214
<211> LENGTH: 11
<212> TYPE: PRT
<213> ORGANISM: Artificial Sequence
<220> FEATURE:
<223> OTHER INFORMATION: Antibody Sequence

<400> SEQUENCE: 214

```
Ser His Leu Leu Arg Ala Ser Trp Phe Ala Tyr
1               5                   10
```

<210> SEQ ID NO 215
<211> LENGTH: 113
<212> TYPE: PRT

```
<213> ORGANISM: Artificial Sequence
<220> FEATURE:
<223> OTHER INFORMATION: Antibody Sequence

<400> SEQUENCE: 215

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 216
<211> LENGTH: 17
<212> TYPE: PRT
<213> ORGANISM: Artificial Sequence
<220> FEATURE:
<223> OTHER INFORMATION: Antibody Sequence

<400> SEQUENCE: 216

Glu Ser Ser Gln Ser Leu Leu Asn Ser Gly Asn Gln Lys Asn Tyr Leu
1               5                   10                  15

Thr

<210> SEQ ID NO 217
<211> LENGTH: 7
<212> TYPE: PRT
<213> ORGANISM: Artificial Sequence
<220> FEATURE:
<223> OTHER INFORMATION: Antibody Sequence

<400> SEQUENCE: 217

Trp Ala Ser Thr Arg Glu Ser
1               5

<210> SEQ ID NO 218
<211> LENGTH: 9
<212> TYPE: PRT
<213> ORGANISM: Artificial Sequence
<220> FEATURE:
<223> OTHER INFORMATION: Antibody Sequence

<400> SEQUENCE: 218

Gln Asn Asp Tyr Ser Tyr Pro Tyr Thr
1               5

<210> SEQ ID NO 219
<211> LENGTH: 449
<212> TYPE: PRT
<213> ORGANISM: Artificial Sequence
<220> FEATURE:
<223> OTHER INFORMATION: Antibody Sequence

<400> SEQUENCE: 219
```

```
Gln Val Gln Leu Val Gln Ser Gly Ala Glu Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Gln Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

-continued

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 220
<211> LENGTH: 220
<212> TYPE: PRT
<213> ORGANISM: Artificial Sequence
<220> FEATURE:
<223> OTHER INFORMATION: Antibody Sequence

<400> SEQUENCE: 220

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 221
<211> LENGTH: 359
<212> TYPE: PRT
<213> ORGANISM: Homo sapiens

<400> SEQUENCE: 221

Lys Glu Asp Pro Asn Pro Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
        35                  40                  45

Cys Gln Phe Gly Ala Ile Ser Leu Cys Glu Val Thr Asn Tyr Thr Val
    50                  55                  60

-continued

```
Arg Val Ala Asn Pro Pro Phe Ser Thr Trp Ile Leu Phe Pro Glu Asn
 65              70                  75                  80

Ser Gly Lys Pro Trp Ala Gly Ala Glu Asn Leu Thr Cys Trp Ile His
             85                  90                  95

Asp Val Asp Phe Leu Ser Cys Ser Trp Ala Val Gly Pro Gly Ala Pro
             100                 105                 110

Ala Asp Val Gln Tyr Asp Leu Tyr Leu Asn Val Ala Asn Arg Arg Gln
             115                 120                 125

Gln Tyr Glu Cys Leu His Tyr Lys Thr Asp Ala Gln Gly Thr Arg Ile
         130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                 165                 170                 175

Thr Asp Lys Phe Val Val Phe Ser Gln Ile Glu Ile Leu Thr Pro Pro
                 180                 185                 190

Asn Met Thr Ala Lys Cys Asn Lys Thr His Ser Phe Met His Trp Lys
             195                 200                 205

Met Arg Ser His Phe Asn Arg Lys Phe Arg Tyr Glu Leu Gln Ile Gln
         210                 215                 220

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
                 245                 250                 255

Glu Arg Val Tyr Glu Phe Leu Ser Ala Trp Ser Thr Pro Gln Arg Phe
                 260                 265                 270

Glu Cys Asp Gln Glu Glu Gly Ala Asn Thr Arg Ala Trp Arg Thr Ser
             275                 280                 285

Leu Leu Ile Ala Leu Gly Thr Leu Leu Ala Leu Val Cys Val Phe Val
         290                 295                 300

Ile Cys Arg Arg Tyr Leu Val Met Gln Arg Leu Phe Pro Arg Ile Pro
305                 310                 315                 320

His Met Lys Asp Pro Ile Gly Asp Ser Phe Gln Asn Asp Lys Leu Val
                 325                 330                 335

Val Trp Glu Ala Gly Lys Ala Gly Leu Glu Glu Cys Leu Val Thr Glu
             340                 345                 350

Val Gln Val Val Gln Lys Thr
         355
```

SPECIFIC ANTIBODY-DRUG-CONJUGATES (ADCS) WITH KSP INHIBITORS AND ANTI-CD123-ANTIBODIES

CROSS-REFERENCE TO RELATED APPLICATIONS

This application is a continuation of U.S. application Ser. No. 17/225,947, filed on Apr. 8, 2021, which is a continuation of U.S. application Ser. No. 16/310,285, filed on Dec. 14, 2018, now patented as U.S. Pat. No. 11,001,636, issued on May 11, 2021, which is the U.S. National Stage Entry of International Application No. PCT/EP2017/063951, filed internationally on Jun. 8, 2017, which claims the benefit of European Application No. 16174654.0, filed on Jun. 15, 2016, all of which are hereby incorporated by reference in their entireties.

SEQUENCE LISTING

The content of the Sequence Listing in ASCII text file, electronically submitted via EFS-Web on Apr. 29, 2022, is incorporated herein by reference in its entirety: filename: "59362-717_302_Sequence_Listing.txt" (210,148 bytes).

INTRODUCTION

The invention relates to specific Antibody-Drug-Conjugates (ADCs) with KSP (kinesin spindle protein) inhibitors and anti-CD123-antibodies, to the use of these conjugates for the treatment and/or prophylaxis of diseases and to the use of these conjugates for preparing medicaments for treatment and/or prevention of diseases, in particular hyperproliferative and/or angiogenic disorders such as, for example, cancer diseases. Such treatments can be carried out as monotherapy or else in combination with other medicaments or further therapeutic measures.

Cancer diseases are the consequence of uncontrolled cell growth of the most diverse tissues. In many cases, the new cells penetrate into existing tissue (invasive growth), or they metastase into remote organs. Cancer diseases occur in the most diverse organs and often have tissue-specific courses of the disease. The term cancer as a generic term therefore describes a large group of defined diseases of various organs, tissue and cell types.

Tumours in early stages can possibly be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins and antibodies with one or more active compound molecules are known, in particular in the form of antibody drug conjugates (ADCs) in which an internalising antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophor molecules are attached via a polymeric linker to an antibody. As possible toxophors, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell Jul. 8, 2005 (1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject of a number of patent applications (e.g. WO2006/044825; WO2006/002236; WO2005/051922; WO2006/060737; WO03/060064; WO03/040979; and WO03/049527). However, since KSP unfolds its action only during a relatively short period of time during the mitosis phase, KSP inhibitors have to be present in a sufficiently high concentration during these initial phases.

In WO2015/096982 and WO2014/151030 antibody drug conjugates (ADCs) are described with kinesin spindel Protein (KSP) inhibitors.

CD123 is the alpha chain of the IL-3 receptor and is also referred to as IL3R-alpha. CD123 is known to be expressed on primary AML samples and has been reported on a number of malignant cells. Preferred anti-CD123 antibodies are derived from antibodies disclosed by Sun et al. (Sun et al., 1996, Blood 87(1):83-92) and by Kuo et al. (Kuo et al., 2009, Bioconjug Chem. 20(10):1975-82).

Even with regard to the several already known antibody-drug-conjugates, there is still a high demand for new compounds that increase the availability of active compounds that show acceptable or even better properties in comparison to the state of the art compounds.

SUMMARY

Against this background it is an object of the present invention to provide substances which, after administration at a relatively low concentration, unfold apoptotic action and may therefore be of benefit for cancer therapy.

It has now surprisingly been found that antibody-drug-conjugates that have a selected drug moiety as herein described together with a selected antibody as herein described show acceptable and significant better properties.

Particular preference is given here to the extracellular cancer target molecule CD123 (IL-3Rα). This extracellular cancer target molecule is also known as IL3RA (interleukin 3 receptor subunit alpha) and has the NCBI Gene ID: 3563.

For the target molecule CD123 antibody-drug-conjugates which provide a very potent and long lasting in vivo anti tumor efficacy have been found. Further antibody-drug-conjugates directed towards CD123 which induce a long-lasting tumor inhibition as indicated by the time period until re-growth of the tumor occurs have been found.

To achieve this object, the invention further provides humanized anti-CD123 antibodies which are in addition germlined, which means these have a very small deviation compared to antibody sequences of the human germline. Special preference is given for the antibodies called "TPP-8987", "TPP-9476", "TPP-8988" and "TPP-9342".

It has now surprisingly been found that a conjugate of an antibody (AK) or a functional fragment thereof together with one or more chemical compound(s) as defined in following formula (I) shows superiority over the known conjugates:

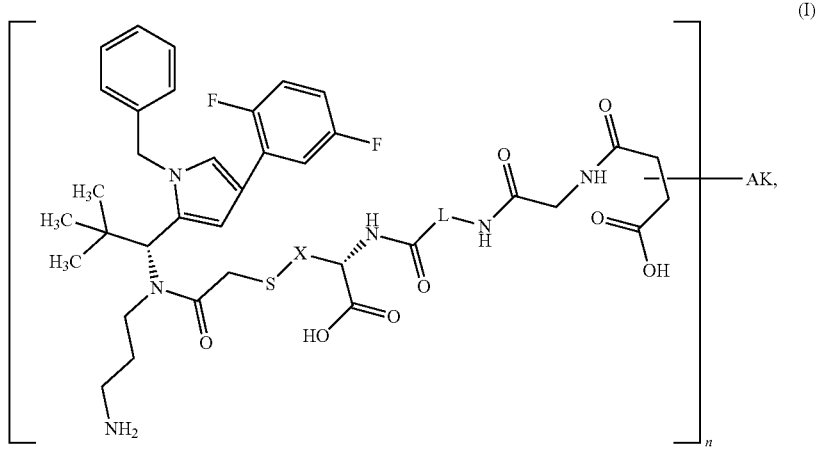

in which
X is —CH$_2$— or —CH$_2$—CH$_2$—,
L is (—CH$_2$—CH$_2$—O—)$_m$—CH$_2$—CH$_2$—,
m is 1 to 20,
n is 1 to 8 and
AK is an anti-CD123 antibody or a functional fragment thereof where the antibody or the functional fragment thereof is attached via a cysteine residue and said antibody or functional fragment thereof comprises
a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and
a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128, or
a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and
a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208, or
a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and
a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138, or a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and
a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198,
and the salts, solvates, salts of the solvates and epimers thereof.

DESCRIPTION OF THE FIGURES

FIG. 1A-FIG. 1Q: Sequence protocol.
FIG. 2A-FIG. 2D: Annotated sequence of antibodies. For each of the antibodies or antibody fragments, the CDR regions (HCDR1, HCDR2, HCDR3, LCDR1, LCDR2, LCDR3) and the variable regions (VH, VL) are emphasized.
TPP-8987 VH (SEQ ID NO: 121)
TPP-8987 VL (SEQ ID NO: 125)
TPP-8987 Heavy Chain (SEQ ID NO: 129)
TPP-8987 Light Chain (SEQ ID NO: 130)
TPP-8988 VH (SEQ ID NO: 131)
TPP-8988 VL (SEQ ID NO: 135)
TPP-8988 Heavy Chain (SEQ ID NO: 139)
TPP-8988 Light Chain (SEQ ID NO: 140)
TPP-9476 VH (SEQ ID NO: 201)
TPP-9476 VL (SEQ ID NO: 205)
TPP-9476 Heavy Chain (SEQ ID NO: 209)
TPP-9476 Light Chain (SEQ ID NO: 210)
TPP-9342 VH (SEQ ID NO: 191)
TPP-9342 VL (SEQ ID NO: 195)
TPP-9342 Heavy Chain (SEQ ID NO: 199)
TPP-9342 Light Chain (SEQ ID NO: 200)

DETAILED DESCRIPTION

Particularly preferred compounds of general formula (I) are those in which

X is —CH$_2$—,
L is (—CH$_2$—CH$_2$—O—)$_m$—CH$_2$—CH$_2$—,
m is 1 to 20,
n is 1 to 8 and
AK is an anti-CD123 antibody or a functional fragment thereof where the antibody or the functional fragment thereof is attached via a cysteine residue and said antibody or functional fragment thereof comprises
  a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and
  a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128, or
  a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and
  a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208, or
  a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and
  a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138, or
  a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and
  a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198,
and the salts, solvates, salts of the solvates and epimers thereof.

Particularly preferred compounds of general formula (I) are those in which
X is —CH$_2$—,
L is (—CH$_2$—CH$_2$—O—)$_m$—CH$_2$—CH$_2$—,
m is 1 to 20,
n is 1 to 8 and
AK is the anti-CD123 antibody TPP-8987, TPP-9476, TPP-8988, or TPP-9342 or a functional fragment thereof where the antibody or the functional fragment thereof is attached via a cysteine residue,
and the salts, solvates, salts of the solvates and epimers thereof.

More particularly preferred compounds of general formula (I) are those in which
X is —CH$_2$—,
L is (—CH$_2$—CH$_2$—O—)$_m$—CH$_2$—CH$_2$—,
m is 2 to 8,
n is 1 to 8 and
AK is an anti-CD123 antibody or a functional fragment thereof where the antibody or the functional fragment thereof is attached via a cysteine residue and said antibody or functional fragment thereof comprises
  a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and
  a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128, or
  a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and
  a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208, or
  a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and
  a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138, or
  a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and
  a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198,
and the salts, solvates, salts of the solvates and epimers thereof.

More particularly preferred compounds of general formula (I) are those in which

X is —CH$_2$—,
L is (—CH$_2$—CH$_2$—O—)$_m$—CH$_2$—CH$_2$—,
m is 2 to 8,
n is 1 to 8 and
AK is the anti-CD123 antibody TPP-8987, TPP-9476, TPP-8988, or TPP-9342 or a functional fragment thereof where the antibody or the functional fragment thereof is attached via a cysteine and the salts, solvates, salts of the solvates and epimers thereof.

More particularly preferred compounds of general formula (I) are:

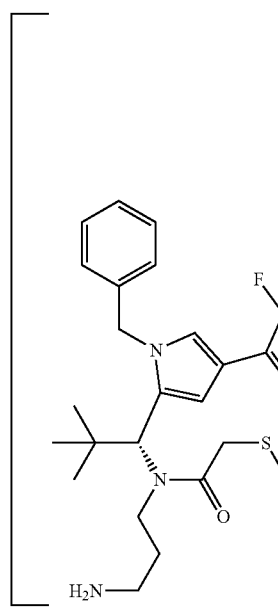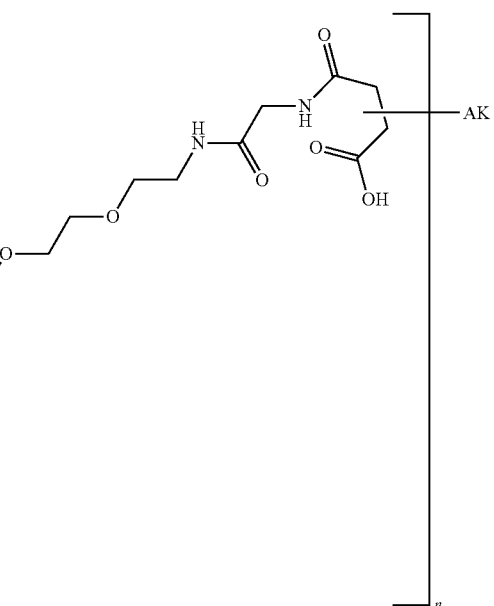

and in which n is 1 to 8 and

AK is an anti-CD123 antibody or a functional fragment thereof where the antibody or the functional fragment thereof is attached via a cysteine residue and said antibody or functional fragment thereof comprises a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128, or a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208, or a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138, or a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198.

The most preferred compound of general formula (I) is:

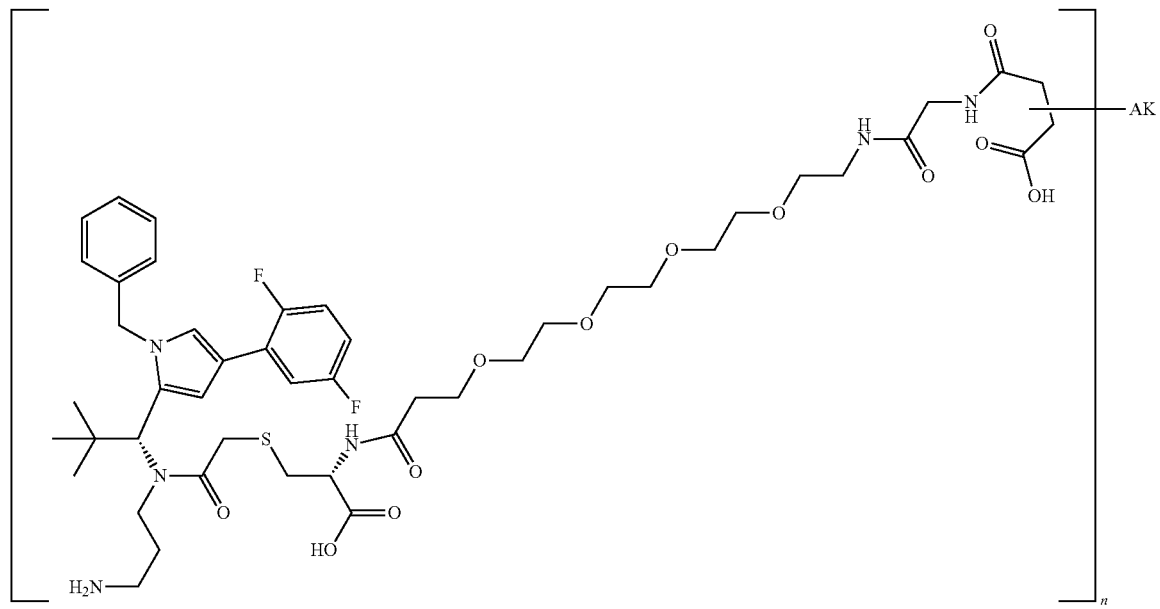

and in which
n is 1 to 8 and
AK is the anti-CD123 antibody TPP-8987, TPP-9476, TPP-8988, or TPP-9342 or a functional fragment thereof where the antibody or the functional fragment thereof is attached via a cysteine residue.

Further Description for Anti-CD123 Antibodies

The literature discloses various options of covalent coupling (conjugation) of organic molecules to antibodies. Preference according to the invention is given to the conjugation of the toxophores to the antibody via one or more sulphur atoms of cysteine residues of the antibody and/or via one or more NH groups of lysine residues of the antibody. However, it is also possible to bind the toxophor to the antibody via free carboxyl groups or via sugar residues of the antibody.

The antibody can be attached to the linker via a bond. Attachment of the antibody can be via a heteroatom of the binder. Heteroatoms according to the invention of the antibody which can be used for attachment are sulphur (in one embodiment via a sulphydryl group of the antibody), oxygen (according to the invention by means of a carboxyl or hydroxyl group of the antibody) and nitrogen (in one embodiment via a primary or secondary amine group or amide group of the antibody). These heteroatoms may be present in the natural antibody or are introduced by chemical methods or methods of molecular biology. According to the invention, the attachment of the antibody to the toxophor has only a minor effect on the binding activity of the antibody with respect to the target molecule. In a preferred embodiment, the attachment has no effect on the binding activity of the antibody with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophor (see Junutula et al. Nat Biotechnol. 2008, 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/µ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprises the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')2 and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tuft, et al., 1991, J. Immunol. 147:60 69; U.S. Pat. Nos. 4,474,893; 4,714,681; 4,925,648; 5,573,920; 5,601,819; or Kostelny et al., 1992, J. Immunol. 148: 1547 1553). An F(ab')$_2$ or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or phage display technologies (Clackson et al., Nature. Aug. 15, 1991; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blue staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Particular preference is given here to the extracellular cancer target molecule IL-3Rα, CD123 (SEQ ID NO: 221). This extracellular cancer target molecule is also known as IL3RA (interleukin 3 receptor subunit alpha) and has the NCBI Gene ID: 3563.

The functional interleukin 3 receptor is a heterodimer which comprises the specific alpha chain (IL-3Rα, CD123) and a "general" IL-3 receptor beta chain (βC, CD131) which is shared with the receptors for the granulocyte macrophage colony stimulating factor (GM-CSF) and interleukin 5 (IL-5).

IL-3Rα, CD123, is a transmembrane protein of type 1 having a calculated molecular weight of about 41 kDa. CD123 comprises an extracellular domain involved in IL-3 binding, a transmembrane domain and a short cytoplasmic end of about 50 amino acids. The extracellular domain consists of two regions: an N-terminal region of about 100 amino acids having sequence similarity to the equivalent regions of the GM-CSF and the IL-5 receptor alpha chain, and a region proximal to the transmembrane domain which region comprises four conserved cysteine residues and a WSXWS motif common in the cytokine receptor family.

The IL-3 binding domain comprises a cytokine receptor motif (CRM) of about 200 amino acid residues which is constructed of two domains which are folded Ig-like. The extracellular domain of IL-3Rα, CD123, is highly glycosylated, the N-glycosylation being required for ligand binding and receptor signal transduction.

IL-3Rα, CD123, is expressed extensively throughout the haematopoietic system, for example on haematopoietic precursor cells, mast cells, erythroid cells, megakaryocytes, neutrophil, basophil and eosinophil granulocytes, monocytes/macrophages, and CD5+ B lymphocytes; CD123 is also expressed on non-haematopoietic cells such as dendritic cells, Leydig cells, endothelial cells and stromal cells.

IL-3Rα, CD123, is also expressed by cells involved in certain diseases; these diseases comprise: myelodysplastic syndrome, leukaemia (such as acute myeloid leukaemia (AML)), lymphoma, allergies and autoimmune disorders such as lupus or scleroderma.

Owing to these relationships, anti-IL-3Rα, anti-CD123, antibodies can be employed in therapy as naked antibodies or coupled antibodies (such as ADCs).

The present invention relates to compounds coupled to antibodies specifically binding to IL-3Rα, CD123 (SEQ ID NO: 221).

The term "anti-CD123 antibody" relates to an antibody which specifically binds the cancer target molecule CD123 (IL-3Rα, SEQ ID NO: 221), preferentially with an affinity which is sufficient for a diagnostic and/or therapeutic application. In one embodiment, binding of an anti-CD123 antibody to a protein not related to CD123 is less than 10% of the binding of the antibody to CD123, determined, for example, by surface plasmon resonance spectroscopy. In certain embodiments, the antibody binds CD123 (IL-3Rα, SEQ ID NO: 221) with a dissociation constant (KD) of ≤1 µM, ≤100 nM, ≤10 nM, ≤1 nM, ≤0.1 nM, ≤0.01 nM, or ≤0.001 nM. In certain embodiments, the anti-CD123 antibody binds to an epitope which is conserved between different species.

Antibodies which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (19881, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Anti-CD123 Antibodies

According to the invention, use is made of an anti-CD123 antibody or an antigen-binding fragment thereof, preferably one selected from those described below or modified by suitable mutation. In addition, the person skilled in the art is familiar with antibodies binding to CD123.

Sun et al. (Sun et al., 1996, Blood 87(1):83-92) describe the generation and properties of the monoclonal antibody 7G3, which binds to the N-terminal domain of IL-3Rα, CD123. U.S. Pat. No. 6,177,078 (Lopez) relates to the anti-CD123 antibody 7G3. A chimeric variant of this antibody (CSL360) is described in WO 2009/070844, and a humanized version (CSL362) in WO 2012/021934. The sequence of the 7G3 antibody is disclosed in EP2426148.

This 7G3 sequence represents the starting point of the humanized and germlined antibodies TPP-8987 and TPP-9476.

An antibody which, after cell surface antigen binding, is internalized particularly well is the anti-CD123 antibody 12F1 disclosed by Kuo et al. (Kuo et al., 2009, Bioconjug Chem. 20(10):1975-82). The antibody 12F1 binds with higher affinity to CD123 than the antibody 7G3 and, after cell surface antigen binding, is internalized markedly faster than 7G3. Bispecific scFv immunofusion proteins based on 12F1 are disclosed in WO 2013/173820.

This 12F1 sequence represents the starting point of the humanized and germlined antibodies TPP-8988 and TPP-9342.

The invention relates in particular to conjugates with antibodies or antigen-binding antibody fragments thereof or variants thereof derived from the antibodies 7G3 (Sun et al., 1996, Blood 87(1):83-92) and 12F1 (Kuo et al., 2009, Bioconjug Chem. 20(10):1975-82) originated from the mouse, or to conjugates with antibodies or antigen-binding antibody fragments thereof or variants thereof derived from the antibody 12F1 (Kuo et al., 2009, Bioconjug Chem. 20(10):1975-82) originating from the mouse.

Generation of the Anti-CD123 Antibodies

Based on the publication of the sequences of the variable regions (VH and VL) of 7G3 (EP2426148), the following antibody sequences were obtained by CDR grafting in human framework regions and subsequent germlining optimization: TPP-8987 and TPP-9476.

Based on the publication of the sequences of the variable regions (VH and VL) of 12F1 (WO 2013/173820), the following antibody were obtained by CDR grafting in human framework regions and subsequent germlining optimization: TPP-8988 and TPP-9342.

Particular Embodiments of Anti-CD123 Antibodies

In the present application, reference is made to the following preferred anti-CD123 antibodies of the invention, as shown in the table below: "TPP-8987", "TPP-9476", "TPP-8988" and "TPP-9342".

TPP-8987 and TPP-9476 are humanized and germlined variants of the antibody 7G3.

TPP-8988 and TPP-9342 are humanized and germlined variants of the antibody 12F1

As shown in the examples it was a further object of this invention to provide antibodies of 7G3 and 12F1 which are humanized and which are very close to the human antibody germline sequences (germlined). Therefore antibodies TPP-8987, TPP-9476, TPP-8988, and TPP-9342 are further embodiments of this invention. The sequences of these antibodies are shown in the following table:

Table:Table of preferred anti-CD123antibodies for ADCs:

| Antibody | SEQ ID NO: | | | | | | | | Heavy Chain (IgG) | Light Chain (IgG) |
| --- | --- | --- | --- | --- | --- | --- | --- | --- | --- | --- |
| | VH | H-CDR1 | H-CDR2 | H-CDR3 | VL | L-CDR1 | L-CDR2 | L-CDR3 | | |
| TPP-8987 | 121 | 122 | 123 | 124 | 125 | 126 | 127 | 128 | 129 | 130 |
| TPP-9476 | 201 | 202 | 203 | 204 | 205 | 206 | 207 | 208 | 209 | 210 |
| TPP-8988 | 131 | 132 | 133 | 134 | 135 | 136 | 137 | 138 | 139 | 140 |
| TPP-9342 | 191 | 192 | 193 | 194 | 195 | 196 | 197 | 198 | 199 | 200 |

Particular preference is given for ADCs to the anti-CD123 antibodies called "TPP-8987", "TPP-9476", "TPP-8988" and "TPP-9342".

TPP-8987 is an anti-CD123 antibody which comprises a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128. TPP-9476 is an anti-CD123 antibody which comprises a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208.

TPP-8988 is an anti-CD123 antibody which comprises a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138.

TPP-9342 is an anti-CD123 antibody which comprises a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198.

TPP-8987 is an anti-CD123 antibody which preferably comprises a variable region of the heavy chain corresponding to SEQ ID NO: 121 and a variable region of the light chain corresponding to SEQ ID NO: 125.

TPP-9476 is an anti-CD123 antibody which preferably comprises a variable region of the heavy chain corresponding to SEQ ID NO: 201 and a variable region of the light chain corresponding to SEQ ID NO: 205.

TPP-8988 is an anti-CD123 antibody which preferably comprises a variable region of the heavy chain corresponding to SEQ ID NO: 131 and a variable region of the light chain corresponding to SEQ ID NO: 135.

TPP-9342 is an anti-CD123 antibody which preferably comprises a variable region of the heavy chain corresponding to SEQ ID NO: 191 and a variable region of the light chain corresponding to SEQ ID NO: 195.

TPP-8987 is an anti-CD123 antibody preferably comprising a region of the heavy chain corresponding to SEQ ID NO: 129 and a region of the light chain corresponding to SEQ ID NO: 130.

TPP-9476 is an anti-CD123 antibody preferably comprising a region of the heavy chain corresponding to SEQ ID NO: 209 and a region of the light chain corresponding to SEQ ID NO: 210.

TPP-8988 is an anti-CD123 antibody comprising a region of the heavy chain corresponding to SEQ ID NO: 139 and a region of the light chain preferably corresponding to SEQ ID NO: 140.

TPP-9342 is an anti-CD123 antibody preferably comprising a region of the heavy chain corresponding to SEQ ID NO: 199 and a region of the light chain corresponding to SEQ ID NO: 200.

Preferred embodiments of the anti-CD123 antibody for coupling with linkers and/or toxophores according to the invention are those below:

1. An antibody or an antigen-binding fragment thereof binding to CD123, comprising:
   a variable heavy chain comprising the variable CDR1 sequence of the heavy chain, as shown in SEQ ID NO: 122, the variable CDR2 sequence of the heavy chain, as shown in SEQ ID NO: 123, and the variable CDR3 sequence of the heavy chain, as shown in SEQ ID NO: 124, and
   a variable light chain comprising the variable CDR1 sequence of the light chain, as shown in SEQ ID NO: 126, the variable CDR2 sequence of the light chain, as shown in SEQ ID NO: 127, and the variable CDR3 sequence of the light chain, as shown in SEQ ID NO: 128, or a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204, and a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208, or a variable heavy chain comprising the variable CDR1 sequence of the heavy chain, as shown in SEQ ID NO: 132, the variable CDR2 sequence of the heavy chain, as shown in SEQ ID NO: 133, and the variable CDR3 sequence of the heavy chain, as shown in SEQ ID NO: 134, and a variable light chain comprising the variable CDR1 sequence of the light chain, as shown in SEQ ID NO: 136, the variable CDR2 sequence of the light chain, as shown in SEQ ID NO: 137, and the variable CDR3 sequence of the light chain, as shown in SEQ ID NO: 138, or a variable heavy chain comprising the variable CDR1 sequence of the heavy chain, as shown in SEQ ID NO: 192, the variable CDR2 sequence of the heavy chain, as shown in SEQ ID NO: 193, and the variable CDR3 sequence of the heavy chain, as shown in SEQ ID NO: 194, and a variable light chain comprising the variable CDR1 sequence of the light chain, as shown in SEQ ID NO: 196, the variable CDR2 sequence of the light chain, as shown in SEQ ID NO: 197, and the variable CDR3 sequence of the light chain, as shown in SEQ ID NO: 198.

2. The antibody or an antigen-binding fragment thereof according to embodiment 1, comprising:
   a variable sequence of the heavy chain, as shown in SEQ ID NO:121, and a variable sequence of the light chain, as shown in SEQ ID NO:125, or
   a variable sequence of the heavy chain, as shown in SEQ ID NO:201, and a variable sequence of the light chain, as shown in SEQ ID NO:205, or
   a variable sequence of the heavy chain, as shown in SEQ ID NO:131, and a variable sequence of the light chain, as shown in SEQ ID NO:135, or
   a variable sequence of the heavy chain, as shown in SEQ ID NO:191, and a variable sequence of the light chain, as shown in SEQ ID NO:195.

3. The antibody according to any of the preceding embodiments which is an IgG antibody.

4. The antibody according to any of the preceding embodiments, comprising:
   a sequence of the heavy chain, as shown in SEQ ID NO:129, and a sequence of the light chain, as shown in SEQ ID NO:130, or
   a sequence of the heavy chain, as shown in SEQ ID NO:209, and a sequence of the light chain, as shown in SEQ ID NO:210, or
   a sequence of the heavy chain, as shown in SEQ ID NO:139, and a sequence of the light chain, as shown in SEQ ID NO:140, or
   a sequence of the heavy chain, as shown in SEQ ID NO:199, and a sequence of the light chain, as shown in SEQ ID NO:200.

5. The antibody according to any of the preceding embodiments, comprising: The antigen-binding fragment according to any of the preceding embodiments or an antigen-binding fragment of an antibody according to any of the preceding embodiments which is an scFv, Fab, Fab fragment or a F(ab)2 fragment.

6. The antibody or the antigen-binding fragment according to any of the preceding embodiments which is a monoclonal antibody or an antigen-binding fragment thereof 7. The antibody or the antigen-binding fragment according to any of the preceding embodiments which is a human, humanized or chimeric antibody or an antigen-binding fragment.

Particular preference is given to the anti-CD123 antibodies called "TPP-8987", "TPP-9476", "TPP-8988" and "TPP-9342".

DNA Molecules of the Invention

The present invention also relates to the DNA molecules that encode an antibody of the invention or antigen-binding fragment thereof. These sequences are optimized in certain cases for mammalian expression. DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Functionally Equivalent DNA Variants

Yet another class of DNA variants within the scope of the invention may be described with reference to the product they encode. These functionally equivalent polynucleotides are characterized by the fact that they encode the same peptide sequences due to the degeneracy of the genetic code.

It is recognized that variants of DNA molecules provided herein can be constructed in several different ways. For example, they may be constructed as completely synthetic DNAs. Methods of efficiently synthesizing oligonucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration (s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences encoding the preferred antibodies of the present invention. The recombinant constructs of the present invention can be used in connection with a vector, such as a plasmid, phagemid, phage or viral vector, into which a DNA molecule encoding an antibody of the invention or antigen-binding fragment thereof or variant thereof is inserted.

An antibody, antigen binding portion, or variant thereof provided herein can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic hosts cells are yeasts, insects and insect cells, plants and plant cells, transgenic animals, or mammalian cells. In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Therefore, an embodiment of the present invention are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another embodiment of the present invention is a method of using the host cell to produce an antibody and antigen binding fragments, comprising culturing the host cell under suitable conditions and recovering said antibody.

Therefore another embodiment of the present invention is the production of the antibodies according to this invention with the host cells of the present invention and purification of these antibodies to at least 95% homogeneity by weight.

Bacterial Expression

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore, an embodiment of the present invention is an expression vector comprising a nucleic acid sequence encoding for the novel antibodies of the present invention.

Antibodies of the present invention or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces*, and *Staphylococcus*, preferably, from *E. coli* cells.

Mammalian Expression

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (N Y). 1992 February; 10(2):169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resistance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethylenimine (PEI)-based transfection and DEAE-dextran transfection.

Suitable mammalian host cells for expressing the antibodies, antigen binding fragments thereof or variants thereof provided herein include Chinese Hamster Ovary (CHO cells) such as CHO-K1, CHO-S, CHO-K1SV [including dhfr-CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15], NS0 myeloma cells, COS cells, HEK293 cells, HKB11 cells, BHK21 cells, CAP cells, EB66 cells, and SP2 cells.

Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. Jan. 15, 2002; 30 (2):E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Purification

Antibodies of the invention or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragments thereof or variants thereof include naturally purified products, products of chemical synthetic procedures, and products produced by recombinant techniques from an eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

Isotopes, Salts, Solvates, Isotopic Variants

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

In addition, the present invention also encompasses prodrugs of the compounds according to the invention. The term "prodrugs" here denotes compounds which may themselves be biologically active or inactive, but are converted (for example by metabolic or hydrolytic means) to inventive compounds during their residence time in the body.

Another embodiment of the invention is a conjugate as defined above where the antibody or functional fragment thereof binds to a cancer target molecule.

Another embodiment of the invention is a conjugate as defined above where the conjugate has 2 to 6 conjugation sites per antibody or functional fragment thereof.

Another embodiment of the invention is a conjugate as defined above where the conjugate has 2 conjugation sites per antibody or functional fragment thereof.

Another embodiment of the invention is a conjugate according as defined above where the conjugate has 4 conjugation sites per antibody or functional fragment thereof.

Another embodiment of the invention is a conjugate as defined above where the antibody or functional fragment thereof binds to an extracellular target molecule.

Another embodiment of the invention is a conjugate as defined above where the antibody or functional fragment thereof, after binding to the extracellular target molecule, is internalized and processed intracellularly (preferably lysosomally) by the cell expressing the target molecule.

Therapeutic Use

The CD123 targeted antibody-drug conjugates described herein may be used to treat a CD123 expressing disorder, such as CD 123 expressing cancer. Typically such cancers show detectable levels of CD123 measured at the protein (e.g., by immunoassay) or RNA level. Some such cancers show elevated levels of CD123 relative to noncancerous tissue of the same type, preferably from the same patient. Optionally, a level of CD 123 in a cancer is measured before performing treatment.

The CD 123 directed antibody drug conjugates may be used to treat CD123 expressing disease, including CD123 expressing cancers, like tumors of the hematopoietic and lymphoid tissues or hematopoietic and lymphoid malignancies.

Examples of cancers associated with CD123 expression include myeloid diseases such as, acute myeloid leukemia (AML) and myelodysplastic syndrome (MDS). Other cancers include B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

Methods of the present invention include treating a patient that has a cancer that expresses CD123 comprising administering to the patient an antibody-drug conjugate of the present invention. The cancer can be any CD123 expressing cancer, including, for example, AML, MDS, B-ALL, hairy cell leukemia, Fanconi anemia, BPDCN, Hodgkin's disease, Immature T-ALL, Burkitt's lymphoma, Follicular lymphoma, CLL, or mantle cell lymphoma.

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectormal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of soft tissue (inter alia soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative blood diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds according to the invention for the treatment and/or prevention of disorders, in particular the disorders mentioned above.

The present invention further provides for the use of the compounds according to the invention for producing a medicament for the treatment and/or prevention of disorders, in particular the disorders mentioned above.

The present invention further provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with one or more other pharmacologically active substances, provided that this combination does not lead to undesirable and unacceptable side effects. The present invention furthermore therefore provides medicaments containing at least one of the compounds according to the invention and one or more further active compounds, in particular for treatment and/or prevention of the abovementioned disorders.

For example, the compounds of the present invention can be combined with known anti-hyper-proliferative, cytostatic or cytotoxic substances for the treatment of cancer diseases. Examples of suitable combination active compounds include:

131I-chTNT, abarelix, abiraterone, aclarubicin, adotrastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+ estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, Iasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153 Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

In addition, the compounds of the present invention can be combined, for example, with binders which, by way of example, can bind to the following targets: OX-40, CD137/4-1BB, DR3, IDO1/IDO2, LAG-3, CD40.

In addition, the compounds according to the invention can also be used in combination with radiotherapy and/or surgical intervention.

Generally, the following aims can be pursued with the combination of compounds of the present invention with other cytostatically or cytotoxically active agents:
improved efficacy in slowing the growth of a tumour, in reducing its size or even in the complete elimination thereof, compared with treatment with an individual active compound;
the possibility of using the chemotherapeutics used in a lower dosage than in the case of monotherapy;
the possibility of a more tolerable therapy with fewer side effects compared with individual administration;
the possibility of treatment of a broader spectrum of tumour diseases;
the achievement of a higher rate of response to the therapy;
a longer survival time of the patient compared with present-day standard therapy.

In addition, the compounds according to the invention can also be used in combination with radiotherapy and/or surgical intervention.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example parenterally, possibly inhalatively or as implants or stents.

The compounds according to the invention can be administered in suitable administration forms for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of from about 0.001 to 1 mg/kg, preferably about 0.01 to 0.5 mg/kg, of body weight to achieve effective results.

It may nevertheless be necessary where appropriate to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

If, in the description of experiments, the temperature at which the reaction is carried out is not stated, room temperature can be assumed.

Synthesis Routes:

Exemplary for the working examples, the schemes below show exemplary synthesis routes leading to the working examples:

Scheme 1

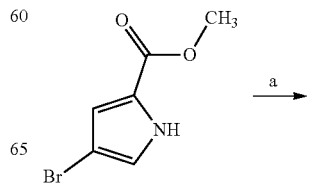

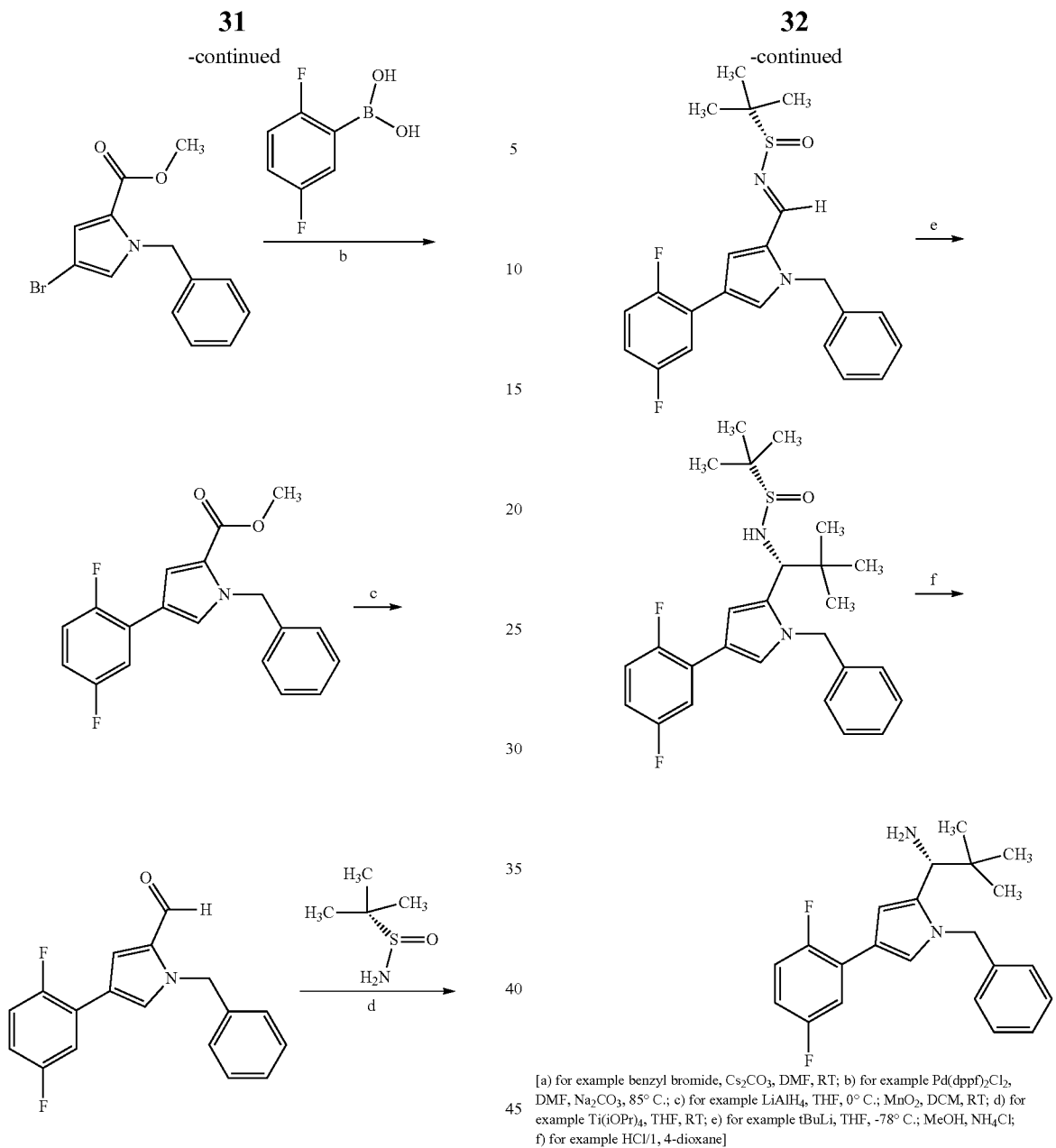
[a) for example benzyl bromide, Cs₂CO₃, DMF, RT; b) for example Pd(dppf)₂Cl₂, DMF, Na₂CO₃, 85° C.; c) for example LiAlH₄, THF, 0° C.; MnO₂, DCM, RT; d) for example Ti(iOPr)₄, THF, RT; e) for example tBuLi, THF, -78° C.; MeOH, NH₄Cl; f) for example HCl/1, 4-dioxane]
Scheme 2
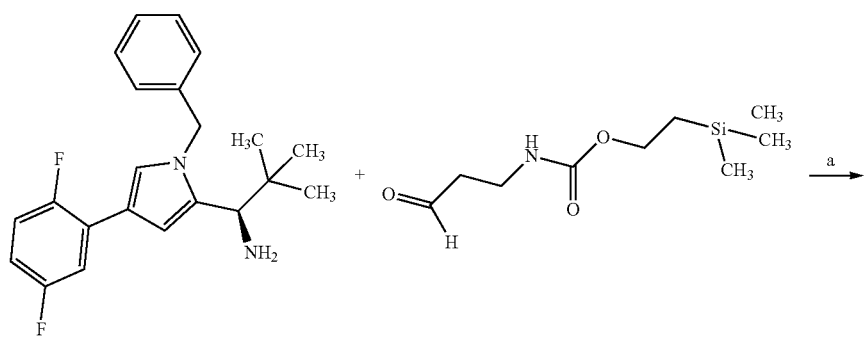

33                                                    34
-continued
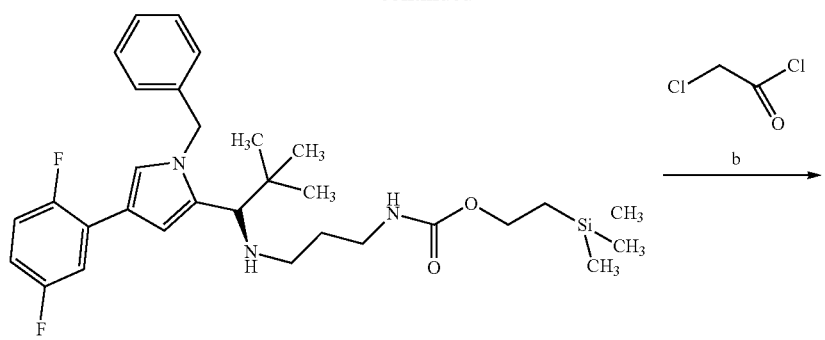
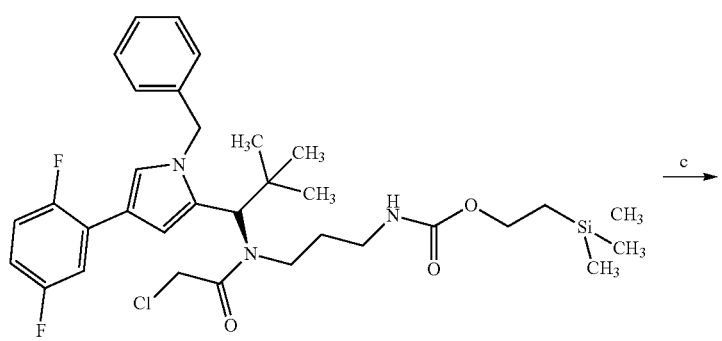
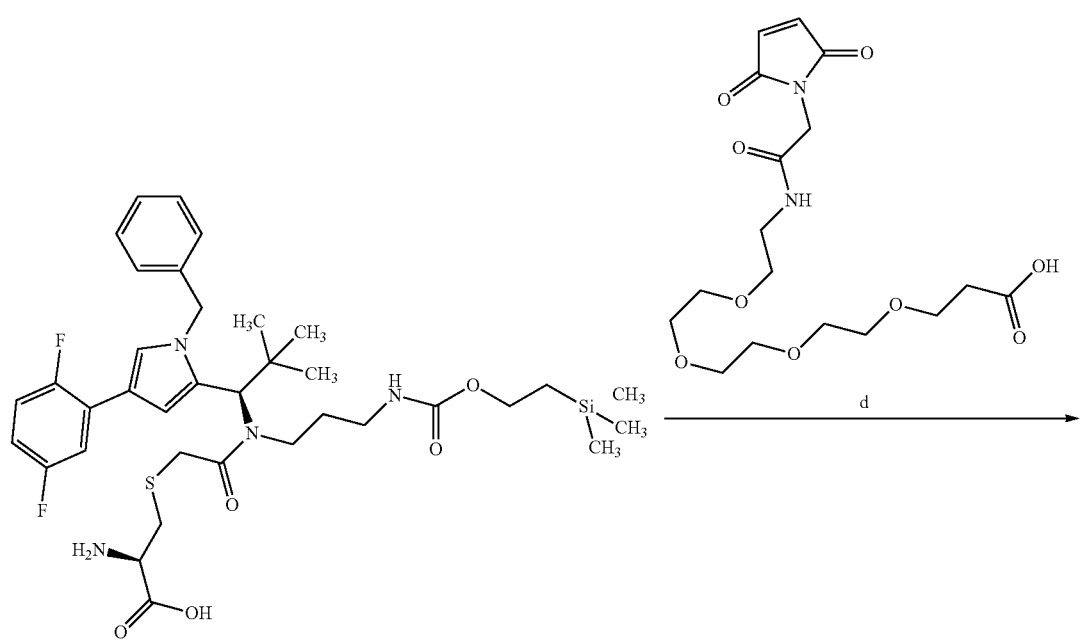

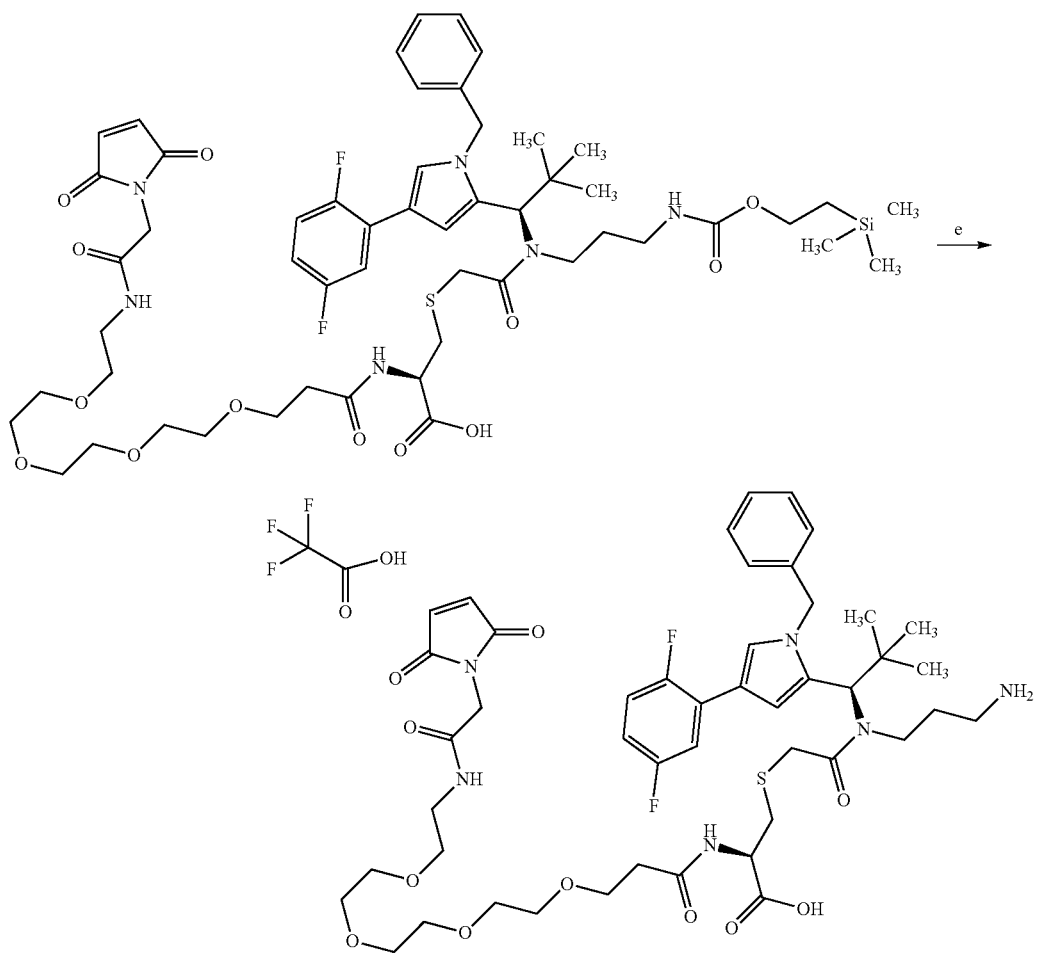
[a) NaBH(OAc)₃, HOAc, Dichlormethan, RT; b) Chloracetylchlorid, NEt₃, DCM, RT; c) L-Cystein, NaHCO₃, DBU, Isopropanol/Wasser, 50° C.; d) HATU, DMF, Diisopropylethylamin, RT; e) Zinkchlorid, Trifluorethanol, 50° C.;]
Scheme 3: Synthese of Cystein-linked ADC
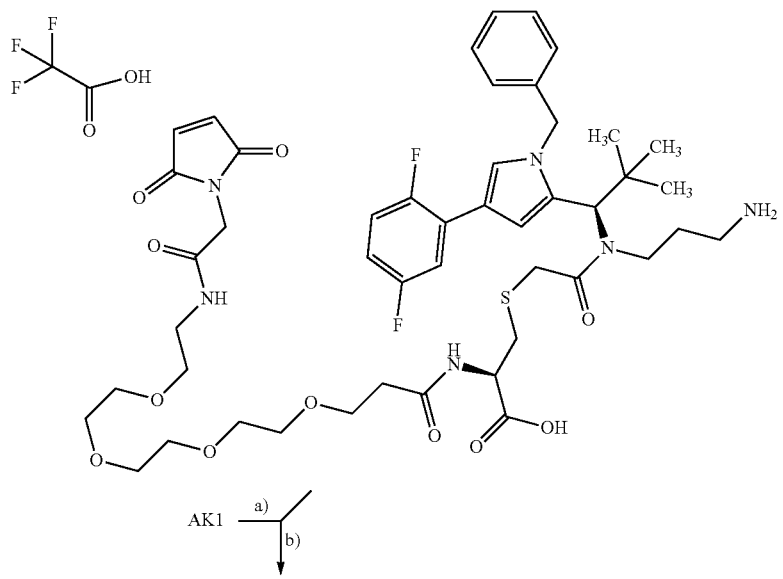

-continued

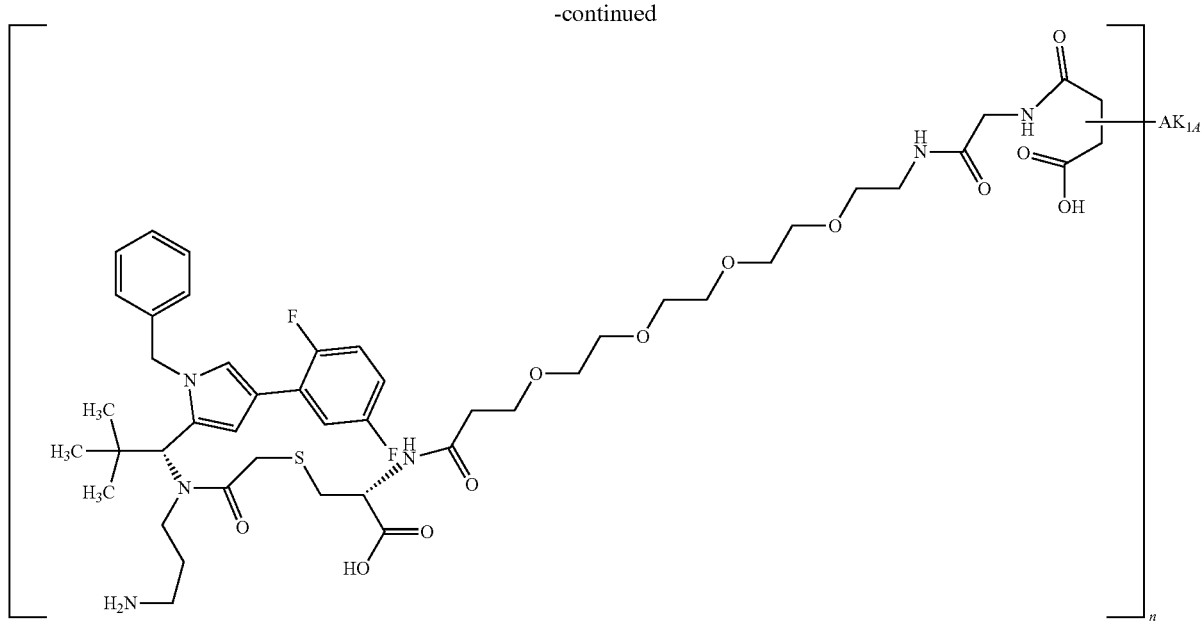

[a] 2-5 Eq TCEP, PBS pH7.2, 30 min stirring at RT; b) 90 min stirring at RT under Argon, then rebuffering at pH 8 using PD 10-column (Sephadex® G-25, GE Healthcare); overnight stirring at RT under Argon then concentration by ultracentrifugation and dilution with PBS buffer (pH 7.2)]

Exemplary for the working examples, the schemes below show exemplary synthesis routes leading to the working examples:

A. EXAMPLES

Abbreviations and Acronyms

ABCB1 ATP-binding cassette sub-family B member 1 (synonym for P-gp and MDR1)
ATP adenosine triphosphate
BCRP breast cancer resistance protein, an efflux transporter
BEP 2-bromo-1-ethylpyridinium tetrafluoroborate
d doublet (in NMR)
TLC thin-layer chromatography
DCM dichloromethane
dd doublet of doublets (in NMR)
DMF N,N-dimethylformamide
DMSO dimethyl sulphoxide
DPBS, D-PBS, PBS Dulbecco's phosphate-buffered salt solution
  PBS=DPBS=D-PBS, pH 7.4, from Sigma, No D8537
  Composition:
  0.2 g KCl
  0.2 g $KH_2PO_4$ (anhyd)
  8.0 g NaCl
  1.15 g $Na_2HPO_4$ (anhyd)
  made up ad 1 l with $H_2O$
DTT DL-dithiothreitol
EDC N'-(3-dimethylaminopropyl)-N-ethylcarbodiimide hydrochloride
EI electron impact ionization (in MS)
ELISA enzyme-linked immunosorbent assay
ESI electrospray ionization (in MS)
ESI-MicroTofq ESI-MicroTofq (name of the mass spectrometer with Tof=time of flight and q=quadrupol)
FCS foetal calf serum
Fmoc (9H-fluoren-9-ylmethoxy)carbonyl
sat. saturated
GTP guanosine-5'-triphosphate
h hour(s)
HATU O-(7-azabenzotriazol-1-yl)-N,N,N',N'-tetramethyluronium hexafluorophosphate
HEPES 4-(2-hydroxyethyl)piperazine-1-ethanesulphonic acid
HPLC high-pressure, high-performance liquid chromatography
$IC_{50}$ half-maximal inhibitory concentration
i.v. intravenously, administration into the vein
KG-1 human tumour cell line
LC-MS liquid chromatography-coupled mass spectrometry
LLC-PK1 cells Lewis lung carcinoma pork kidney cell line
L-MDR human MDR1 transfected LLC-PK1 cells
LoVo human tumour cell line
m multiplet (in NMR)
MDR1 Multidrug resistance protein 1
MeCN acetonitrile
min minute(s)
MOLM-13 human tumour cell line
MS mass spectrometry
MTT 3-(4,5-dimethylthiazol-2-yl)-2,5-diphenyl-2H-tetrazolium bromide 3
MV-4-11 human tumour cell line
NCI-H292 human tumour cell line
NMR nuclear magnetic resonance spectrometry
NMRI mouse strain originating from the Naval Medical Research Institute (NMRI)
NB4 human tumour cell line
PBS phosphate-buffered salt solution
P-gp P-glycoprotein, a transporter protein
PNGaseF enzyme for cleaving sugar
RT room temperature
$R_t$ retention time (in HPLC)
s singlet (in NMR)
SCID mice test mice with severe combined immunodeficiency
t triplet (in NMR)

TEMPO (2,2,6,6-tetramethylpiperidin-1-yl)oxyl
tert Tertiary
TFA trifluoroacetic acid
THF Tetrahydrofuran
THP-1 human tumour cell line
UV ultraviolet spectrometry
Z Benzyloxycarbonyl
HPLC and LC-MS Methods:
Method 1 (LC-MS):
 Instrument: Waters ACQUITY SQD UPLC System; column: Waters Acquity UPLC HSS T3 1.8μ50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm.
Method 2 (LC-MS):
 MS instrument type: Waters Synapt G2S; UPLC instrument type: Waters Acquity I-CLASS; column: Waters, BEH300, 2.1×150 mm, C18 1.7 μm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm
Method 3 (LC-MS):
 MS instrument: Waters (Micromass) QM; HPLC instrument: Agilent 1100 Series; column: Agilent ZORBAX Extend-C18 3.0×50 mm 3.5-micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm
Method 4 (LC-MS):
 MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm
Method 5 (LC-MS):
 Instrument: Waters ACQUITY SQD UPLC System; column: Waters Acquity UPLC HSS T3 1.8μ50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A oven: 50° C.; flow rate: 0.35 ml/min; UV detection: 210-400 nm.
Method 6 (LC-MS):
 Instrument: Micromass Quattro Premier with Waters UPLC Acquity; column: Thermo Hypersil GOLD 1.9μ50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.
Method 7 (LC-MS):
 Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.
Method 8 (LC-MS):
 MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm
Method 9: LC-MS-Prep Purification Method for Examples 181-191 (Method LIND-LC-MS-Prep)
 MS instrument: Waters, HPLC instrument: Waters (column Waters X-Bridge C18, 19 mm×50 mm, 5 μm, mobile phase A: water+0.05% ammonia, mobile phase B: acetonitrile (ULC) with gradient; flow rate: 40 ml/min; UV detection: DAD; 210-400 nm).
or
 MS instrument: Waters, HPLC instrument: Waters (column Phenomenex Luna 5μ C18(2) 100A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).
Method 10: LC-MS Analysis Method for Examples 181-191 (LIND_SQD_SB_AQ)
 MS instrument: Waters SQD; Instrument HPLC: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.
Method 11 (HPLC):
Instrument: HP1100 Series
column: Merck Chromolith SpeedROD RP-18e, 50-4.6 mm, Cat.
 No. 1.51450.0001, precolumn Chromolith Guard Cartridge Kit, RP-18e,
 5-4.6 mm, Cat. No. 1.51470.0001
gradient: flow rate 5 ml/min
 injection volume 5 μl
solvent A: HClO4 (70% strength) in water (4 ml/l)
solvent B: acetonitrile
start 20% B
0.50 min 20% B
3.00 min 90% B
3.50 min 90% B
3.51 min 20% B
4.00 min 20% B
column temperature: 40° C.
wavelength: 210 nm
Method 12 (LC-MS):
 MS instrument type: Thermo Scientific FT-MS; UHPLC+ instrument type: Thermo Scientific UltiMate 3000; column: Waters, HSST3, 2.1×75 mm, C18 1.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm
Method 13: (LC-MS):
 MS instrument: Waters (Micromass) Quattro Micro; Instrument Waters UPLC Acquity; column: Waters BEH C18 1.7μ50×2.1 mm; mobile phase A: 1 l of water+0.01 mol ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm All reactants or reagents whose preparation is not described explicitly hereinafter were purchased commercially from generally accessible sources. For all other reactants or reagents whose preparation likewise is not described Starting Materials and Intermediates:
Intermediate C52

(1R)-1-[1-Benzyl-4-(2,5-difluorophenyl)-1H-pyrrol-2-yl]-2,2-dimethylpropan-1-amine

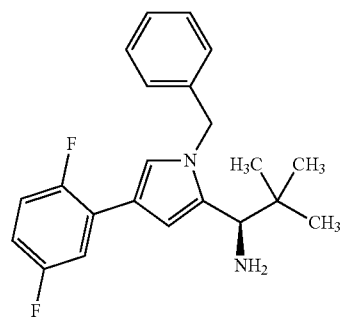 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate.

The two combined reactions were purified by preparative RP-HPLC (column: Daiso 300×100; 10µ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1'-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was purified by silica gel chromatography (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate. LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese (IV) oxide were added, and the mixture was stirred at RT for 48 h. Another 2.20 g (21.47 mmol) of manganese (IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphinamide were initially charged in 403.0 ml of absolute THF, and 67.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)—N—{(E/Z)-[1-benzyl-4-(2,5-difluorophenyl)-1H-pyrrol-2-yl]methylene}-2-methylpropane-2-sulphinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)—N—{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 [M+H]$^+$.

28.00 g (61.05 mmol) of (R)—N—{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 [M−NH$_2$]$^+$, 709 [2 M+H]$^+$.

$^1$H-NMR (400 MHz, DMSO-d$_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic Acid

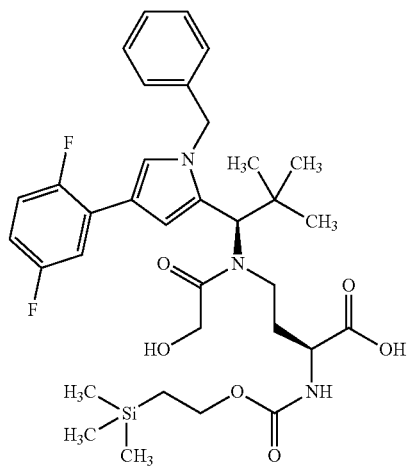 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 8.99 g (24.5 mmol) of Intermediate L57 dissolved in 175 ml of DCM were added and the reaction was stirred at RT for a further 45 min. The reaction was then diluted with 300 ml of DCM and washed twice with 100 ml of sodium bicarbonate solution and once with saturated NaCl solution. The organic phase was dried over magnesium sulphate, the solvent was evaporated under reduced pressure and the residue was dried under high vacuum. The residue was then purified by preparative RP-HPLC (column: Chromatorex C18). After combination of the appropriate fractions, the solvent was evaporated under reduced pressure and the residue was dried under high vacuum. This gave 4.6 g (61% of theory) of methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): $R_t$=1.97 min; MS (ESIpos): m/z=614 (M+H)$^+$.

2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% strength citric acid, twice with 300 ml of saturated sodium bicarbonate solution and once with 100 ml of saturated sodium chloride solution and then dried over magnesium sulphate and concentrated. Drying under high vacuum gave 2.17 g (79% of theory) of the protected intermediate.

LC-MS (Method 1): $R_t$=1.48 min; MS (ESIpos): m/z=714 (M+H)$^+$.

2.17 mg (2.64 mmol) of this intermediate were dissolved in 54 ml of THF and 27 ml of water, and 26 ml of a 2-molar lithium hydroxide solution were added. The mixture was stirred at RT for 30 min and then adjusted to a pH between 3 and 4 using 1.4 ml of TFA. The mixture was concentrated under reduced pressure. Once most of the THF had been distilled off, the aqueous solution was extracted twice with DCM and then concentrated to dryness under reduced pressure. The residue was purified by preparative HPLC (column: Chromatorex C18). After combination of the appropriate fractions, the solvent was evaporated under reduced pressure and the residue was lyophilized from acetonitrile/water. This gave 1.1 g (63% of theory) of the title compound.

LC-MS (Method 1): $R_t$=1.34 min; MS (ESIpos): m/z=656 (M−H)$^-$.

$^1$H-NMR (400 MHz, DMSO-d$_6$): δ [ppm]=0.03 (s, 9H), 0.58 (m, 1H), 0.74-0.92 (m, 11H), 1.40 (m, 1H), 3.3 (m, 2H), 3.7 (m, 1H), 3.8-4.0 (m, 2H), 4.15 (q, 2H), 4.9 and 5.2 (2d, 2H), 5.61 (s, 1H), 6.94 (m, 2H), 7.13-7.38 (m, 7H), 7.48 (s, 1H), 7.60 (m, 1H), 12.35 (s, 1H).

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

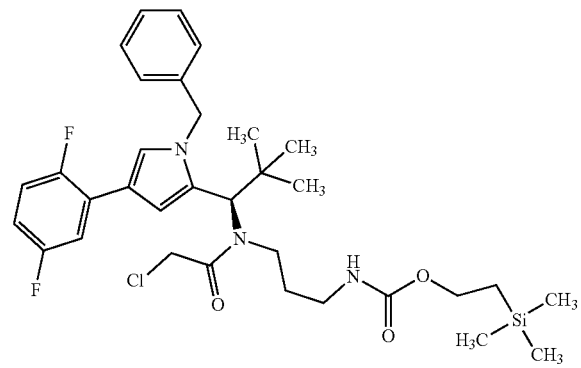 [SMILES: CC(C)(C)[C@H](c1cc(-c2cc(F)ccc2F)cn1Cc1ccccc1)N(CCCNC(=O)OCC[Si](C)(C)C)C(=O)CCl]

990.0 mg (2.79 mmol) of (1R)-1-[1-benzyl-4-(2,5-difluorophenyl)-1H-pyrrol-2-yl]-2,2-dimethylpropan-1-amine (intermediate C52) were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min. 698.1 mg (3.21 mmol) of 2-(trimethylsilyl)ethyl (3-oxopropyl)carbamate (Intermediate L58) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified on silica gel (mobile phase: dichloromethane/methanol=100:2). The solvents were evaporated under reduced pressure and the residue was dried under high vacuum. This gave 1.25 g (73% of theory) of the compound 2-(trimethylsilyl)ethyl[3-({(1R)-1-[1-benzyl-4-(2,5-difluorophenyl)-1H-pyrrol-2-yl]-2,2-dimethylpropyl}amino)propyl]c arbamate LC-MS (Method 1): R$_t$=1.09 min; MS (ESIpos): m/z=556 (M+H)$^+$.

908.1 mg (1.63 mmol) of 2-(trimethylsilyl)ethyl[3-({(1R)-1-[1-benzyl-4-(2,5-difluorophenyl)-1H-pyrrol-2-yl]-2,2-dimethylpropyl}amino)propyl]carbamate and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): R$_t$=1.53 min; MS (ESIneg): m/z=676 (M+HCOO$^-$)$^-$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1)

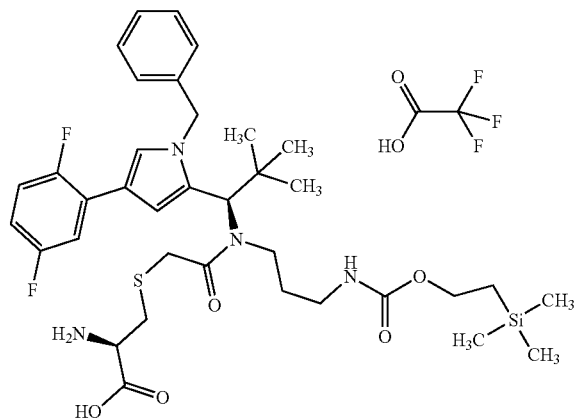 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](N)C(=O)O ; O=C(O)C(F)(F)F]

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): R$_t$=1.20 min; MS (ESIpos): m/z=717 (M+H)$^+$.

Intermediate C80

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine Trifluoroacetic Acid (1:1)

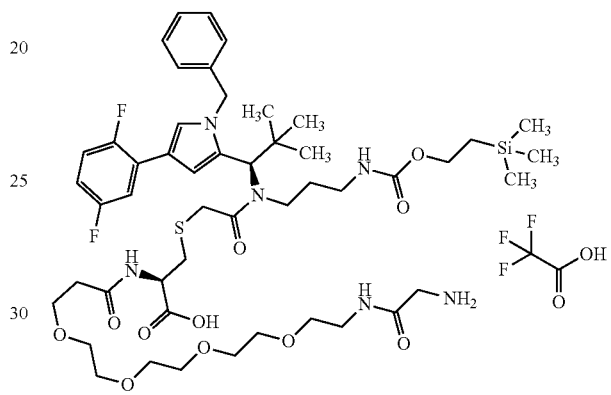

Under argon, 43.4 mg (95.1 µmol) of 1-({N-[(benzyloxy)carbonyl]glycyl}amino)-3,6,9,12-tetraoxapentadecan-15-oic acid (Intermediate L90) were initially charged in 2.5 ml of DMF, 14.6 mg (95.1 µmol) of 1-hydroxy-1H-benzotriazole hydrate, 30.5 mg (95.1 µmol) of (benzotriazol-1-yloxy)bisdimethylaminomethylium fluoroborate and 16.5 µl (95.1 µmol) of N,N-diisopropylethylamine were added and the mixture was stirred for 10 min. 79.0 mg (95.1 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) were dissolved in 2.5 ml of DMF, 49.5 µl (285.3 µmol) of N,N-diisopropylethylamine were added and the mixture was added to the reaction. The reaction mixture was stirred at RT for 2 h and purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 44.2 mg (40% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine.

LC-MS (Method 12): R$_t$=2.57 min; MS (ESIpos): m/z=1156 [M+H]+

60.2 mg (52.1 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine were suspended in 3.0 ml of ethanol, 6.0 mg of palladium on activated carbon (10%) were added and the mixture was hydrogenated with hydrogen at RT and standard pressure for 1 h. Twice, 6.0 mg of palladium on activated carbon (10%) were added and the mixture was hydrogenated with hydrogen at RT and standard pressure for 1 h. The catalyst was filtered off and the reaction mixture was freed from the solvent under reduced pressure and dried under high vacuum. The residue was purified by preparative RP-HPLC (column: Reprosil 125× 30; 10μ, flow rate: 50 ml/min, MeCN/water, 0.1% TFA). The solvents were evaporated under reduced pressure and the residue was dried under high vacuum. This gave 29.4 mg (50% of theory) of the title compound.

LC-MS (Method 5): $R_t$=3.77 min; MS (ESIpos): m/z=1021 [M+H]$^+$

Intermediate L1

Trifluoroacetic acid/N-(2-aminoethyl)-2-(2,5-dioxo-2,5-dihydro-1H-pyrrol-1-yl)acetamide (1:1)

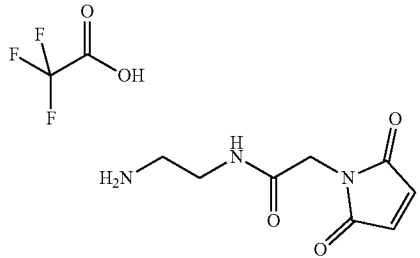 [SMILES: O=C(O)C(F)(F)F ; NCCNC(=O)CN1C(=O)C=CC1=O]

The title compound was prepared by classical methods of peptide chemistry from commercially available (2,5-dioxo-2,5-dihydro-1H-pyrrol-1-yl)acetic acid and tert-butyl (2-aminoethyl)carbamate. HPLC (Method 11): $R_t$=0.19 min;

LC-MS (Method 1): $R_t$=0.17 min; MS (ESIpos): m/z=198 (M+H)$^+$.

Intermediate L57

Methyl (2S)-4-oxo-2-({[2-(trimethylsilyl)ethoxy]carbonyl}amino)butanoate

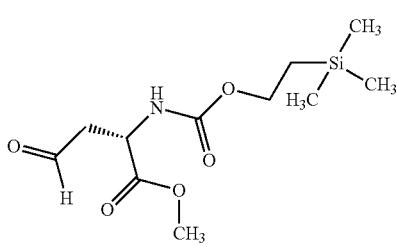 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10μ, flow rate: 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid.

LC-MS (Method 1): $R_t$=0.89 min; MS (ESIneg): m/z=290 (M−H)$^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C. and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed in each case once with saturated sodium bicarbonate solution and saturated NaCl solution. The organic phase was dried over magnesium sulphate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength $Na_2S_2O_3$ solution, 10% strength citric acid solution and saturated sodium bicarbonate solution. The organic phase was dried over magnesium sulphate and the solvent was evaporated under reduced pressure. This gave 565.7 mg (97% of theory) of the title compound.

$^1$H-NMR (400 MHz, DMSO-$d_6$): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L58

2-(Trimethylsilyl)ethyl (3-oxopropyl)carbamate

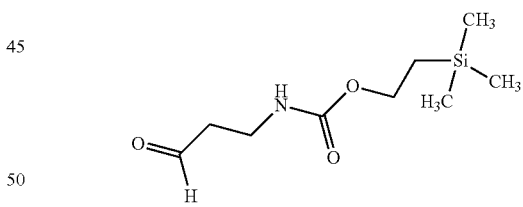

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure. The residue 2-(trimethylsilyl)ethyl (3-hydroxypropyl)carbamate (996.4 mg, 79% of theory) was dried under high vacuum and used without further purification in the next step of the synthesis.

807.0 mg (3.68 mmol) of 2-(trimethylsilyl)ethyl (3-hydroxypropyl)carbamate were initially charged in 15.0 ml of chloroform and 15.0 ml of 0.05N potassium carbonate/

0.05N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L74

3-[2-[2-[2-[2-[[2-(2,5-Dioxopyrrol-1-yl)acetyl]amino]ethoxy]ethoxy]ethoxy]ethoxy]propanoic Acid

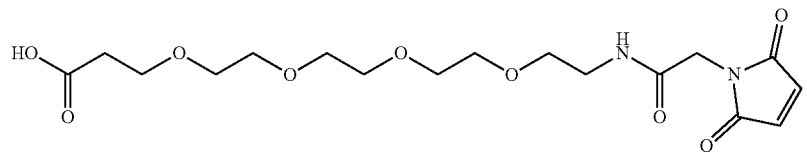 [SMILES: O=C(O)CCOCCOCCOCCOCCNC(=O)CN1C(=O)C=CC1=O]

107 mg (0.335 mmol) of tert-butyl 3-[2-[2-[2-(2-aminoethoxy)ethoxy]ethoxy]ethoxy]propanoate and 93 mg (0.369 mmol) of (2,5-dioxopyrrolidin-1-yl) 2-(2,5-dioxopyrrol-1-yl)acetate were dissolved in 5 ml of dimethylformamide, and 0.074 ml (0.671 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 133 mg (86%, purity 100%) of tert-butyl 3-[2-[2-[2-[2-[[2-(2,5-dioxopyrrol-1-yl)acetyl]amino]ethoxy]ethoxy]ethoxy]ethoxy]propanoate.

LC-MS (Method 1): $R_t$=0.82 min; MS (ESIpos): m/z=459 (M+H)$^+$.

0.5 ml of TFA was added to a solution of tert-butyl 3-[2-[2-[2-[2-[[2-(2,5-dioxopyrrol-1-yl)acetyl]amino]ethoxy]ethoxy]ethoxy]ethoxy]propanoate (130 mg, 0.284 mmol) in 5 ml of dichloromethane. The reaction mixture was stirred at RT overnight. The reaction mixture was concentrated under reduced pressure and the residue was taken up in water and lyophilized. The residue was used further without further purification. This gave 102 mg (90%, purity 100%) of the title compound.

LC-MS (Method 1): $R_t$=0.52 min; MS (ESIpos): m/z=402 (M+H)$^+$.

Intermediate L90

1-({N-[(Benzyloxy)carbonyl]glycyl}amino)-3,6,9,12-tetraoxapentadecan-15-oic Acid 118 mg (566 μmol) of N-[(benzyloxy)carbonyl]glycine were initially charged in 5.0 ml of DMF, 200 mg (622 μmol) of tert-butyl 1-amino-3,6,9,12-tetraoxapentadecan-15-oate, 130 mg (849 μmol) of 1-hydroxy-1H-benzotriazole hydrate and 130 mg (679 μmol) of 1-(3-dimethylaminopropyl)-3-ethylcarbodiimide hydrochloride were added and the mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate. The solvents were evaporated under reduced pressure and the residue was dried under high vacuum. This gave 274 mg (95% of theory) of tert-butyl 1-({N-[(benzyloxy)carbonyl]glycyl}amino)-3,6,9,12-tetraoxapentadecan-15-oate.

LC-MS (Method 12): $R_t$=1.69 min; MS (ESIpos): m/z=513 (M+H)$^+$.

820 μl (11 mmol) of TFA were added to a solution of 274 mg (535 μmol) of tert-butyl 1-({N-[(benzyloxy)carbonyl]glycyl}amino)-3,6,9,12-tetraoxapentadecan-15-oate in 5.0 ml of dichloromethane. The reaction mixture was stirred at RT for 3 h. The reaction mixture was concentrated under reduced pressure and the residue was taken up in water and lyophilized. This gave 262 mg (100% of theory) of the title compound.

LC-MS (Method 12): $R_t$=1.12 min; MS (ESIpos): m/z=457 (M+H)$^+$.

Intermediate F104

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

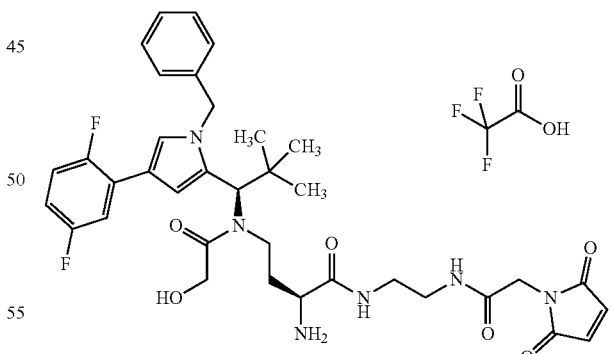

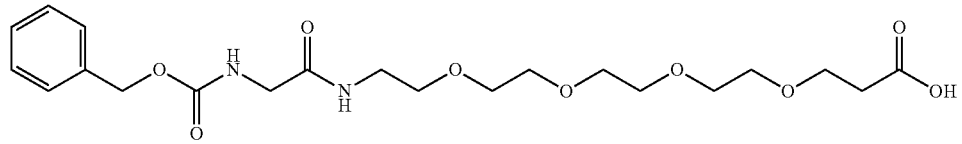 [SMILES: O=C(O)CCOCCOCCOCCOCCNC(=O)CNC(=O)OCc1ccccc1]

15 mg (0.023 mmol) of Intermediate C58 were initially reacted with 11 mg (0.036 mmol) of Intermediate L1 in the presence of 13 mg (0.034 mmol) of HATU and 10 µl of N,N-diisopropylethylamine. After 60 min of stirring at RT, the mixture was concentrated and the residue was purified by preparative HPLC. This gave 12.3 mg (63% of theory) of the protected intermediate.

LC-MS (Method 1): $R_t$=1.3 min; MS (EIpos): m/z=837 [M+H]$^+$.

In the second step, this intermediate was dissolved in 3 ml of 2,2,2-trifluoroethanol. 12 mg (0.088 mmol) of zinc chloride were added, and the reaction was stirred at 50° C. for 2 h. 26 mg (0.088 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 8.1 mg (68% of theory) of the title compound.

LC-MS (Method 1): $R_t$=0.89 min; MS (ESIpos): m/z=693 (M+H)$^+$.

Intermediate F257

R-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[18-(2,5-dioxo-2,5-dihydro-1H-pyrrol-1-yl)-17-oxo-4,7,10,13-tetraoxa-16-azaoctadecan-1-oyl]-L-cysteine/ trifluoroacetic Acid (1:1)

MeCN/water/0.1% TFA). The solvents were evaporated under reduced pressure and the residue was dried under high vacuum. This gave 17.4 mg (26%) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine.

LC-MS (Method 6): $R_t$=1.34 min; MS (ESIpos): m/z=1101 (M+H)$^+$.

17 mg (0.02 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine were dissolved in 1.0 ml of trifluoroethanol, and 6.3 mg (0.05 mmol) of zinc dichloride were added. The reaction mixture was stirred at 50° C. overnight. 13.5 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 7.6 mg (46%) of the title compound.

LC-MS (Method 1): $R_t$=0.91 min; MS (ESIpos): m/z=957 (M+H)$^+$.

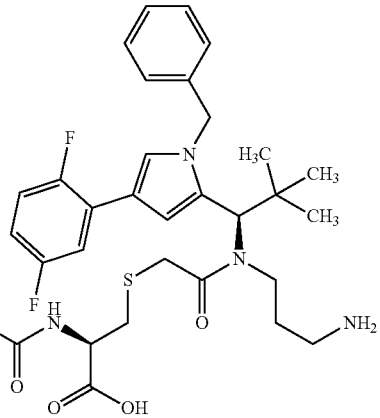

50.0 mg (0.06 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) and 29 mg (0.07 mmol) of 3-[2-[2-[2-[2-[[2-(2,5-dioxopyrrol-1-yl)acetyl]amino]ethoxy]ethoxy]ethoxy]ethoxy]propanoic acid (Intermediate L74) were dissolved in 3.0 ml of DMF, and 27.3 mg (0.07 mmol) of HATU and 23.3 mg (0.18 mmol) of N,N-diisopropylethylamine were added. The reaction mixture was stirred at RT for 2 hours. The reaction mixture was purified directly by preparative RP-HPLC (column: Reprosil 125×30; 10µ, flow rate: 50 ml/min, B: Preparation of Antibody Drug Conjugates (ADC)

B-1. General Process for Generating Anti-CD123 Antibodies

The anti-CD123 antibodies were obtained by CDR grafting. The sequence of the 7G3 antibody (EP2426148) represents the starting point of the humanized antibodies such as TPP-5969, TPP-8987 and TPP-9476. Bispecific scFv immunofusion proteins based on 12F1 are disclosed in WO 2013/173820. Based on the publication of the sequences of the variable regions (VH and VL) of 12F1 (WO 2013/173820), the following antibody sequences were obtained by fusion of the variable domains of the donor immunoglobulin (VH and VL) with the constant regions of a human antibody. A chimeric variant of 12F1 was generated. Humanized anti-CD123 antibodies were obtained by CDR grating representing the starting point of the humanized antibodies such as TPP-8988 and TPP-9342.

Humanization

The murine antibody sequence of the 7G3 antibody was humanized by transferring the CDRs into a human antibody skeleton. For the definition of the CDRs according to Kabat, see Andre C. R. Martin, "Protein sequence and structure analysis of antibody variable domains" in Antibody Engineering (Springer Lab Manuals), Eds.: Duebel, S. and Kontermann, R., Springer-Verlag, Heidelberg. After comparison of the murine frame sequences (without CDRs) with human germline sequences, a similar frequently occurring human frame sequence was selected. In this case, it was the heavy chain IGHV1-46-01 with the J sequence IGHJ4-03 and the light chain IGKV4-1-01 with the J segment IGKJ2. The germline sequences originated from the VBASE2 database (Retter I, Althaus H H, Münch R, Müller W: VBASE2, an integrative V gene database. Nucleic Acids Res. Jan. 1, 2005; 33 (Database issue):D671-4). The sequences were named using the IMGT system (Lefranc, M. P., Giudicelli, V., Ginestoux, C., Jabado-Michaloud, J., Folch, G., Bellahcene, F., Wu, Y., Gemrot, E., Brochet, X., Lane, J., Regnier, L., Ehrenmann, F, Lefranc, G. and Duroux, P. IMGT®, the international ImMunoGeneTics information System®. Nucl. Acids Res, 37, D1006-D1012 (2009); doi: 10.1093/nar/gkn838). The antibody variants TPP-5969, TPP-8987 and TPP-9476 described herein carry various point mutations differing from the human germline sequence which may influence their properties. Besides the chimeric antibody TPP-6013 humanized antibodies were obtained by transferring the CDRs into a human antibody skeleton as TPP-8988 and TPP-9342

B-2. General Process for Expressing Anti-CD123 Antibodies in Mammalian Cells

The antibodies, for example TPP-6013, TPP-5969, TPP-8987, TPP-8988, TPP-9476 and TPP-9342 were produced in transient cultures of mammalian cells, as described by Tom et al., Chapter 12 in Methods Express: Expression Systems, edited by Micheal R. Dyson and Yves Durocher, Scion Publishing Ltd, 2007.

B-3. General Process for Purifying Antibodies from Cell Supernatants

The antibodies, for example TPP-8987 and TPP-8988, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The antibodies were furthermore characterized by their binding affinity to soluble IL3Ralpha (obtained from R&D Systems) via BIAcore analysis. To determine the cell binding characteristics of the anti-CD123 antibodies, binding was measured by flow cytometry on CD123-positive cancer cell line MOLM-13.

B-4. General Process for Coupling to Cysteine Side Chains

The following antibodies were used for the coupling reactions:

TPP-5969
TPP-6013
TPP-8987
TPP-8988
TPP-9476

The coupling reactions were usually carried out under argon.

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 10 mg/ml to 15 mg/ml, and the mixture was stirred at RT for 30 min. For this purpose, the solution of the respective antibody used can be employed at the concentrations stated in the working examples, or it may optionally also be diluted with PBS buffer to about half of the stated starting concentrations in order to get into the preferred concentration range. Subsequently, depending on the intended loading, from 2 to 12 equivalents, preferably about 5-10 equivalents of the maleinimide precursor compound to be coupled were added as a solution in DMSO. Here, the amount of DMSO should not exceed 10% of the total volume. The reaction was stirred for 60-240 min at RT and then diluted with PBS buffer which had been adjusted to pH 8 beforehand. The solution was then applied to PBS pH 8-equilibrated PD 10 columns (Sephadex® G-25, GE Healthcare) and eluted with PBS pH 8 buffer. The eluate may be diluted with PBS buffer pH 8. This solution was stirred at RT under argon overnight. The solution was then rebuffered to pH 7.2. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

The ADCs shown in the examples may also be present to a lesser or higher degree in the form of the closed succinamides attached to the antibodies.

In the structural formulae shown, $AK_{TPP\text{-}XXXX}$ or AK has the meaning

AK=anti-CD123 antibody (partially reduced)-S$§^1$ $AK_{TPP5969}$=anti-CD123 TPP-5969 (partially reduced)-S$§^1$ $AK_{TPP6013}$=anti-CD 123 TPP-6013 (partially reduced)-S$§^1$ $AK_{TPP8987}$=anti-CD 123 TPP-8987 (partially reduced)-S$§^1$ $AK_{TPP8988}$=anti-CD 123 TPP-8988 (partially reduced)-S$§^1$ $AK_{TPP9476}$=anti-CD123 TPP-9476 (partially reduced)-S$§^1$ where $§^1$ represents the linkage to the succinimide group or to any isomeric hydrolysed open-chain succinamides or the alkylene radical resulting therefrom, and S represents the sulphur atom of a cysteine residue of the partially reduced antibody.

B-6a. General Process for Preparing Isomeric Open Succinamide-Cysteine Adducts:

In an exemplary embodiment, 68 µmol of the maleinimide precursor compounds described above were taken up in 15 ml of DMF, and with 36 mg (136 µmol) of N-{[2-(trimethylsilyl)ethoxy]carbonyl}-L-cysteine were added. The reaction mixture was stirred at RT for ~20 h, then concentrated under reduced pressure and then purified by preparative HPLC. The appropriate fractions were combined and the solvents were evaporated under reduced pressure, and the residue was then dissolved in 15 ml of THF/water 1:1. 131 µl of a 2 M aqueous lithium hydroxide solution were added and the reaction was stirred at RT for 1 h. The reaction was then neutralized with a 1 M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave the hydrolysed open sulphanylsuccinamides as a regioisomer mixture.

Further Purification and Characterization of the Conjugates According to the Invention After the reaction, in some instances the reaction mixture was concentrated, for example by ultrafiltration, and then desalted and purified by chromatography, for example using a Sephadex® G-25 column: Elution was carried out, for example, with phosphate-buffered saline (PBS). The solution was then sterile filtered and frozen. Alternatively, the conjugate can be lyophylized.

B-7. Determination of the Antibody, the Toxophor Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophor loading of the PBS buffer solutions obtained of the conjugates described in the working examples was determined as follows:

Determination of toxophor loading of lysine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

The toxophor loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1 ml/min with the following gradient: 0 min, 25% B; 3 min, 25% B; 28 min, 50% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophor (L1) and the heavy chains with one, two and three toxophors (H1, H2, H3).

Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks. In individual cases, it may not be possible to determine the toxophor load accurately owing to co-elutions of some peaks.

In the cases where light and heavy chains could not be separated sufficiently by HPLC, determination of toxophor loading of cysteine-linked conjugates was carried out by mass spectrometric determination of the molecular weights of the individual conjugate species at light and heavy chain Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated for one hour at 55° C. and analysed by mass spectrometry after online desalting using ESI-MicroTof$_Q$ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks.

To determine the proportion of the open cysteine adduct, the molecular weight area ratio of closed to open cysteine adduct (molecular weight delta 18 Dalton) of all singly conjugated light and heavy chain variants was determined. The mean of all variants yielded the proportion of the open cysteine adduct.

B-8. Checking the Antigen-Binding of the ADCs

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

Metabolite Embodiments

Example M20

(1R,4R,27R,33R)-1-Amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic acid/trifluoroacetic Acid (1:2)

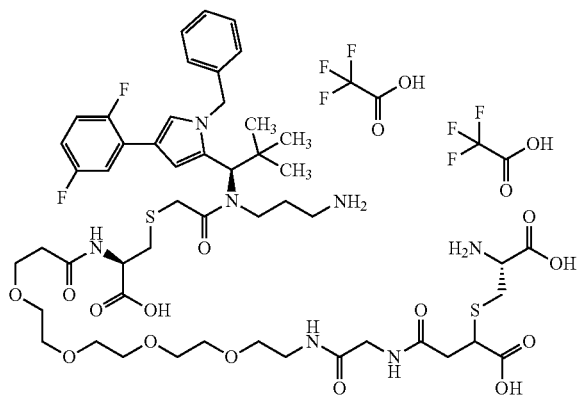

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate.

408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 (M−H)⁻.

3.66 mg (8.93 μmol) of 4-methoxy-3-{[(2R)-3-methoxy-3-oxo-2-({[2-(trimethylsilyl)ethoxy]carbonyl}amino)propyl]sulphanyl}-4-oxobutanoic acid were coupled in the presence of 3.66 mg (8.93 μmol) of HATU and 1.6 μl (15 μmol) of 4-methylmorpholine with 13.0 mg (7.44 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.9 mg (37% of theory) of the fully protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11R)-8,11-bis(methoxycarbonyl)-2,2-dimethyl-6,13-dioxo-5-oxa-10-thia-7-aza-2-silatridecan-13-yl]glycyl}amino)-4,7,10,13-tetraoxapentadecan-1-oyl]-L-cysteine. 3.90 mg (2.76 μmol) of this intermediate were then stirred at RT with 35 μl of a 2-molar lithium hydroxide solution in 1.0 ml of THF/water 3:1 for 15 min, resulting in the cleavage of both methyl ester groups. Purification by HPLC gave 3.60 mg (94% of theory) of the dicarboxylic acid derivative.

LC-MS (Method 5): $R_t$=4.83 min; MS (ESIpos): m/z=1385 [M+H]⁺.

Finally, 3.6 mg (2.6 μmol) of this intermediate were completely deprotected with zinc chloride in trifluoroethanol as described above. The residue was purified by preparative HPLC. Concentration of the appropriate fractions and lyophilization of the residue from acetonitrile/water gave 1.92 mg (55% of theory) of the title compound.

LC-MS (Method 5): $R_t$=2.72 min; MS (ESIneg): m/z=1094 [M−H]⁻.

Example M21

(2R,24S,27R)-27-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-24-(carboxymethyl)-4,20,23-trioxo-7,10,13,16-tetraoxa-25-thia-3,19,22-triazaoctacosane-1,28-dioic acid/trifluoroacetic Acid (1:2)

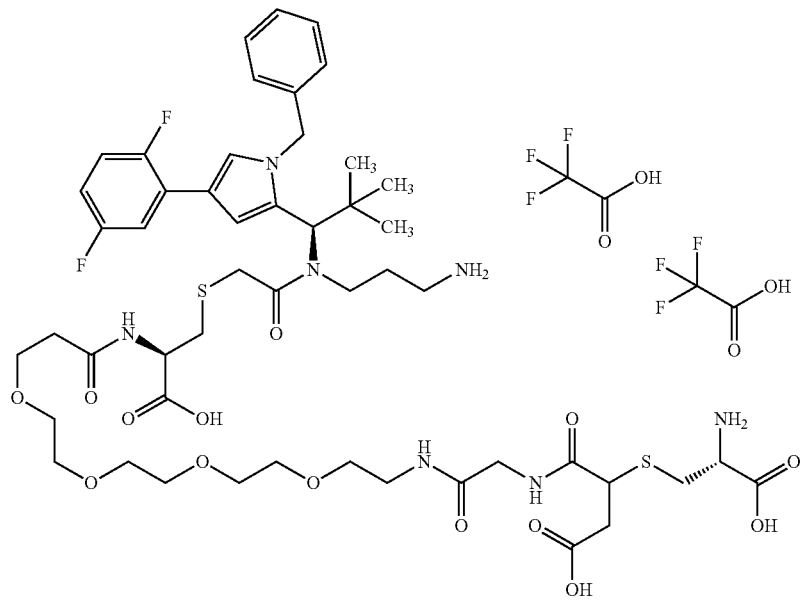 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CNC(=O)C(CC(=O)O)SC[C@H](N)C(=O)O)C(=O)O ; O=C(O)C(F)(F)F ; O=C(O)C(F)(F)F]

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 $(M+H)^+$.

4.36 mg (10.3 µmol) of 4-ethoxy-2-{[(2R)-3-methoxy-3-oxo-2-({[2-(trimethylsilyl)ethoxy]carbonyl}amino)propyl]sulphanyl}-4-oxobutanoic acid were coupled in the presence of 3.92 mg (10.3 µmol) of HATU and 1.9 µl (17 µmol) of 4-methylmorpholine with 15.0 mg (8.59 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.6 mg (26% of theory) of the fully protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11 S)-11-(2-ethoxy-2-oxoethyl)-8-(methoxycarbonyl)-2,2-dimethyl-6,12-dioxo-5-oxa-10-thia-7-aza-2-siladodecan-12-yl]glycyl}amino)-4,7,10,13-tetraoxapentadecan-1-oyl]-L-cysteine.

6.20 mg (2.82 µmol) of this intermediate were then stirred at RT with 35 µl of a 2-molar lithium hydroxide solution in 1.0 ml of THF/water 1:1 for 15 min, resulting in the cleavage of both ester groups. Acidification and purification by HPLC gave 3.60 mg (92% of theory) of the dicarboxylic acid derivative.

LC-MS (Method 5): $R_t$=4.71 min; MS (ESIpos): m/z=1385 $[M+H]^+$.

Finally, 3.60 mg (1.69 µmol) of this intermediate were completely deprotected with zinc chloride in trifluoroethanol as described above. The residue was purified by preparative HPLC. Concentration of the appropriate fractions and lyophilization of the residue from acetonitrile/water gave 0.88 mg (39% of theory) of the title compound.

LC-MS (Method 5): $R_t$=2.72 min; MS (ESIneg): m/z=1094 $[M-H]^-$.

Working Examples ADCs

The ADCs shown in the structural formulae of the Working examples, which were coupled to the cysteine side chains of the antibodies via maleimide radicals, are, depending on the linker and the coupling procedure, mainly present in the ring-opened forms shown in each case. However, the preparation(s) may comprise a small proportion of the ring-closed form.

The ring-closed form is:

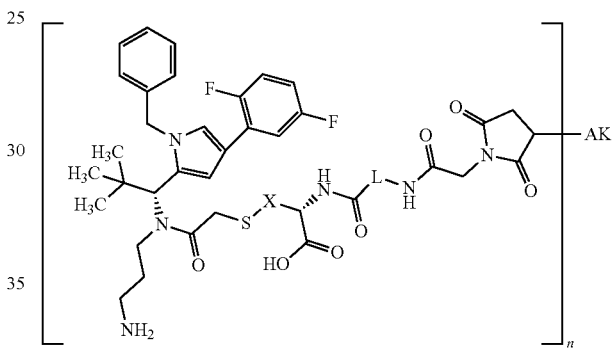

Ref 208 m1

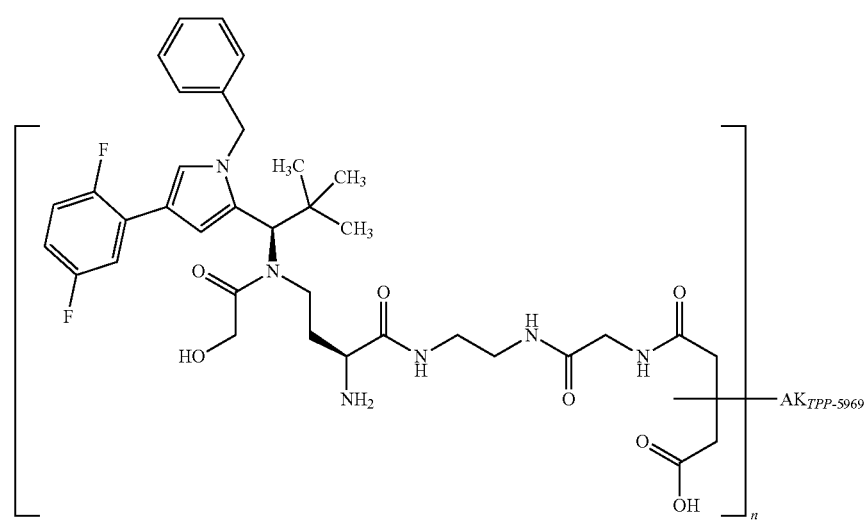

Under argon, a solution of 1.4 mg of TCEP in 0.83 ml of PBS buffer was added to 250 mg of Anti-CD123 TPP-5969 in 21.7 ml of PBS (c=11.5 mg/ml). The reaction was stirred at RT for 30 min, and 10.76 mg (0.0133 mmol) of Intermediate F104 dissolved in 2500 μl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 125 ml with PBS buffer (pH 7.2), concentrated by ultracentrifugation, rediluted with PBS buffer (pH 7.2) and reconcentrated again. The ADC batch obtained was characterized as follows:

Protein concentration: 9.79 mg/ml
Drug/mAb ratio: 2.9
Ref 208m3

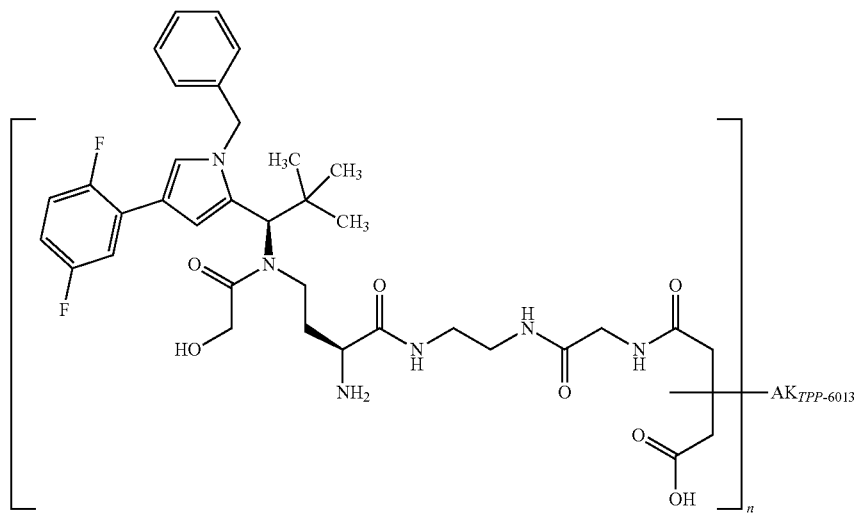

Under argon, a solution of 1.4 mg of TCEP in 0.83 ml of PBS buffer was added to 250 mg of Anti-CD123 TPP-6013 in 21.7 ml of PBS (c=11.5 mg/ml). The reaction was stirred at RT for 30 min, and 10.76 mg (0.0133 mmol) of Intermediate F104 dissolved in 2500 μl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 125 ml with PBS buffer (pH 7.2), concentrated by ultracentrifugation, rediluted with PBS buffer (pH 7.2) and reconcentrated again. The ADC batch obtained was characterized as follows:

Protein concentration: 11.06 mg/ml
Drug/mAb ratio: 3.4

Ref 257 m1

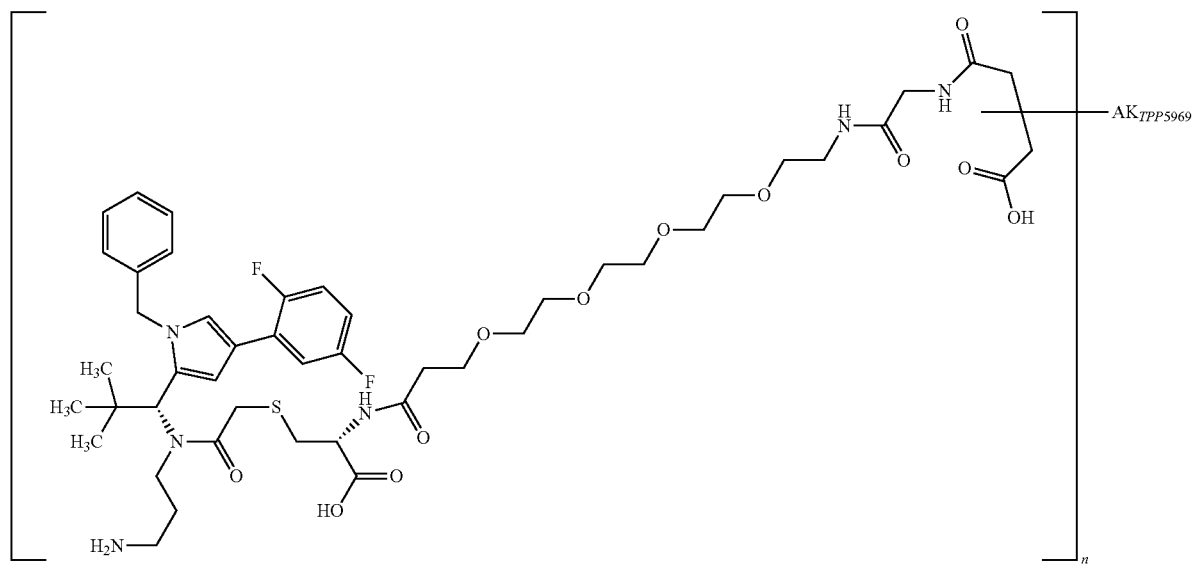

Under argon, a solution of 1.4 mg of TCEP in 0.83 ml of PBS buffer was added to 250 mg of Anti-CD123 TPP-5969 in 21.7 ml of PBS (c=11.5 mg/ml). The reaction was stirred at RT for 30 min, and 8.92 mg (0.0083 mmol) of Intermediate F257 dissolved in 2500 µl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 125 ml with PBS buffer (pH 7.2), concentrated by ultracentrifugation, rediluted with PBS buffer (pH 7.2) and reconcentrated again. The ADC batch obtained was characterized as follows:

Protein concentration: 11.27 mg/ml
Drug/mAb ratio: 3.6

Ref 257m3

Under argon, a solution of 1.4 mg of TCEP in 0.83 ml of PBS buffer was added to 250 mg of Anti-CD123 TPP-6013 in 21.7 ml of PBS (c=11.5 mg/ml). The reaction was stirred at RT for 30 min, and 8.92 mg (0.0083 mmol) of Intermediate F257 dissolved in 2500 µl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 125 ml with PBS buffer (pH 7.2), concentrated by ultracentrifugation, rediluted with PBS buffer (pH 7.2) and reconcentrated again. The ADC batch obtained was characterized as follows:

Protein concentration: 13.36 mg/ml
Drug/mAb ratio: 3.3

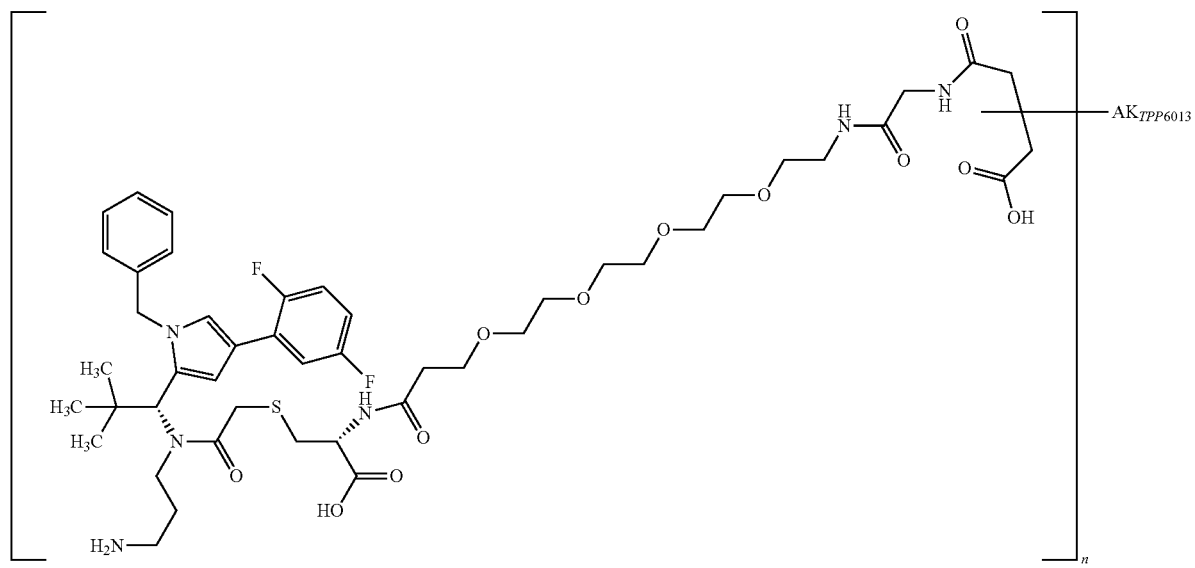

Example 1a

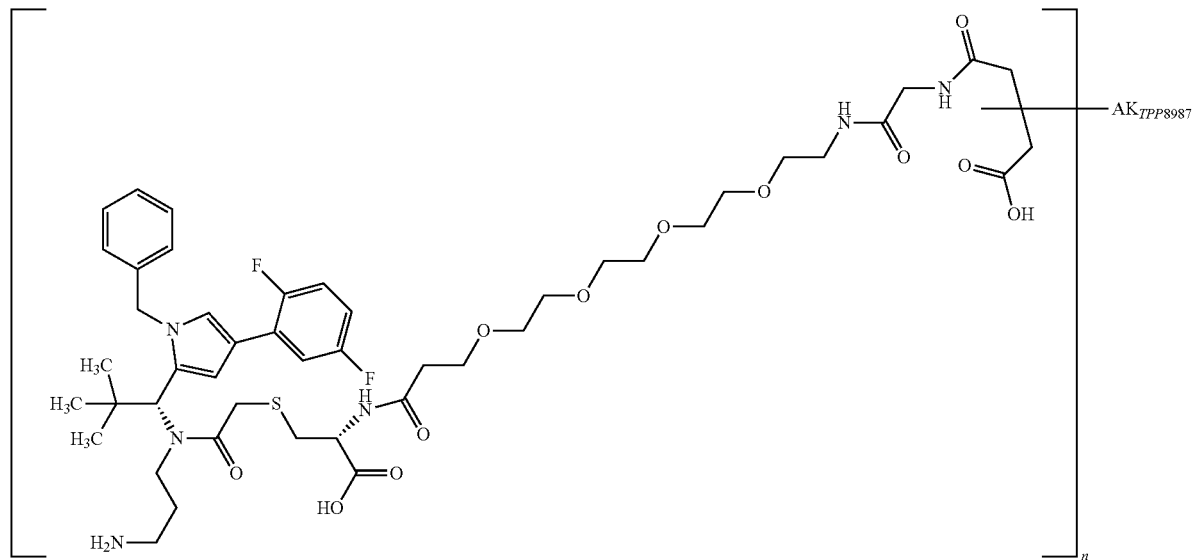

Under argon, a solution of 0.057 mg of TCEP in 100 μl of PBS buffer was added to 10 mg of anti-CD123 TPP-8987 in 900 μl of PBS (c=11.11 mg/ml). The reaction was stirred at RT for 30 min. 0.357 mg (0.00033 mmol) of Intermediate F257 dissolved in 100 μl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 14 ml with PBS buffer (pH 7.2), concentrated by ultracentrifugation, rediluted with PBS buffer (pH 7.2) and reconcentrated again. The ADC batch obtained was characterized as follows:

Protein concentration: 6.30 mg/ml

Drug/mAb ratio: 3.1

Example 1b

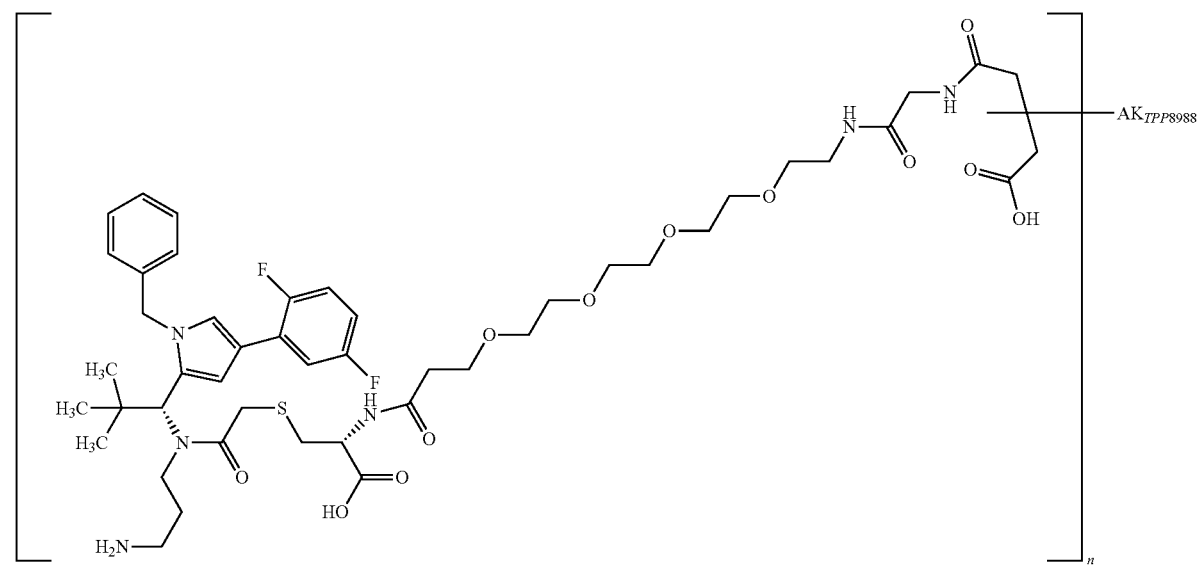

Under argon, a solution of 0.143 mg of TCEP in 250 µl of PBS buffer was added to 25 mg of anti-CD123 TPP-8988 in 2500 µl of PBS (c=10.0 mg/ml). The reaction was stirred at RT for 30 min. 0.893 mg (0.00083 mmol) of Intermediate F257 dissolved in 250 µl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 14 ml with PBS buffer (pH 7.2), concentrated by ultracentrifugation, rediluted with PBS buffer (pH 7.2) and reconcentrated again. The ADC batch obtained was characterized as follows:

Protein concentration: 10.43 mg/ml

Drug/mAb ratio: 4.3

Example 1c

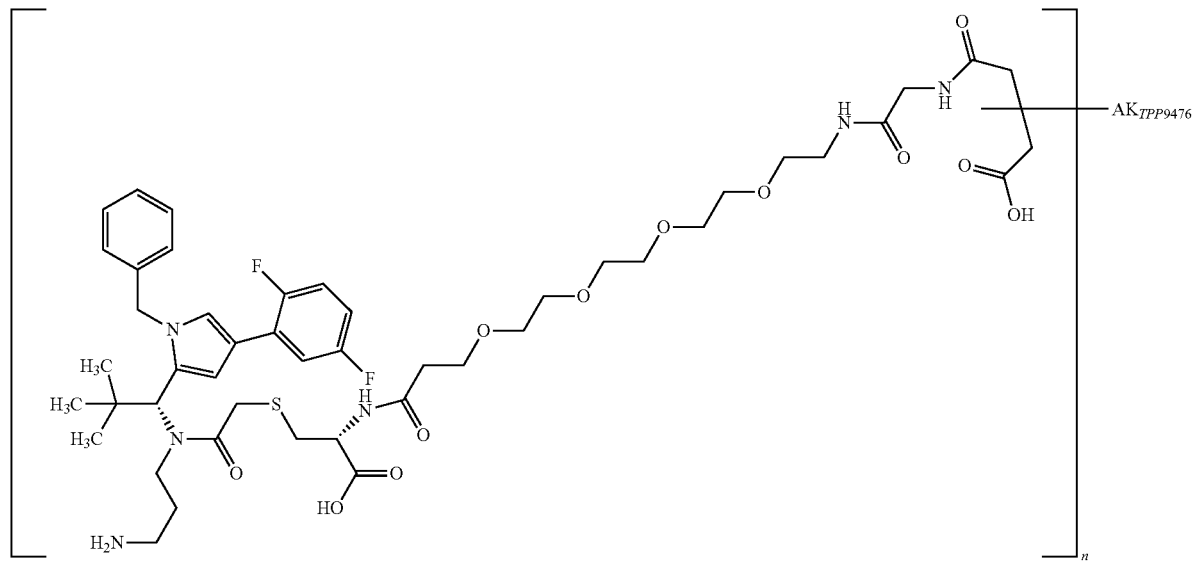

Under argon, a solution of 0.172 mg of TCEP in 300 µl of PBS buffer was added to 30 mg of anti-CD123 TPP-9476 in 3000 µl of PBS (c=10.0 mg/ml). The reaction was stirred at RT for 30 min. 1.071 mg (0.001 mmol) of Intermediate F257 dissolved in 300 µl of DMSO were then added. After a further 90 min of stirring at RT, the reaction was re-buffered to pH 8 using PD-10 columns (Sephadex® G-25, GE Healthcare). The eluate was stirred under argon at RT overnight and then re-buffered to pH 7.2 using PD-10 columns. The eluate was then diluted to 14 ml with PBS buffer (pH 7.2), concentrated by ultracentrifugation, rediluted with PBS buffer (pH 7.2) and reconcentrated again. The ADC batch obtained was characterized as follows:

Protein concentration: 11.04 mg/ml

Drug/mAb ratio: 4.4

C: Assessment of Biological Efficacy

The biological activity of the compounds according to the invention can be shown in the assays described below:

C-1a Determination of the Cytotoxic Effects of the ADCs Directed Against CD123

The analysis of the cytotoxic effects of the anti-CD123 ADCs and the corresponding metabolites was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Biochrom; #S0415).

MOLM-13: human acute monocytic leukaemia cells obtained from peripheral blood (AML-M5a), DSMZ, No. ACC 554, standard medium: RPMI 1640 (Gibco; #21875-059, stab. L-glutamine)+20% heat inactivated FCS (Gibco, No. 10500-064); CD123-positive.

THP-1: human monocytic leukaemia cells obtained from peripheral blood, ATCC, NO. TIB-202, standard medium: RPMI 1640 (Gibco; #21875-059, stab. L-glutamine)+10% heat inactivated FCS (Gibco, No. 10500-064)+2.5 g of glucose (20% glucose solution, Gibco, No. 19002); CD123-positive.

MV-4-11: human biphenotypic B myelomonocytic leukemia cells obtained from peripheral blood, ATCC-CRL-9591, standard medium: IMDM (ATCC: 30-2005), +10% heat inactivated FCS (Gibco, No. 10500-064); CD123-positive.

KG-1: human acute myeloid leukaemia cells obtained from bone marrow, DSMZ, No. ACC 14, standard medium: RPMI 1640 (Gibco; #21875-059, stab. L-glutamine)+10% heat inactivated FCS (Gibco, No. 10500-064)+2.5 g of glucose (20% glucose solution, Gibco, No. 19002); CD123-positive.

NB4: human acute promyelocytic leukemia cells obtained from bone marrow, DSMZ, No. ACC 207, standard medium: RPMI 1640+GlutaMAX I (Invitrogen 61870)+10% heat inactivated FCS (Gibco, No. 10500-064)+2.5 g of glucose (20% glucose solution, Gibco, No. 19002)+10 mM Hepes (Invitrogen 15630)+1 mM Sodium Pyruvate (Invitrogen 11360); CD123-negative The cells were cultivated by the standard method as stated by the American Tissue Culture Collection (ATCC) or the Leibniz-Institut DSMZ-Deutsche Sammlung von Mikroorganismen and Zellkulturen GmbH (DSMZ) for the cell lines in question.

MTT Assay

The cells were cultivated according to the standard method using the growth media listed under C-1. The test is carried out by detaching the cells with a solution of Accutase in PBS (Biochrom AG #L2143; in case of adherent cell), pelleting, resuspending in culture medium, counting and sowing into a 96-well culture plate with white bottom (Costar #3610) (NCI H292: 2500 cells/well; MOLM-13: 2000 cells/well; THP-1: 8000 cells/well; NB4: 7000 cells/well; KG-1: 5000 cells/well, MV-4-11: 5000 cells/well in a total volume of 100 µl). The cells were then incubated in an incubator at 37° C. and 5% carbon dioxide. After 6 h or 48 h (adherent cells) the medium was replaced. The antibody drug conjugates or the metabolites in 10 µl of culture medium in concentrations from $10^{-5}$ M to $10^{-13}$ M were then pipetted to the cells (in triplicate), and the assay was then incubated in an incubator at 37° C. and 5% carbon dioxide. After 96 h, the cell proliferation was detected using the MTT assay (ATCC, Manassas, Va., USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the $IC_{50}$ of the growth inhibition using the DRC (dose response curve). The proliferation of cells which were not treated with test substance but were otherwise identically treated was defined as the 100% figure.

Table 1 below lists the $IC_{50}$ values of representative working examples for different anti-CD123 antibodies from this assay:

TABLE 1

| Example | MOLM 13 $IC_{50}$ [M] MTT assay | THP-1 $IC_{50}$ [M] MTT assay | MV-4-11 $IC_{50}$ [M] MTT assay | NB4 IC50 [M] MTT assay |
|---|---|---|---|---|
| 1a | 6.86E-10 | | 4.11E-09 | 7.19E-08 |
| 1b | 1.67E-11 | | 5.19E-09 | |
| 1c | 1.37E-10 | | 9.33E-10 | |
| Ref 208m1 | 3.28E-09 | 1.03E-10 | | 1.73E-07 |
| Ref 208m3 | 1.21E-09 | 1.60E-09 | | 3.00E-07 |
| Ref 257m1 | 1.51E-09 | 5.96E-10 | | 5.00E-07 |
| Ref 257m3 | 3.89E-10 | 2.56E-10 | | 6.28E-08 |

The activity data reported relate to the working examples described in the present experimental section, with the drug/mAB ratios indicated. The values may possibly deviate for different drug/mAB ratios. The $IC_{50}$ values are means of several independent experiments or individual values. The action of the CD123 antibody drug conjugates was selective for the respective isotype comprising the respective linker and toxophore.

C-1b Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 µg/ml taxol (Sigma No. T7191-5 MG) for 5 min at RT in 15 mM PIPES, pH 6.8 (5 mM $MgCl_2$ and 10 mM DTT, Sigma). The freshly prepared mixture was aliquoted into a 384 MTP (Greiner bio-one REF 781096). The inhibitors to be examined at concentrations of $1.0 \times 10^{-6}$ M to $1.0 \times 10^{-13}$ M and ATP (final concentration 500 µM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The $IC_{50}$ values are means of two independent experiments. The 100% control was the sample which had not been treated with inhibitors.

Table 2 below lists the $IC_{50}$ values of representative working examples from the assay described and the corresponding cytotoxicity data (MTT assay).

TABLE 2

| Examples | KSP assay $IC_{50}$ [M] | NCI-H292 $IC_{50}$ [M] MTT assay |
|---|---|---|
| M20 | 1.50E-09 | 1.49E-07 |
| M21 | 2.31E-09 | |

The activity data reported relate to the working examples described in the present experimental section.

C-2a Internalisation Assay

Internalisation is a key process which enables specific and efficient provision of the cytotoxic payload in antigen-expressing cancer cells via antibody drug conjugates (ADC). This process is monitored via fluorescent labelling of specific CD123 antibodies and an isotype control antibody labelled with a pH-sensitive fluorophore. First, the fluorescent dye was conjugated to lysines of the antibody. Conjugation was carried out using a two-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537) to eliminate excess dye and to adjust the pH. The protein solution was concentrated using VIVASPIN 500 columns (Sartorius stedim biotec VS0131). The dye load of the antibody was determined by spectrophotometric analysis (NanoDrop) and subsequent calculation using the following equation D: $P = A_{dye\epsilon protein}: (A_{280} - 0.16 A_{dye})\epsilon_{dye}$. The dye load of the CD123 antibodies examined here and the isotype control were of a comparable order. In cell binding assays, it was confirmed that the conjugation did not lead to a change in the affinity of the antibodies. The antigen to be examined is expressed by haematopoietic suspension cells, and the internalisation of the labelled CD123 antibodies was therefore examined in an FACS-based internalisation assay. To this end, cell lines with different expression levels of the receptor were selected and tested. The cells ($5 \times 10^4$/well) were sown in a 96-MTP in a total volume of 100 µl (Greiner bio-one, CELLSTAR, 650 180, U-bottom). After addition of the anti-CD123 antibody to be examined in a final concentration of 10 µg/ml, the cell batches were incubated at 37° C. for different periods (1 h, 2 h, 6 h, in triplicate). The same treatment protocol was applied to the labelled isotype control (negative control). In parallel, identical test batches were processed at 4° C. (negative control). FACS analysis was then carried out using the Guava flow cytometer (Millipore). Kinetic evaluation was via measurement of the fluorescence intensity using the guavaSoft 2.6 software (Millipore). A target-mediated specific internalisation of the anti-CD123 antibodies was observed in various cancer cell lines (MOLM-13, THP-1, KG-1), whereas the isotype control and the 4° C. batches showed no internalisation.

C-2b Determination of the Co-Localisation of the Internalised CD123 Antibody in the Lysosome The toxic active compound of the antibody drug conjugates is released in the lysosome, owing to the linker selected. The transport of the antibody to this organelle is therefore crucial. By co-localisation of the antibody with marker proteins specific for the lysosome (e.g. surface protein or small GTPasen), it is possible to identify antibodies having a suitable profile. To this end, the CD123-positive cells ($5 \times 10^4$/well) in 100 µl of medium were initially sown into a 96-MTP (Greiner bio-one, CELLSTAR, 650 180, U-bottom). After addition of the CypHer5E-labelled anti-CD123 antibody (final concentration 20 µg/ml), the batches were incubated in duplicate at 37° C. for 6 h. In each case 30 min prior to the end of the incubation time, a lysosome-specific live dye was added to the samples. The lysomes were stained using the CytoPainter LysoGreen indicator reagent (final concentration 1:2000; abcam, ab176826). After incubation, 200 µl of ice-cold FACS buffer (DULBECCO'S PBS, Sigma-Aldrich, No. D8537+3% FBS heat inactivated FBS, Gibco, No. 10500-064) were pipetted into the batch and the cell suspension was centrifuged at 400×g and 4° C. for 5 min. The pellet was then resuspended in 300 µl ice-cold FACS buffer and centrifuged again (4 min, 400×g at 4° C.). After the centrifugation, the supernatant was discarded and the pellet was taken up in 30 µl of ice-cold FACS buffer. The samples prepared in this manner were immediately subjected to FACS/image analysis (FlowSight amnis, Millipore). Co-localisation was evaluated using the specific co-localisation software IDEAS Application v6.1. Table 3 summarizes the data from this assay for the anti-CD123 antibodies examined.

TABLE 3

| Examples | Co-localisation [%] |
| --- | --- |
| TPP-6013 | 43.5 |
| TPP-5969 | 26.0 |
| TPP-8987 | 28.0 |
| TPP-8988 | 41.0 |
| TPP-9476 | 29.0 |
| 7G3 | 10.0 |
| Isotype control | 0.2 |

Different antibodies showed an improved specific internalization potency and co-localization compared to the murine antibody.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropol mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as actively transported when the ratio of $P_{app}$ (B–A) to $P_{app}$ (A–B) (efflux ratio) was >2 or <0.5.

Of critical importance for toxophores which are released intracellularly is the permeability from B to A [$P_{app}$ (B–A)] and the ratio of $P_{app}$ (B–A) to $P_{app}$ (A–B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 4 below sets out permeability data for representative working examples from this assay:

TABLE 4

| Working Example | $P_{app}$ (B-A) [nm/s] | Efflux ratio |
| --- | --- | --- |
| M20 | 0.89 | 0.21 |
| M21 | 0.5 | 1.5 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., J. Clin. Invest. 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as P-gp substrate when the efflux ratio of $P_{app}$ (B–A) to $P_{app}$ (A–B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

C5a: Identification of the ADC Metabolites after Internalisation In Vitro

Description of the Method:

Internalisation studies with immunoconjugates are carried out to analyse metabolites formed intracellularly. To this end, human lung tumour cells NCI H292 ($3 \times 10^5$/well) are sown in 6-well plates and incubated overnight (37° C., 5%

$CO_2$). The cells are treated with 10 µg/ml (66 nM) of the ADC to be examined Internalisation was carried out at 37° C. and 5% $CO_2$. At various time points (0, 4, 24, 48, 72 h), cell samples are taken for further analysis. First, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2 \times 10^5$) is treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate is centrifuged (10 min, 4° C., 12000 g, Eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For work-up of 50 µl of culture supernatant/cell lysate, 150 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µs/1.

For calibration of the tumour samples, concentrations of 0.5-200 µg/l are added to the supernatant of untreated tumours. The detection limit is 4 µg/l. The linear range extends from 4 to 200 µg/l.

Quality controls for testing validity contain 5 and 50 µg/l.

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

Analysis for Quantification of any Metabolites Occurring

Measurement of the compounds in plasma and tumour is carried out after precipitation of the proteins with methanol or acetonitrile by high-pressure liquid chromatography (HPLC) coupled to a triple-quadrupole mass spectrometer (MS).

For work-up of 50 µl of plasma, 250 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

During the work-up of a tumour, the latter is treated with 3 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulphonyl fluoride (Sigma, St. Louis, Mo.) in a final concentration of 1 mM. The sample is homogenized twice for 20 minutes in a Tissuelyser II (Qiagen), at maximum stroke number. 50 µl of the homogenate are transferred into an autosampler vial and made up with 150 µl of methanol including ISTD. After 3 minutes of centrifugation at 16000 g, 10 µl of the supernatant are made up with 180 µl of a buffer suitable for the mobile phase and shaken again. The tumour sample is then ready for measuring.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µs/1.

For calibration of the tumour samples, concentrations of 0.5-200 µg/l are added to the supernatant of untreated tumours. The detection limit is 5 µg/l. The linear range extends from 5 to 200 µg/l.

Quality controls for testing validity contain 5 and 50 µg/l, in plasma additionally 500 µg/l.

Analysis for Quantification of the Antibodies Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG (H+L) antibody and horseradish peroxidase (HRP). After a further washing step, the HRP substrate was added to OPD and the colour development was monitored via absorption at 490 nm. Standard samples having a known IgG concentration were fitted using a 4-parameter equation. Within the lower (LLOQ) and upper (ULOQ) quantification limits, the unknown concentrations were determined by interpolation.

C-6 Efficacy Test In Vivo

The in vivo efficacy of the conjugates of this invention has been tested in tumor Xenograft models. The expert is familiar with methods in the prior art against which the effectiveness of the compounds of the invention can be tested (see for example WO 2005/081711; Polson et al, Cancer Res Mar. 15, 2009; 69 (6): 2358-64).

For example, rodents (e.g. mice) were implanted with a tumor cell line expressing the target molecule of the antibody. Then a conjugate of the invention, an isotype conjugate, a control antibody or isotonic saline (vehicle) were administered to the implanted animals. After an incubation period of several days, the tumor size was determined in conjugate treated animals vs. control groups (control conjugate and/or vehicle). The conjugate treated animals showed a reduced tumor size.

C-6a. Growth Inhibition of Experimental Tumors in Mice

Human tumor cells expressing the target antigen for the antibody-drug conjugate were inoculated subcutaneously into the flank of immunocompromised mice (e.g.: NMRI Nude- or SCID mice). 1-10 million cells were detached from cell culture, centrifuged and re-suspended with medium or medium/Matrigel. The cell suspension was injected subcutaneously into mice. Treatment (i.p. application at a volume of 5 mL/kg; Dosing schedule is shown in table x) started after establishment of the tumor, approximately at a tumor size of 40 $mm^2$ By default, 8 animals were used per treatment group. In addition to the groups that received the active substances, a group was treated with vehicle only. During the experiment, the tumor area was measured regularly with calipers in two dimensions (length/width). The tumor area was determined by length×width. The comparison of the mean tumor area of the treatment group with the control group was expressed as T/C area.

C-6b. Efficacy of Compounds According to the Invention in Human AML Xenograft Models Treatment with the anti CD123 antibody-drug conjugates resulted in a significant and long-lasting inhibition of tumor growth. Table 5 summarizes in vivo efficacy of representative working examples. Primary read out is the tumor growth inhibition in treatment vs. vehicle group as indicated by T/C values (determined from the last measured time point before the vehicle group reached a tumor size of >200 mm² and had to be sacrificed due to German animal protection law). As a second read out table 5 also indicates the time period until the treatment groups showed tumor regrowth and the study was terminated.

Exp 1 shows a strong efficacy and clear superiority of ref 257 ml vs 208 ml as measured by tumor growth inhibition in THP-1 AML Xenograft model (T/C 0.46 vs. 0.92)

The efficacy of ref 257 ml has also been evaluated in an additional AML Xenograft models. Exp. 2. confirmed superiority of ref 257 ml vs 208 ml based on tumor growth inhibition (T/C 0.25 vs 0.42) and also strongly reduced time until tumor regrowth in the MOLM 13 AML Xenograft model (34 days vs 24 days). The examples 1a, 1b, 1c show strong efficacy in two AML models (Exp. 3 and Exp. 4), All examples described show superiority versus ref 208 ml (e.g. 1a vs 208 ml-T/C 0.32 vs 0.42).

The corresponding isotype-ADC controls with the indicated schedule (Q7dx2) were comparable to vehicle controls.

Generation and Optimization of Humanized Anti-CD123 Antibodies

The antibodies described herein base on two murine antibody clones 7G3 and 12F1 described in literature (EP2426148; WO2013/173820). Shortly, the murine CDRs were grafted into human frameworks as described by O'Brien and Jones, (Chapter 40 Humanizing Antibodies by CDR Grafting, p579 Table 4) and also Hwang et al, (Methods 36 (2005) p 35-42). For the definition of the CDRs according to Kabat, see Andre C. R. Martin, "Protein sequence and structure analysis of antibody variable domains" in Antibody Engineering (Springer Lab Manuals), Eds.: Duebel, S. and Kontermann, R., Springer-Verlag, Heidelberg. After comparison of the murine frame sequences (without CDRs) with human germline sequences, a similar frequently occurring human frame sequence was selected. The sequences were named using the IMGT system (Lefranc, M. P., Giudicelli, V., Ginestoux, C., Jabado-Michaloud, J., Folch, G., Bellahcene, F., Wu, Y., Gemrot, E., Brochet, X., Lane, J., Regnier, L., Ehrenmann, F, Lefranc, G. and Duroux, P. IMGT®, the international ImMunoGeneTics information System®. Nucl. Acids Res, 37, D1006-D1012 (2009); doi: 10.1093/nar/gkn838).

The humanized variants were transiently expressed in HEK293 cells. Supernatants were tested in SPR and FACS for the binding to antigen and cells. To reduce immunogenicity and optimize binding properties, single or multiple mutations were introduced in CDRs and Frameworks. More than 100 variants were tested in order to generate and select the final lead candidates. The antibody variants described herein carry various point mutations differing from the human germline sequence which may influence their properties.

TABLE 5

| Exp. | Examples | Xenograft Model | Dosing | Treatment Schedule | T/C area | | Tumor Outgrowth of ADC vs. vehicle |
|---|---|---|---|---|---|---|---|
| Exp 1 | Ref 257m1 | THP-1 | 5 mg/kg | Q7dx2 | 0.46 | (Day21) | Vehicle Day 21 ADC Day ongoing |
|  | Ref 208m1 | THP-1 | 5 mg/kg | Q7dx2 | 0.92 | (Day21) | Vehicle Day 21 ADC Day 21 |
| Exp 2 | Ref 208m1 | MOLM-13 | 5mg/kg | Q7dx2 | 0.42 | (Day17) | Vehicle Day 17 ADC Day 24 |
|  | Ref 257m1 | MOLM-13 | 5mg/kg | Q7dx2 | 0.25 | (Day17) | Vehicle Day 17 ADC Day 31 |
| Exp 3 | 1a | MOLM13 | 5mg/kg | Q7dx2 | 0.32(day14) | | Vehicle Day 14 ADC Day 25 |
|  | 1b | MOLM13 | 5mg/kg | Q7dx2 | 0.37(day14) | | Vehicle Day 14 ADC Day 25 |
|  | 1c | M0LM13 | 5mg/kg | Q7dx2 | 0.33(day14) | | Vehicle Day 14 ADC Day 25 |
| Exp 4 | 1a | MV4-11 | 5mg/kg | Q7dx2 | 0.35(day21) | | Vehicle Day 21 ADC Day 32 |
|  | 1b | MV4-11 | 5mg/kg | Q7dx2 | 0.25 day21) | | Vehicle Day 21 ADC Day 35 |
|  | 1c | MV4-11 | 5mg/kg | Q7dx2 | 0.32(day21) | | Vehicle Day 21 ADC Day 35 |

Working Examples of Anti-CD123 Antibodies

All examples were carried out using standard methods known to the person skilled in the art, unless described here in detail. Routine methods of molecular biology of the examples that follow can be carried out as described in standard laboratory textbooks such as Sambrook et al., Molecular Cloning: a Laboratory Manual, 2. Edition; Cold Spring Harbor Laboratory Press, Cold Spring Harbor, N.Y., 1989.

The first campaign based on the murine antibody clone 12F1 (WO2013/173820). The grafting of the CDRs was not trivial and had to be tested on several human framework backbones in order succeed. The best grafted version was identified to be TPP-8988, in which the light chain CDRs were grafted into the human framework backbone IGKV3-20, the heavy chain CDRs were grafted into the human framework backbone IGHV3-66. In comparison, the grafting of the murine CDRs failed in other cases, e.g. for TPP-8613 which showed reduced FACS binding. In this variant, the light chain CDRs were grafted into the human framework backbone IGKV4-1, the heavy chain CDRs were grafted into the human framework backbone IGHV3-66. Another example that did not yield sufficient expression as a grafted version is TPP-8617, in which the light chain CDRs were grafted into the human framework backbone IGKV4-1, the heavy chain CDRs were grafted into the human framework backbone IGHV5-51.

To further de-immunize TPP-8988, single and recombined non-germline residues were exchanged to human germline and 66 variants were tested for expression and binding. The best recombination variant tested was TPP-9342. Other variants, as for example TPP-9075, TPP-9078, TPP-9104, TPP-9129 or TPP-9130 showed low expression and/or undesirable multiphasic behavior in the SPR measurements, although the share similar sequences with TPP-8988/TPP9342.

The second campaign based on the murine antibody clone 7G3 (EP2426148). The humanized version TPP-5969 was generated as described above, based on human germlines IGKV4-1 and IGHV1-69. It can serve as an alternative to CSL-362 (TPP-5709), a humanized version generated by CSL (EP2606069). Unfortunately, TPP-5969 showed an undesirable multiphasic binding behaviour in the SPR analysis. To abolish this multiphasic binding and to de-immunize TPP-5969 and, single and recombined non-germline residues were exchanged to human germline and 53 variants were tested for expression and binding. Most variants, as for example TPP-8465, TPP-8467, TPP-8468, or TPP-9479 showed low expression and multiphasic behavior in the SPR measurements as well diminished FACS binding, although the share similar sequences with humanized version TPP-5969 and/or the final candidates TPP-8987 or TPP-9476.

Only variants, such as e.g. TPP-8695, containing three mutations in the heavy chain (N61A, K65Q and Q67R) compared to TPP-5969 showed single digit nanomolar EC50 values in FACS binding while still binding in a multiphasic fashion in SPR at low expression. Unexpectedly, the introduction of a single point mutation in the light chain CDR2 (V29L) in TPP8987 abolished the undesirable multiphasic binding properties. Since the expression rates of TPP-8987 were rather low, different heavy chain variants were generated in order to find a recombination of mutations that allows reasonable expression together with non-multiphasic SPR binding properties and positive FACS results. Those assets are represented by TPP-9476 which only differs from TPP-8987 in the R67Q back mutation but expresses 10-fold higher while retaining its favorable binding features.

Determination of the Binding Affinity of the Antibodies by Surface Plasmon Resonance:

Surface plasmon resonance experiments for quantitative binding analysis were carried out using a Biacore T200 instrument (GE Healthcare Biacore, Inc.). Here the antibodies to be examined were fixed with the aid of an anti-human Fc antibody ("Human Antibody Capture Kit", BR-1008-39, GE Healthcare Biacore, Inc.) amine-coupled to the sensor chip surface Amine coupling was performed according to the manufacturer's instructions using 1-ethyl-3-(3-dimethylaminopropyl)carbodiimide hydrochloride (EDC), N-hydroxysuccinimide (NHS) and ethanolamine HCl pH 8.5 ("Amine Coupling Kit" BR-1000-50, GE Healthcare Biacore, Inc.). For the analyses, Series S sensor chips CM5 (GE Healthcare Biacore, Inc.) were used with the mobile buffer HBS-EP+ (10 mM HEPES pH 7.4, 150 mM NaCl, 3 mM EDTA, 0.05% Surfactant P20). All experimental steps were carried out at 25° C. After fixation of the anti-CD123 antibodies to be examined, injections of the extracellular domain of IL3Ra (analyte, R&D Systems) at concentrations of 100 nM were carried out, and after each antigen injection the sensor surface was regenerated with glycine HCl pH 2.0. Prior to another analyte injection, antibodies were in each case fixed as above, under identical conditions. For all measurements, an upstream flow cell only containing immobilized amine-coupled anti-human Fc antibody was used as reference cell. Evaluation of the sensorgrams obtained was, after double referencing (subtraction of the reference flow cell signal and a buffer injection), carried out by a global fit based on a 1:1 Langmuir binding model with the aid of the Biacore T200 evaluation software (GE Healthcare Biacore, Inc.).

TABLE 6a

Recombinant antigen (IL3R3alpha/CD123) used for affinity determination

| Nomenclature | Description | Origin | Cat. No. (R&D) |
|---|---|---|---|
| TPP-5521 | IL3Ra aa20-305 | murine | 203-IL |

TABLE 6b

Monovalent $K_D$ values of the anti-CD123 antibodies determined with Biacore using IL3Ra protein (TPP-5521 as analyte)

| TPP | $K_D$ [nM] | Chi2 % of Rmax | Multiphasic behaviour |
|---|---|---|---|
| TPP-5969 | Kinetic evaluation not applicable | — | Yes |
| TPP-8987 | 1.24 | | No |
| TPP-9476 | 7.2 | | No |
| TPP-6013 | 0.8 | 1 | No |
| TPP-8988 | 0.23 | | No |
| TPP-9342 | | | |

Binding of Anti-CD123 Antibodies to Various Antigen-Expressing Cancer Cell Lines Binding of the anti-CD123 antibodies was examined by flow cytometry using human haematological cell line MOLM-13. To this end, the cells ($5×10^5$ cells/well) were incubated in FACS buffer (PBS without Ca/Mg, 3% FCS, Biochrom) with 10 µg/ml primary antibody solution (start concentration) on ice for 30-45 min protected from light. A dose activity curve (1:5 dilution) was plotted. After the incubation, 200 µl of ice-cold FACS buffer were added using a pipette, and the cell suspension was centrifuged at 4° C. 400 g for 4 min. The cell pellet was washed with 300 µl of ice-cold FACS buffer and the pellet obtained was then resuspended in 100 µl FACS buffer and incubated again with secondary antibody (monoclonal anti-kappa light chains-FITC antibody, Sigma, No. SAB4700605) in a 1:10 dilution on ice for 30 min. The cells were then washed with ice-cold FACS buffer and adjusted to a cell concentration of $0.5×10^6$ cell/ml prior to flow cytometry using a Guava flow cytometer (Millipore). Propidium iodide (final concentration 1 µg/ml) was used for live staining. The results were shown as EC50 values determined based on the dose response curve and efficacy compared to maximal binding. Surprisingly a significant improved binding behaviour could be detected with TPP-8988 compared to TPP-5969 and TPP-8988 compared to TPP-6013 (Table 7A) Most humanized variants of TPP-5969 showed no or insufficient binding to the target (7B) as well as the humanized variants of TPP-6013 (7C; see generation and optimization).

TABLE 7

FACS analysis: Binding of the anti-CD123 antibodies to MOLM-13 cancer cell line. A improved humanized anti-CD123 antibodies; B TPP-5963 variants; C TPP-6013 variants

| TPP | MOLM-13 EC50 [nM] | Efficacy [%] |
|---|---|---|
| A | | |
| TPP-5969 | 5.3 | 34 |
| TPP-8987 | 3.2 | 100 |
| TPP-9476 | 2.8 | 100 |
| TPP-6013 | 2.0 | 100 |
| TPP-8988 | 1.9 | 100 |
| TPP-9342 | | |
| B | | |
| TPP-8465 | No binding | |
| TPP-8467 | No binding | |
| TPP-8468 | No binding | |
| TPP-8476 | No binding | |
| TPP-8695 | 1.12 | 36 |
| C | | |
| TPP-8613 | 3.0 | 100 |
| TPP-8617 | 1.4 | 100 |
| TPP-9075 | 5.37 | 100 |
| TPP-9078 | No binding | — |
| TPP-9104 | 25.3 | 83 |
| TPP-9129 | No binding | — |
| TPP-9130 | 3.01 | 100 |

TABLE

List of Sequenzes

| TPP ID | Sequence Name | Sequence Region | Sequence Type | SEQ ID |
|---|---|---|---|---|
| TPP-5709 | CSL362-hIgG1Kappa | VH | PRT | SEQ ID NO: 1 |
| TPP-5709 | CSL362-hIgG1Kappa | HCDR1 | PRT | SEQ ID NO: 2 |
| TPP-5709 | CSL362-hIgG1Kappa | HCDR2 | PRT | SEQ ID NO: 3 |
| TPP-5709 | CSL362-hIgG1Kappa | HCDR3 | PRT | SEQ ID NO: 4 |
| TPP-5709 | CSL362-hIgG1Kappa | VL | PRT | SEQ ID NO: 5 |
| TPP-5709 | CSL362-hIgG1Kappa | LCDR1 | PRT | SEQ ID NO: 6 |
| TPP-5709 | CSL362-hIgG1Kappa | LCDR2 | PRT | SEQ ID NO: 7 |
| TPP-5709 | CSL362-hIgG1Kappa | LCDR3 | PRT | SEQ ID NO: 8 |
| TPP-5709 | CSL362-hIgG1Kappa | Heavy Chain | PRT | SEQ ID NO: 9 |
| TPP-5709 | CSL362-hIgG1Kappa | Light Chain | PRT | SEQ ID NO: 10 |
| TPP-5968 | HU7G3-1-hIgG1Kappa | VH | PRT | SEQ ID NO: 11 |
| TPP-5968 | HU7G3-1-hIgG1Kappa | HCDR1 | PRT | SEQ ID NO: 12 |
| TPP-5968 | HU7G3-1-hIgG1Kappa | HCDR2 | PRT | SEQ ID NO: 13 |
| TPP-5968 | HU7G3-1-hIgG1Kappa | HCDR3 | PRT | SEQ ID NO: 14 |
| TPP-5968 | HU7G3-1-hIgG1Kappa | VL | PRT | SEQ ID NO: 15 |
| TPP-5968 | HU7G3-1-hIgG1Kappa | LCDR1 | PRT | SEQ ID NO: 16 |
| TPP-5968 | HU7G3-1-hIgG1Kappa | LCDR2 | PRT | SEQ ID NO: 17 |
| TPP-5968 | HU7G3-1-hIgG1Kappa | LCDR3 | PRT | SEQ ID NO: 18 |
| TPP-5968 | HU7G3-1-hIgG1Kappa | Heavy Chain | PRT | SEQ ID NO: 19 |
| TPP-5968 | HU7G3-1-hIgG1Kappa | Light Chain | PRT | SEQ ID NO: 20 |
| TPP-5969 | HU7G3-4-hIgG1Kappa | VH | PRT | SEQ ID NO: 21 |
| TPP-5969 | HU7G3-4-hIgG1Kappa | HCDR1 | PRT | SEQ ID NO: 22 |
| TPP-5969 | HU7G3-4-hIgG1Kappa | HCDR2 | PRT | SEQ ID NO: 23 |
| TPP-5969 | HU7G3-4-hIgG1Kappa | HCDR3 | PRT | SEQ ID NO: 24 |
| TPP-5969 | HU7G3-4-hIgG1Kappa | VL | PRT | SEQ ID NO: 25 |
| TPP-5969 | HU7G3-4-hIgG1Kappa | LCDR1 | PRT | SEQ ID NO: 26 |
| TPP-5969 | HU7G3-4-hIgG1Kappa | LCDR2 | PRT | SEQ ID NO: 27 |
| TPP-5969 | HU7G3-4-hIgG1Kappa | LCDR3 | PRT | SEQ ID NO: 28 |
| TPP-5969 | HU7G3-4-hIgG1Kappa | Heavy Chain | PRT | SEQ ID NO: 29 |
| TPP-5969 | HU7G3-4-hIgG1Kappa | Light Chain | PRT | SEQ ID NO: 30 |
| TPP-5971 | HU7G3-3-hIgG1Kappa | VH | PRT | SEQ ID NO: 31 |
| TPP-5971 | HU7G3-3-hIgG1Kappa | HCDR1 | PRT | SEQ ID NO: 32 |
| TPP-5971 | HU7G3-3-hIgG1Kappa | HCDR2 | PRT | SEQ ID NO: 33 |
| TPP-5971 | HU7G3-3-hIgG1Kappa | HCDR3 | PRT | SEQ ID NO: 34 |
| TPP-5971 | HU7G3-3-hIgG1Kappa | VL | PRT | SEQ ID NO: 35 |
| TPP-5971 | HU7G3-3-hIgG1Kappa | LCDR1 | PRT | SEQ ID NO: 36 |
| TPP-5971 | HU7G3-3-hIgG1Kappa | LCDR2 | PRT | SEQ ID NO: 37 |
| TPP-5971 | HU7G3-3-hIgG1Kappa | LCDR3 | PRT | SEQ ID NO: 38 |
| TPP-5971 | HU7G3-3-hIgG1Kappa | Heavy Chain | PRT | SEQ ID NO: 39 |
| TPP-5971 | HU7G3-3-hIgG1Kappa | Light Chain | PRT | SEQ ID NO: 40 |
| TPP-6013 | antiCD123-12F1-hIg1Kappa | VH | PRT | SEQ ID NO: 41 |
| TPP-6013 | antiCD123-12F1-hIgG1Kappa | HCDR1 | PRT | SEQ ID NO: 42 |
| TPP-6013 | antiCD123-12F1-hIgG1Kappa | HCDR2 | PRT | SEQ ID NO: 43 |
| TPP-6013 | antiCD123-12F1-hIgG1Kappa | HCDR3 | PRT | SEQ ID NO: 44 |

TABLE-continued

List of Sequenzes

| TPP ID | Sequence Name | Sequence Region | Sequence Type | SEQ ID |
|---|---|---|---|---|
| TPP-6013 | antiCD123-12F1-hIgG1Kappa | VL | PRT | SEQ ID NO: 45 |
| TPP-6013 | antiCD123-12F1-hIgG1Kappa | LCDR1 | PRT | SEQ ID NO: 46 |
| TPP-6013 | antiCD123-12F1-hIgG1Kappa | LCDR2 | PRT | SEQ ID NO: 47 |
| TPP-6013 | antiCD123-12F1-hIgG1Kappa | LCDR3 | PRT | SEQ ID NO: 48 |
| TPP-6013 | antiCD123-12F1-hIgG1Kappa | Heavy Chain | PRT | SEQ ID NO: 49 |
| TPP-6013 | antiCD123-12F1-hIgG1Kappa | Light Chain | PRT | SEQ ID NO: 50 |
| TPP-8465 | GL-TPP5969-hIgG1kappa-g105 | VH | PRT | SEQ ID NO: 51 |
| TPP-8465 | GL-TPP5969-hIgG1kappa-g105 | HCDR1 | PRT | SEQ ID NO: 52 |
| TPP-8465 | GL-TPP5969-hIgG1kappa-g105 | HCDR2 | PRT | SEQ ID NO: 53 |
| TPP-8465 | GL-TPP5969-hIgG1kappa-g105 | HCDR3 | PRT | SEQ ID NO: 54 |
| TPP-8465 | GL-TPP5969-hIgG1kappa-g105 | VL | PRT | SEQ ID NO: 55 |
| TPP-8465 | GL-TPP5969-hIgG1kappa-g105 | LCDR1 | PRT | SEQ ID NO: 56 |
| TPP-8465 | GL-TPP5969-hIgG1kappa-g105 | LCDR2 | PRT | SEQ ID NO: 57 |
| TPP-8465 | GL-TPP5969-hIgG1kappa-g105 | LCDR3 | PRT | SEQ ID NO: 58 |
| TPP-8465 | GL-TPP5969-hIgG1kappa-g105 | Heavy Chain | PRT | SEQ ID NO: 59 |
| TPP-8465 | GL-TPP5969-hIgG1kappa-g105 | Light Chain | PRT | SEQ ID NO: 60 |
| TPP-8467 | GL-TPP5969-hIgG1kappa-g107 | VH | PRT | SEQ ID NO: 61 |
| TPP-8467 | GL-TPP5969-hIgG1kappa-g107 | HCDR1 | PRT | SEQ ID NO: 62 |
| TPP-8467 | GL-TPP5969-hIgG1kappa-g107 | HCDR2 | PRT | SEQ ID NO: 63 |
| TPP-8467 | GL-TPP5969-hIgG1kappa-g107 | HCDR3 | PRT | SEQ ID NO: 64 |
| TPP-8467 | GL-TPP5969-hIgG1kappa-g107 | VL | PRT | SEQ ID NO: 65 |
| TPP-8467 | GL-TPP5969-hIgG1kappa-g107 | LCDR1 | PRT | SEQ ID NO: 66 |
| TPP-8467 | GL-TPP5969-hIgG1kappa-g107 | LCDR2 | PRT | SEQ ID NO: 67 |
| TPP-8467 | GL-TPP5969-hIgG1kappa-g107 | LCDR3 | PRT | SEQ ID NO: 68 |
| TPP-8467 | GL-TPP5969-hIgG1kappa-g107 | Heavy Chain | PRT | SEQ ID NO: 69 |
| TPP-8467 | GL-TPP5969-hIgG1kappa-g107 | Light Chain | PRT | SEQ ID NO: 70 |
| TPP-8468 | GL-TPP5969-hIgG1kappa-g108 | VH | PRT | SEQ ID NO: 71 |
| TPP-8468 | GL-TPP5969-hIgG1kappa-g108 | HCDR1 | PRT | SEQ ID NO: 72 |
| TPP-8468 | GL-TPP5969-hIgG1kappa-g108 | HCDR2 | PRT | SEQ ID NO: 73 |
| TPP-8468 | GL-TPP5969-hIgG1kappa-g108 | HCDR3 | PRT | SEQ ID NO: 74 |
| TPP-8468 | GL-TPP5969-hIgG1kappa-g108 | VL | PRT | SEQ ID NO: 75 |
| TPP-8468 | GL-TPP5969-hIgG1kappa-g108 | LCDR1 | PRT | SEQ ID NO: 76 |
| TPP-8468 | GL-TPP5969-hIgG1kappa-g108 | LCDR2 | PRT | SEQ ID NO: 77 |
| TPP-8468 | GL-TPP5969-hIgG1kappa-g108 | LCDR3 | PRT | SEQ ID NO: 78 |
| TPP-8468 | GL-TPP5969-hIgG1kappa-g108 | Heavy Chain | PRT | SEQ ID NO: 79 |
| TPP-8468 | GL-TPP5969-hIgG1kappa-g108 | Light Chain | PRT | SEQ ID NO: 80 |
| TPP-8476 | GL-TPP5969-hIgG1kappa-g116 | VH | PRT | SEQ ID NO: 81 |

TABLE-continued

List of Sequenzes

| TPP ID | Sequence Name | Sequence Region | Sequence Type | SEQ ID |
|---|---|---|---|---|
| TPP-8476 | GL-TPP5969-hIgG1kappa-g116 | HCDR1 | PRT | SEQ ID NO: 82 |
| TPP-8476 | GL-TPP5969-hIgG1kappa-g116 | HCDR2 | PRT | SEQ ID NO: 83 |
| TPP-8476 | GL-TPP5969-hIgG1kappa-g116 | HCDR3 | PRT | SEQ ID NO: 84 |
| TPP-8476 | GL-TPP5969-hIgG1kappa-g116 | VL | PRT | SEQ ID NO: 85 |
| TPP-8476 | GL-TPP5969-hIgG1kappa-g116 | LCDR1 | PRT | SEQ ID NO: 86 |
| TPP-8476 | GL-TPP5969-hIgG1kappa-g116 | LCDR2 | PRT | SEQ ID NO: 87 |
| TPP-8476 | GL-TPP5969-hIgG1kappa-g116 | LCDR3 | PRT | SEQ ID NO: 88 |
| TPP-8476 | GL-TPP5969-hIgG1kappa-g116 | Heavy Chain | PRT | SEQ ID NO: 89 |
| TPP-8476 | GL-TPP5969-hIgG1kappa-g116 | Light Chain | PRT | SEQ ID NO: 90 |
| TPP-8613 | Hum-TPP6013-13 | VH | PRT | SEQ ID NO: 91 |
| TPP-8613 | Hum-TPP6013-13 | HCDR1 | PRT | SEQ ID NO: 92 |
| TPP-8613 | Hum-TPP6013-13 | HCDR2 | PRT | SEQ ID NO: 93 |
| TPP-8613 | Hum-TPP6013-13 | HCDR3 | PRT | SEQ ID NO: 94 |
| TPP-8613 | Hum-TPP6013-13 | VL | PRT | SEQ ID NO: 95 |
| TPP-8613 | Hum-TPP6013-13 | LCDR1 | PRT | SEQ ID NO: 96 |
| TPP-8613 | Hum-TPP6013-13 | LCDR2 | PRT | SEQ ID NO: 97 |
| TPP-8613 | Hum-TPP6013-13 | LCDR3 | PRT | SEQ ID NO: 98 |
| TPP-8613 | Hum-TPP6013-13 | Heavy Chain | PRT | SEQ ID NO: 99 |
| TPP-8613 | Hum-TPP6013-13 | Light Chain | PRT | SEQ ID NO: 100 |
| TPP-8617 | Hum-TPP6013-17 | VH | PRT | SEQ ID NO: 101 |
| TPP-8617 | Hum-TPP6013-17 | HCDR1 | PRT | SEQ ID NO: 102 |
| TPP-8617 | Hum-TPP6013-17 | HCDR2 | PRT | SEQ ID NO: 103 |
| TPP-8617 | Hum-TPP6013-17 | HCDR3 | PRT | SEQ ID NO: 104 |
| TPP-8617 | Hum-TPP6013-17 | VL | PRT | SEQ ID NO: 105 |
| TPP-8617 | Hum-TPP6013-17 | LCDR1 | PRT | SEQ ID NO: 106 |
| TPP-8617 | Hum-TPP6013-17 | LCDR2 | PRT | SEQ ID NO: 107 |
| TPP-8617 | Hum-TPP6013-17 | LCDR3 | PRT | SEQ ID NO: 108 |
| TPP-8617 | Hum-TPP6013-17 | Heavy Chain | PRT | SEQ ID NO: 109 |
| TPP-8617 | Hum-TPP6013-17 | Light Chain | PRT | SEQ ID NO: 110 |
| TPP-8695 | Variant4-hIgG1kappa | VH | PRT | SEQ ID NO: 111 |
| TPP-8695 | Variant4-hIgG1kappa | HCDR1 | PRT | SEQ ID NO: 112 |
| TPP-8695 | Variant4-hIgG1kappa | HCDR2 | PRT | SEQ ID NO: 113 |
| TPP-8695 | Variant4-hIgG1kappa | HCDR3 | PRT | SEQ ID NO: 114 |
| TPP-8695 | Variant4-hIgG1kappa | VL | PRT | SEQ ID NO: 115 |
| TPP-8695 | Variant4-hIgG1kappa | LCDR1 | PRT | SEQ ID NO: 116 |
| TPP-8695 | Variant4-hIgG1kappa | LCDR2 | PRT | SEQ ID NO: 117 |
| TPP-8695 | Variant4-hIgG1kappa | LCDR3 | PRT | SEQ ID NO: 118 |
| TPP-8695 | Variant4-hIgG1kappa | Heavy Chain | PRT | SEQ ID NO: 119 |
| TPP-8695 | Variant4-hIgG1kappa | Light Chain | PRT | SEQ ID NO: 120 |
| TPP-8987 | Hum 5969 B10-hIgG1Kappa | VH | PRT | SEQ ID NO: 121 |
| TPP-8987 | Hum 5969 B10-hIgG1Kappa | HCDR1 | PRT | SEQ ID NO: 122 |
| TPP-8987 | Hum 5969 B10-hIgG1Kappa | HCDR2 | PRT | SEQ ID NO: 123 |
| TPP-8987 | Hum 5969 B10-hIgG1Kappa | HCDR3 | PRT | SEQ ID NO: 124 |
| TPP-8987 | Hum 5969 B10-hIgG1Kappa | VL | PRT | SEQ ID NO: 125 |
| TPP-8987 | Hum 5969 B10-hIgG1Kappa | LCDR1 | PRT | SEQ ID NO: 126 |
| TPP-8987 | Hum 5969 B10-hIgG1Kappa | LCDR2 | PRT | SEQ ID NO: 127 |
| TPP-8987 | Hum 5969 B10-hIgG1Kappa | LCDR3 | PRT | SEQ ID NO: 128 |
| TPP-8987 | Hum 5969 B10-hIgG1Kappa | Heavy Chain | PRT | SEQ ID NO: 129 |
| TPP-8987 | Hum 5969 B10-hIgG1Kappa | Light Chain | PRT | SEQ ID NO: 130 |
| TPP-8988 | Hum 6013 B2-hIgG1Kappa | VH | PRT | SEQ ID NO: 131 |
| TPP-8988 | Hum 6013 B2-hIgG1Kappa | HCDR1 | PRT | SEQ ID NO: 132 |
| TPP-8988 | Hum 6013 B2-hIgG1Kappa | HCDR2 | PRT | SEQ ID NO: 133 |

TABLE-continued

List of Sequenzes

| TPP ID | Sequence Name | Sequence Region | Sequence Type | SEQ ID |
|---|---|---|---|---|
| TPP-8988 | Hum 6013 B2-hIgG1Kappa | HCDR3 | PRT | SEQ ID NO: 134 |
| TPP-8988 | Hum 6013 B2-hIgG1Kappa | VL | PRT | SEQ ID NO: 135 |
| TPP-8988 | Hum 6013 B2-hIgG1Kappa | LCDR1 | PRT | SEQ ID NO: 136 |
| TPP-8988 | Hum 6013 B2-hIgG1Kappa | LCDR2 | PRT | SEQ ID NO: 137 |
| TPP-8988 | Hum 6013 B2-hIgG1Kappa | LCDR3 | PRT | SEQ ID NO: 138 |
| TPP-8988 | Hum 6013 B2-hIgG1Kappa | Heavy Chain | PRT | SEQ ID NO: 139 |
| TPP-8988 | Hum 6013 B2-hIgG1Kappa | Light Chain | PRT | SEQ ID NO: 140 |
| TPP-9075 | GL-8988-hIgGkappa-g11 | VH | PRT | SEQ ID NO: 141 |
| TPP-9075 | GL-8988-hIgGkappa-g11 | HCDR1 | PRT | SEQ ID NO: 142 |
| TPP-9075 | GL-8988-hIgGkappa-g11 | HCDR2 | PRT | SEQ ID NO: 143 |
| TPP-9075 | GL-8988-hIgGkappa-g11 | HCDR3 | PRT | SEQ ID NO: 144 |
| TPP-9075 | GL-8988-hIgGkappa-g11 | VL | PRT | SEQ ID NO: 145 |
| TPP-9075 | GL-8988-hIgGkappa-g11 | LCDR1 | PRT | SEQ ID NO: 146 |
| TPP-9075 | GL-8988-hIgGkappa-g11 | LCDR2 | PRT | SEQ ID NO: 147 |
| TPP-9075 | GL-8988-hIgGkappa-g11 | LCDR3 | PRT | SEQ ID NO: 148 |
| TPP-9075 | GL-8988-hIgGkappa-g11 | Heavy Chain | PRT | SEQ ID NO: 149 |
| TPP-9075 | GL-8988-hIgGkappa-g11 | Light Chain | PRT | SEQ ID NO: 150 |
| TPP-9078 | GL-8988-hIgGkappa-g14 | VH | PRT | SEQ ID NO: 151 |
| TPP-9078 | GL-8988-hIgGkappa-g14 | HCDR1 | PRT | SEQ ID NO: 152 |
| TPP-9078 | GL-8988-hIgGkappa-g14 | HCDR2 | PRT | SEQ ID NO: 153 |
| TPP-9078 | GL-8988-hIgGkappa-g14 | HCDR3 | PRT | SEQ ID NO: 154 |
| TPP-9078 | GL-8988-hIgGkappa-g14 | VL | PRT | SEQ ID NO: 155 |
| TPP-9078 | GL-8988-hIgGkappa-g14 | LCDR1 | PRT | SEQ ID NO: 156 |
| TPP-9078 | GL-8988-hIgGkappa-g14 | LCDR2 | PRT | SEQ ID NO: 157 |
| TPP-9078 | GL-8988-hIgGkappa-g14 | LCDR3 | PRT | SEQ ID NO: 158 |
| TPP-9078 | GL-8988-hIgGkappa-g14 | Heavy Chain | PRT | SEQ ID NO: 159 |
| TPP-9078 | GL-8988-hIgGkappa-g14 | Light Chain | PRT | SEQ ID NO: 160 |
| TPP-9104 | GL-8988-hIgGkappa-g156 | VH | PRT | SEQ ID NO: 161 |
| TPP-9104 | GL-8988-hIgGkappa-g156 | HCDR1 | PRT | SEQ ID NO: 162 |
| TPP-9104 | GL-8988-hIgGkappa-g156 | HCDR2 | PRT | SEQ ID NO: 163 |
| TPP-9104 | GL-8988-hIgGkappa-g156 | HCDR3 | PRT | SEQ ID NO: 164 |
| TPP-9104 | GL-8988-hIgGkappa-g156 | VL | PRT | SEQ ID NO: 165 |
| TPP-9104 | GL-8988-hIgGkappa-g156 | LCDR1 | PRT | SEQ ID NO: 166 |
| TPP-9104 | GL-8988-hIgGkappa-g156 | LCDR2 | PRT | SEQ ID NO: 167 |
| TPP-9104 | GL-8988-hIgGkappa-g156 | LCDR3 | PRT | SEQ ID NO: 168 |
| TPP-9104 | GL-8988-hIgGkappa-g156 | Heavy Chain | PRT | SEQ ID NO: 169 |
| TPP-9104 | GL-8988-hIgGkappa-g156 | Light Chain | PRT | SEQ ID NO: 170 |
| TPP-9129 | GL-8988-hIgGkappa-g146 | VH | PRT | SEQ ID NO: 171 |
| TPP-9129 | GL-8988-hIgGkappa-g146 | HCDR1 | PRT | SEQ ID NO: 172 |
| TPP-9129 | GL-8988-hIgGkappa-g146 | HCDR2 | PRT | SEQ ID NO: 173 |
| TPP-9129 | GL-8988-hIgGkappa-g146 | HCDR3 | PRT | SEQ ID NO: 174 |
| TPP-9129 | GL-8988-hIgGkappa-g146 | VL | PRT | SEQ ID NO: 175 |
| TPP-9129 | GL-8988-hIgGkappa-g146 | LCDR1 | PRT | SEQ ID NO: 176 |
| TPP-9129 | GL-8988-hIgGkappa-g146 | LCDR2 | PRT | SEQ ID NO: 177 |
| TPP-9129 | GL-8988-hIgGkappa-g146 | LCDR3 | PRT | SEQ ID NO: 178 |
| TPP-9129 | GL-8988-hIgGkappa-g146 | Heavy Chain | PRT | SEQ ID NO: 179 |
| TPP-9129 | GL-8988-hIgGkappa-g146 | Light Chain | PRT | SEQ ID NO: 180 |
| TPP-9130 | GL-8988-hIgGkappa-g147 | VH | PRT | SEQ ID NO: 181 |
| TPP-9130 | GL-8988-hIgGkappa-g147 | HCDR1 | PRT | SEQ ID NO: 182 |
| TPP-9130 | GL-8988-hIgGkappa-g147 | HCDR2 | PRT | SEQ ID NO: 183 |
| TPP-9130 | GL-8988-hIgGkappa-g147 | HCDR3 | PRT | SEQ ID NO: 184 |
| TPP-9130 | GL-8988-hIgGkappa-g147 | VL | PRT | SEQ ID NO: 185 |
| TPP-9130 | GL-8988-hIgGkappa-g147 | LCDR1 | PRT | SEQ ID NO: 186 |
| TPP-9130 | GL-8988-hIgGkappa-g147 | LCDR2 | PRT | SEQ ID NO: 187 |
| TPP-9130 | GL-8988-hIgGkappa-g147 | LCDR3 | PRT | SEQ ID NO: 188 |
| TPP-9130 | GL-8988-hIgGkappa-g147 | Heavy Chain | PRT | SEQ ID NO: 189 |
| TPP-9130 | GL-8988-hIgGkappa-g147 | Light Chain | PRT | SEQ ID NO: 190 |
| TPP-9342 | 8988-g158-hIgG1kappa | VH | PRT | SEQ ID NO: 191 |
| TPP-9342 | 8988-g158-hIgG1kappa | HCDR1 | PRT | SEQ ID NO: 192 |
| TPP-9342 | 8988-g158-hIgG1kappa | HCDR2 | PRT | SEQ ID NO: 193 |
| TPP-9342 | 8988-g158-hIgG1kappa | HCDR3 | PRT | SEQ ID NO: 194 |
| TPP-9342 | 8988-g158-hIgG1kappa | VL | PRT | SEQ ID NO: 195 |
| TPP-9342 | 8988-g158-hIgG1kappa | LCDR1 | PRT | SEQ ID NO: 196 |
| TPP-9342 | 8988-g158-hIgG1kappa | LCDR2 | PRT | SEQ ID NO: 197 |
| TPP-9342 | 8988-g158-hIgG1kappa | LCDR3 | PRT | SEQ ID NO: 198 |
| TPP-9342 | 8988-g158-hIgG1kappa | Heavy Chain | PRT | SEQ ID NO: 199 |
| TPP-9342 | 8988-g158-hIgG1kappa | Light Chain | PRT | SEQ ID NO: 200 |
| TPP-9476 | 5969-g144-hIgG1kappa | VH | PRT | SEQ ID NO: 201 |

TABLE-continued

List of Sequenzes

| TPP ID | Sequence Name | Sequence Region | Sequence Type | SEQ ID |
|---|---|---|---|---|
| TPP-9476 | 5969-g144-hIgG1kappa | HCDR1 | PRT | SEQ ID NO: 202 |
| TPP-9476 | 5969-g144-hIgG1kappa | HCDR2 | PRT | SEQ ID NO: 203 |
| TPP-9476 | 5969-g144-hIgG1kappa | HCDR3 | PRT | SEQ ID NO: 204 |
| TPP-9476 | 5969-g144-hIgG1kappa | VL | PRT | SEQ ID NO: 205 |
| TPP-9476 | 5969-g144-hIgG1kappa | LCDR1 | PRT | SEQ ID NO: 206 |
| TPP-9476 | 5969-g144-hIgG1kappa | LCDR2 | PRT | SEQ ID NO: 207 |
| TPP-9476 | 5969-g144-hIgG1kappa | LCDR3 | PRT | SEQ ID NO: 208 |
| TPP-9476 | 5969-g144-hIgG1kappa | Heavy Chain | PRT | SEQ ID NO: 209 |
| TPP-9476 | 5969-g144-hIgG1kappa | Light Chain | PRT | SEQ ID NO: 210 |
| TPP-9479 | 5969-g147-hIgG1kappa | VH | PRT | SEQ ID NO: 211 |
| TPP-9479 | 5969-g147-hIgG1kappa | HCDR1 | PRT | SEQ ID NO: 212 |
| TPP-9479 | 5969-g147-hIgG1kappa | HCDR2 | PRT | SEQ ID NO: 213 |
| TPP-9479 | 5969-g147-hIgG1kappa | HCDR3 | PRT | SEQ ID NO: 214 |
| TPP-9479 | 5969-g147-hIgG1kappa | VL | PRT | SEQ ID NO: 215 |
| TPP-9479 | 5969-g147-hIgG1kappa | LCDR1 | PRT | SEQ ID NO: 216 |
| TPP-9479 | 5969-g147-hIgG1kappa | LCDR2 | PRT | SEQ ID NO: 217 |
| TPP-9479 | 5969-g147-hIgG1kappa | LCDR3 | PRT | SEQ ID NO: 218 |
| TPP-9479 | 5969-g147-hIgG1kappa | Heavy Chain | PRT | SEQ ID NO: 219 |
| TPP-9479 | 5969-g147-hIgG1kappa | Light Chain | PRT | SEQ ID NO: 220 |

What is claimed is:

1. An antibody or antigen-binding antibody fragment that binds to CD123, comprising a variable heavy chain comprising the variable CDR1 sequence of the heavy chain, as shown in SEQ ID NO: 202, the variable CDR2 sequence of the heavy chain, as shown in SEQ ID NO: 203, and the variable CDR3 sequence of the heavy chain, as shown in SEQ ID NO: 204; and a variable light chain comprising the variable CDR1 sequence of the light chain, as shown in SEQ ID NO: 206, the variable CDR2 sequence of the light chain, as shown in SEQ ID NO: 207, and the variable CDR3 sequence of the light chain, as shown in SEQ ID NO: 208.

2. The antibody or antigen-binding antibody fragment of claim 1, wherein the variable heavy chain comprises SEQ ID NO: 201.

3. The antibody or antigen-binding antibody fragment of claim 1, wherein the variable light chain comprises SEQ ID NO: 205.

4. The antibody or antigen-binding antibody fragment of claim 2, wherein the variable light chain comprises SEQ ID NO: 205.

5. The antibody or antigen-binding antibody fragment of claim 1, comprising a heavy chain comprising SEQ ID NO: 209.

6. The antibody or antigen-binding antibody fragment of claim 1, comprising a light chain comprising SEQ ID NO: 210.

7. The antibody or antigen-binding antibody fragment of claim 5, comprising a light chain comprising SEQ ID NO: 210.

8. The antibody or antigen-binding antibody fragment of claim 1, wherein the variable heavy chain comprises SEQ ID NO: 121.

9. The antibody or antigen-binding antibody fragment of claim 1, wherein the variable light chain comprises SEQ ID NO: 125.

10. The antibody or antigen-binding antibody fragment of claim 8, wherein the variable light chain comprises SEQ ID NO: 125.

11. The antibody or antigen-binding antibody fragment of claim 1, comprising a heavy chain comprising SEQ ID NO: 129.

12. The antibody or antigen-binding antibody fragment of claim 1, comprising a light chain comprising SEQ ID NO: 130.

13. The antibody or antigen-binding antibody fragment of claim 11, comprising a light chain comprising SEQ ID NO: 130.

14. A pharmaceutical composition comprising the antibody or antigen-binding antibody fragment of claim 1, and an inert non-toxic pharmaceutically suitable auxiliary.

15. A method for treatment of a disease associated with CD123 expression, comprising administering to a patient in need thereof an effective amount of the antibody or antigen-binding antibody fragment of claim 1.

* * * * *